(12) United States Patent
Li et al.

(10) Patent No.: US 8,546,394 B2
(45) Date of Patent: Oct. 1, 2013

(54) SUBSTITUTED [1,2,4]TRIAZOLO[4,3-A]PYRAZINE 11-BETA-HYDROXYSTEROID DEHYDROGENASE INHIBITORS

(75) Inventors: Jun Li, Princeton, NJ (US); James J. Li, Pennington, NJ (US); Stephen P. O'Connor, Princeton, NJ (US); Haixia Wang, Columbus, NJ (US); Lawrence J. Kennedy, Titusville, NJ (US); Jeffrey A. Robl, Newtown, PA (US); Lawrence G. Hamann, North Grafton, MA (US)

(73) Assignee: Bristol-Myers Squibb Company, Princeton, NJ (US)

(*) Notice: Subject to any disclaimer, the term of this patent is extended or adjusted under 35 U.S.C. 154(b) by 86 days.

(21) Appl. No.: 12/595,524

(22) PCT Filed: Apr. 16, 2008

(86) PCT No.: PCT/US2008/060395
§ 371 (c)(1),
(2), (4) Date: Oct. 12, 2009

(87) PCT Pub. No.: WO2008/130951
PCT Pub. Date: Oct. 30, 2008

(65) Prior Publication Data
US 2010/0144744 A1    Jun. 10, 2010

Related U.S. Application Data

(60) Provisional application No. 61/044,951, filed on Apr. 15, 2008, provisional application No. 60/912,186, filed on Apr. 17, 2007.

(51) Int. Cl.
*A61K 31/495* (2006.01)

(52) U.S. Cl.
USPC ............................................ 514/249; 544/350

(58) Field of Classification Search
USPC ............................................ 514/249; 544/350
See application file for complete search history.

(56) References Cited

U.S. PATENT DOCUMENTS

| | | | |
|---|---|---|---|
| 4,002,755 A | 1/1977 | Yamamoto et al. |
| 4,183,932 A | 1/1980 | Koshiba et al. |
| 4,209,621 A | 6/1980 | Albright |
| 4,402,958 A | 9/1983 | Izzo et al. |
| 5,064,953 A | 11/1991 | Ohnishi et al. |
| 7,271,170 B2 | 9/2007 | Xi et al. |
| 2006/0247245 A1 | 11/2006 | Xu |

FOREIGN PATENT DOCUMENTS

| | | |
|---|---|---|
| EP | 1050535 | 11/2000 |
| EP | 1277754 | 1/2003 |
| EP | 1719756 | 11/2006 |
| FR | 2662163 | * 11/1991 |
| JP | 2000319277 | 11/2000 |

(Continued)

OTHER PUBLICATIONS

Schneller, et al. Journal of Heterocyclic Chemistry, 15(6), 1978, 987-992.*
Spickett R G W et al: Bicyclic Pyrimidine Derivatives With a Bridgehead Nitrogen Atom. Part I. Synthesis of Striazol0[4,3-A]Pyrimidinesw, Journal of the Chemical Society, Section C: Organic Chemistry, No. 6, Jan. 1, 1967, pp. 498-502, XP001194584.

(Continued)

*Primary Examiner* — Douglas M Willis
(74) *Attorney, Agent, or Firm* — Terence J. Bogie

(57) ABSTRACT

Novel compounds are provided which are 1 1-beta-hydroxysteroid dehydrogenase type I inhibitors. 1 1-beta-hydroxysteroid dehydrogenase type I inhibitors are useful in treating, preventing, or slowing the progression of diseases requiring 1 1-beta-hydroxysteroid dehydrogenase type I inhibitor therapy. These novel compounds have the structure: W-L-Z or stereoisomers or prodrugs or pharmaceutically acceptable salts thereof, wherein W, L are defined herein and Z is selected from the following bicyclic heteroaryl groups: (a), (b), (c), (d).

W-L-Z  (I)

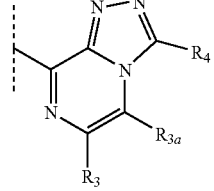

(a)

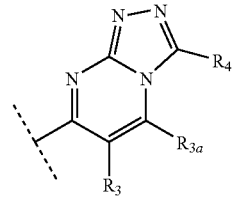

(b)

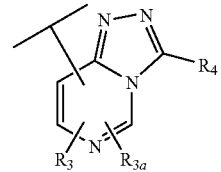

(c)

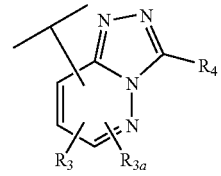

(d)

19 Claims, No Drawings

(56) References Cited

FOREIGN PATENT DOCUMENTS

| WO | WO 03/082817 | * | 10/2003 |
|----|--------------|---|---------|
| WO | WO2004/021984 | | 3/2004 |
| WO | WO2005/042537 | | 5/2005 |
| WO | WO 2006/023750 | * | 3/2006 |
| WO | WO2006/135667 | | 12/2006 |
| WO | WO2006/138657 | | 12/2006 |
| WO | WO2006/138682 | | 12/2006 |
| WO | WO2008/060488 | | 5/2008 |

OTHER PUBLICATIONS

Walser A et al: Triazolobenzo- and Triazolothienodiazepines as Potent Antagonists of Platelet Activating Factor,Journal of Medicinal Chemistry, vol. 34, No. 3, Jan. 1, 1991, pp. 1209-1221, XP000942214.

Huynh Dinh Tam et al: "Synthesis of C-nucleosides. 17. s-Triazolo 4,3-alpyrazines",The Journal of Organic Chemistry, vol. 44, No. 7, Mar. 1, 1979, pp. 1028-1035, XP55026693.

Doukhan G et al: "Synthese de C-nucleosides-XVIII (1)-Darabinofuranosyls-triazolo pyridines et pyrazines", European Journal of Medicinal Chemistry, vol. 14, Jan. 1, 1979, pp. 375-380, XP009157225.

Abdul-Ghani M et al: "A Novel and Direct Method for the Preparation of 4-Amino-I ,1,3 ,3-Tetrasubstttuted Guanidines and of [1 ,2,4]Triazolo-Fused Heterocyclic Derivatives",Organic Preparations and Procedures International,Organic Preparation and Procedures Co., vol. 36, No. 2, Jan. 1, 2004, pp. 121-127, XP009157192.

El-Hashah M A et al: "A facile one-pot conversion of chalcones to pyrimidine derivatives and their antimicrobial and antifungal activities", Indian Journal of Chemistry. Section 6: Organic and Medicinal Chemistry, Council of Scientific and Industrial Research (C S I R), IN, vol. 32, No. 4, Jan. 1, 1993, pp. 449-452, XP009157207.

R.P. Bokaldere and A.Ya. Liepin: "directed character of the guanylation of 5-amino-1,2,4-triazoles", Chemistry of Heterocyclic Compounds, vol. 9, No. 3, Mar. 1973, pp. 392-393.

Rousseaux et al., Tetrahydron Letters, vol. 27, No. 27, Jan. 1, 1986, pp. 3127-3128.

Potts et al., Journal of Heterocyclic Chemistry, vol. 5, Aug. 1, 1968, pp. 485-495.

Kim et al., Journal of Medicinal Chemistry, vol. 48, No. 1, Jan. 13, 2005, pp. 141-151.

Brown et al., Australian Journal of Chemistry, vol. 24, 1971, pp. 633-643.

Brown et al, Australian Journal of Chemistry, vol. 31, 1978, pp. 2505-2515.

Dennin et al., Journal of Heterocyclic Chemistry, vol. 26, 1989, pp. 991-996.

Khadem et al, Heterocycles, vol. 28, No. 1, Jan. 1, 1989, pp. 239-248.

Guillot et al., Tetrahedron, vol. 46, No. 11, Jan. 1, 1990, pp. 3897-3908.

* cited by examiner

SUBSTITUTED [1,2,4]TRIAZOLO[4,3-A]PYRAZINE 11-BETA-HYDROXYSTEROID DEHYDROGENASE INHIBITORS

CROSS REFERENCES TO RELATED APPLICATIONS

This application claims benefit to International Application No. PCT/US2008/060395 filed on Apr. 16, 2008, which claims the benefit of U.S. Provisional Application Serial Nos. 61/044,951 filed on Apr. 15, 2008 and 60/912,186 filed on Apr. 17, 2007. The entire teachings of the references applications are herein incorporated by reference in their entirety.

BACKGROUND OF THE INVENTION

The steroid hormone cortisol is a key regulator of many physiological processes. However, an excess of cortisol, as occurs in Cushing's Disease, provokes severe metabolic abnormalities including: type 2 diabetes, cardiovascular disease, obesity, and osteoporosis. Many patients with these diseases, however, do not show significant increases in plasma cortisol levels. In addition to plasma cortisol, individual tissues can regulate their glucocorticoid tone via the in situ conversion of inactive cortisone to the active hormone cortisol. Indeed, the normally high plasma concentration of cortisone provides a ready supply of precursor for conversion to cortisol via the intracellular enzyme 11-beta-hydroxysteroid dehydrogenase type I (11-beta-HSD1).

11-beta-HSD1 is a member of the short chain dehydrogenase superfamily of enzymes. By catalyzing the conversion of biologically inactive cortisone to cortisol, 11-beta-HSD1 controls the intracellular glucocorticoid tone according to its expression and activity levels. In this manner, 11-beta-HSD1 can determine the overall metabolic status of the organ. 11-beta-HSD1 is expressed at high levels in the liver and at lower levels in many metabolically active tissues including the adipose, the CNS, the pancreas, and the pituitary. Taking the example of the liver, it is predicted that high levels of 11-beta-HSD1 activity will stimulate gluconeogenesis and overall glucose output. Conversely, reduction of 11-beta-HSD1 activity will downregulate gluconeogenesis resulting in lower plasma glucose levels.

Various studies have been conducted that support this hypothesis. For example, transgenic mice expressing 2× the normal level of 11-beta-HSD1 in only the adipose tissue show abdominal obesity, hyperglycemia, and insulin resistance. (Masuzaki, H. et al., "A Transgenic Model of Visceral Obesity and the Metabolic Syndrome", *Science*, 294:2166-2170 (2001). Conversely, when the 11-beta-HSD1 gene is ablated by homologous recombination, the resulting mice are resistant to diet induced obesity and the accompanying dysregulation of glucose metabolism (Morton, N. M. et al., "Novel Adipose Tissue-Mediated Resistance to Diet-induced Visceral Obesity in 11β-Hydroxysteroid Dehydrogenase Type 1-Deficient Mice", *Diabetes*, 53:931-938 (2004). In addition, treatment of genetic mouse models of obesity and diabetes (ob/ob, db/db and KKAy mice) with a specific inhibitor of 11-beta-HSD1 causes a decrease in glucose output from the liver and an overall increase in insulin sensitivity (Alberts, P. et al., "Selective Inhibition of 11β-Hydroxysteroid Dehydrogenase Type I Improves Hepatic Insuling Sensitivity in Hyperglycemic Mice Strains", *Endocrinology*, 144:4755-4762 (2003)). Based in part on these studies, it is believed that local control of cortisol levels is important in metabolic diseases in these model systems. In addition, the results of these studies also suggest that inhibition of 11-beta-HSD1 will be a viable strategy for treating metabolic diseases such as type 2 diabetes, obesity, and the metabolic syndrome.

Lending further support to this idea are the results of a series of preliminary clinical studies. For example, several reports have shown that adipose tissue from obese individuals has elevated levels of 11-beta-HSD1 activity. In addition, studies with carbenoxolone, a natural product derived from licorice that inhibits both 11-beta-HSD1 and 11-beta-HSD2 (converts cortisol to cortisone in kidney) have shown promising results. A seven day, double blind, placebo controlled, cross over study with carbenoxolone in mildly overweight individuals with type 2 diabetes showed that patients treated with the inhibitor, but not the placebo group, displayed a decrease in hepatic glucose production (Andrews, R. C. et al., *J. Clin. Endocrinol. Metab.*, 88:285-291 (2003)). This observation is consistent with the inhibition of 11-beta-HSD1 in the liver. Furthermore, another clinical study reported that the inhibition of 11-beta-HSD1 may provide a novel treatment option for patients with glaucoma (Rauz et al., *IOVS*, 42(9): 2037-2042 (August 2001)). The results of these preclinical and early clinical studies strongly support the concept that treatment with a potent and selective inhibitor of 11-beta-HSD1 will be an efficacious therapy in patients afflicted with various disorders.

SUMMARY OF THE INVENTION

In accordance with the present invention, aryl and heterocyclyl and related compounds are provided that have the general structure of formula I:

W-L-Z    (I)

wherein W, L and Z are defined below.

Compounds of the present invention inhibit the activity of the enzyme 11-beta-hydroxysteroid dehydrogenase type I. Consequently, the compounds of the present invention may be used in the treatment of multiple diseases or disorders associated with 11-beta-hydroxysteroid dehydrogenase type I, such as diabetes and related conditions, microvascular complications associated with diabetes, the macrovascular complications associated with diabetes, cardiovascular diseases, glaucoma, Metabolic Syndrome and its component conditions, and other maladies. Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

The present invention provides for compounds of formula I, pharmaceutical compositions employing such compounds, and for methods of using such compounds. In particular, the present invention provides a pharmaceutical composition comprising a therapeutically effective amount of a compound of formula I, alone or in combination with a pharmaceutically acceptable carrier.

Further, in accordance with the present invention, a method is provided for preventing, inhibiting, or treating the progression or onset of diseases or disorders associated with the activity of the enzyme 11-beta-hydroxysteroid dehydrogenase type I, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s).

Further, the present invention provides a method for preventing, inhibiting, or treating the diseases as defined above and hereinafter, wherein a therapeutically effective amount of a combination of a compound of formula I and another compound of formula I and/or at least one other type of therapeutic agent, is administered to a mammalian, i.e., human, patient in need of treatment.

DESCRIPTION OF THE INVENTION

In accordance with the present invention, compounds of formula I are provided

W-L-Z   (I)

enantiomers, diastereomers, solvates, salts or prodrugs thereof wherein:

W is —C(=O)$R_6$, —C(OH)$R_6(R_6)$, —C(=O)O$R_6$, —C(=O)N$R_6R_6$, halogen, —OH, alkyl, alkenyl, aryl, cycloalkyl, heteroaryl or heterocyclyl, wherein the alkyl, alkenyl, aryl, cycloalkyl, heteroaryl or heterocyclyl may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —NO$_2$, —CO$_2R_6$, —CONR$_6R_6$, —SO$_2$NR$_6R_6$, —SOR$_6$, —SO$_2R_6$, —NR$_6$SO$_2R_6$, —NR$_6$CO$_2R_6$, —OCONR$_6R_6$, tetrazolyl, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

or alternatively any two $R_1$, $R_{1a}$, $R_{1b}$, $R_{1c}$ and $R_{1d}$ can be taken together to form a fused cycloalkyl, aryl, heteroaryl, heterocyclyl ring or spiro heterocyclyl ring;

L is a bond, O, S, SO, SO$_2$, C(=O), alkenyl, cycloalkyl, NR$_5$, CR$_2R_{2a}$, CR$_2R_6$, CR$_2R_{2a}$CR$_{2b}R_{2c}$, SO$_2$NR$_6$, OCR$_2R_{2a}$, OCR$_2R_{2a}$CR$_{2b}R_{2c}$, CR$_2R_{2a}$O, CR$_{2b}R_{2c}$CR$_2R_{2a}$O, N(R$_5$)CR$_2R_{2a}$, CR$_2R_{2a}$N(R$_5$), SCR$_2R_{2a}$, CR$_2R_{2a}$S, CR$_2R_{2a}$SO, CR$_2R_{2a}$SO$_2$, SOCR$_2R_{2a}$, SO$_2$CR$_2R_{2a}$, CR$_2R_{2a}$OCR$_{2b}R_{2c}$, CR$_2R_{2a}$SCR$_{2b}R_{2c}$, CR$_2R_{2a}$SO$_2$CR$_{2b}R_{2c}$, SO$_2$NR$_6$CR$_2R_{2b}$, COCR$_2R_{2a}$, CR$_2R_{2a}$CO, CONR$_6$CR$_2R_{2b}$, CR$_2R_{2a}$CR$_{2b}R_{2c}$S, CR$_2R_{2a}$CR$_{2b}R_{2c}$SO, CR$_2R_{2a}$CR$_{2b}R_{2c}$SO$_2$, provided that W is not halogen or —OH when L is O, S, SO, SO$_2$, C(=O) or NR$_5$;

$R_2$, $R_{2a}$, $R_{2b}$ and $R_{2c}$ are independently hydrogen, halogen, —OH, alkyl, cycloalkyl, aryl, or haloalkyl;

or alternatively any two $R_2$, $R_{2a}$, $R_{2b}$, and $R_{2c}$ can be taken together to which the atom they are attached to form a cycloalkyl, halogen substituted cycloalkyl or heterocyclyl ring;

Z is selected from the following bicyclic heteroaryl groups:

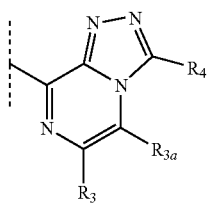

(a)

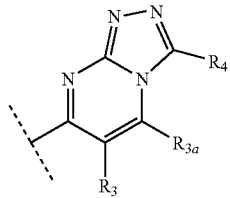

(b)

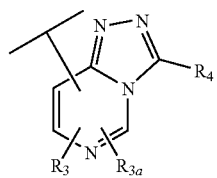

(c)

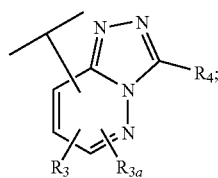

(d)

$R_3$ is hydrogen, halogen, —OH, —CN, —NO$_2$, —CO$_2R_6$, —CONR$_6R_6$, —SO$_2$NR$_6R_6$, —SOR$_6$, —SO$_2R_6$, —NR$_6$SO$_2R_6$, —NR$_6$CO$_2R_6$, —OCONR$_6R_6$, tetrazolyl, alkyl, haloalkyl, cycloalkyl, alkoxy, aryloxy, alkenyl, haloalkoxy, alkylthio, arylthio, arylsulfonyl, alkylamino, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_{3a}$ is hydrogen, halogen, —OH, —CN, —NO$_2$, —CO$_2R_6$, —CONR$_6R_6$, —SO$_2$NR$_6R_6$, —SOR$_6$, —SO$_2R_6$, —NR$_6$SO$_2R_6$, —NR$_6$CO$_2R_6$, —OCONR$_6R_6$, tetrazolyl, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

or alternatively any $R_3$ and $R_{3a}$ can be taken together to form a fused cycloalkyl, aryl, heteroaryl or heterocyclyl ring, which may be optionally substituted with $R_1$, $R_{1a}$, $R_{1b}$, $R_{1c}$ and $R_{1d}$;

or alternatively one of $R_3$ or $R_{3a}$ can be taken together with W-L to form a fused cycloalkyl, aryl, heteroaryl or heterocyclyl ring, which may be optionally substituted with $R_1$, $R_{1a}$, $R_{1b}$, $R_{1c}$ and $R_{1d}$;

$R_4$ is cycloalkyl, which may be optionally substituted with one or more substituents selected from halogen, —OH, —OR$_6$, —SR$_6$, —OCOR$_6$, —CN, —NR$_6$COR$_6$, —NR$_6$SO$_2R_6$, —COR$_6$, —CO$_2R_6$, —CO$_2$H, —OCONR$_6R_6$, —CONR$_6R_6$, —NR$_6$CO$_2R_6$, —SO$_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; provided that $R_4$ is not cycloalkyl when (i) W is aryl, cycloalkyl, heteroaryl or heterocyclyl and (ii) Z is formula (d); or $R_4$ is heterocyclyl, which may be optionally substituted with one or more substituents selected from halogen, —OH, —$OR_6$, —$SR_6$, —$OCOR_6$, —CN, —$NR_6COR_6$, —$NR_6SO_2R_6$, —$COR_6$, —$CO_2R_6$, —$CO_2H$, —$OCONR_6R_6$, —$CONR_6R_6$, —$NR_6CO_2R_6$, —$SO_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, Spiro heterocycloalkyl, aryl, heteroaryl or heterocyclyl may be optionally substituted with $R_7$, $R_{7a}$, $R_{7b}$, and $R_{7c}$; or $R_4$ is alkyl, which may be optionally substituted with one or more substituents selected from halogen, —OH, —$OR_6$, —$SR_6$, —$OCOR_6$, —CN, —$NR_6COR_6$, —$NR_6SO_2R_6$, —$COR_6$, —$CO_2R_6$, —$CO_2H$, —$OCONR_6R_6$, —$CONR_6R_6$, —$NR_6CO_2R_6$, —$SO_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_5$, at each occurrence, is independently hydrogen, alkyl, cycloalkyl, aryl, haloalkyl, $COR_6$, $CO_2R_6$, $SO_2NR_6R_6$, or $SO_2R_6$;

$R_6$, at each occurrence, is independently H, alkyl, cycloalkyl, aryl or heteroaryl, all of which may be optionally substituted with $R_7$, $R_{7a}$, $R_{7b}$, and $R_{7c}$; or two $R_6$'s may be taken together with the atom to which they are attached to form a 3- to 7-membered cycloalkyl or heterocyclyl ring, which may be optionally substituted with $R_7$, $R_{7a}$, $R_{7b}$ and $R_{7c}$;

$R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with $R_8$, $R_{8a}$, $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol.

In one embodiment, compounds of formula I are provided wherein W is alkyl, aryl, cycloalkyl, heteroaryl or heterocyclyl, all of which may be optionally substituted with $R_1$, $R_{1a}$, $R_{1b}$, $R_{1c}$ and $R_{1d}$.

In another embodiment, compounds of formula I are provided wherein W is phenyl or cyclopropyl, both of which are optionally substituted with $R_1$, $R_{1a}$, $R_{1b}$, $R_{1c}$ and $R_{1d}$.

In still another embodiment, compounds of formula I are provided wherein Z is selected from the following bicyclic heteroaryl groups:

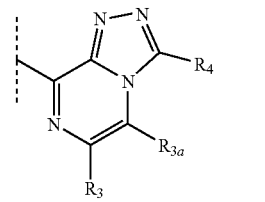

(a)

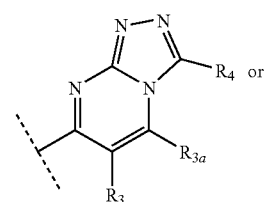

(b)

or

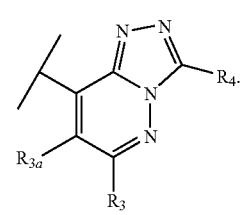

(d-1)

In still another embodiment, compounds of formula I are provided wherein:

$R_4$ is cycloalkyl, which may be optionally substituted with one or more substituents selected from halogen, —OH, —$OR_6$, —$SR_6$, —$OCOR_6$, —CN, —$NR_6COR_6$, —$NR_6SO_2R_6$, —$COR_6$, —$CO_2R_6$, —$CO_2H$, —$OCONR_6R_6$, —$CONR_6R_6$, —$NR_6CO_2R_6$, —$SO_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, Spiro heterocycloalkyl, aryl, heteroaryl or heterocyclyl may be optionally substituted with $R_7$, $R_{7a}$, $R_{7b}$, and $R_{7c}$; provided that $R_4$ is not cycloalkyl when (i) W is aryl, cycloalkyl, heteroaryl or heterocyclyl and (ii) Z is formula (d); or $R_4$ is alkyl, which may be optionally substituted with one or more substituents selected from halogen, —OH, —$OR_6$, —$SR_6$, —$OCOR_6$, —CN, —$NR_6COR_6$, —$NR_6SO_2R_6$, —$CO_2R_6$, —$CO_2H$, —$OCONR_6R_6$, —$CONR_6R_6$, —$NR_6CO_2R_6$, —$SO_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_5$, at each occurrence, is independently hydrogen, alkyl, cycloalkyl, aryl, haloalkyl, $COR_6$, $CO_2R_6$, $SO_2NR_5R_6$, or $SO_2R_6$;

$R_6$, at each occurrence, is independently alkyl, cycloalkyl, aryl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO₂, —CN, —CO₂H, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with $R_8$, $R_{8a}$; $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO₂, —CN, —CO₂H, tetrazolyl or thiol.

In yet still another embodiment, compounds of formula I are provided wherein:

Z is selected from the following bicyclic heteroaryl groups:

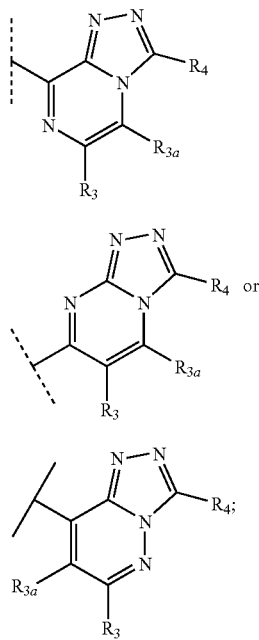

$R_4$ is cycloalkyl, which may be optionally substituted with one or more substituents selected from halogen, —OH, —OR₆, —SR₆, —OCOR₆, —CN, —NR₆COR₆, —NR₆SO₂R₆, —COR₆, —CO₂R₆, —CO₂H, —OCONR₆R₆, —CONR₆R₆, —NR₆CO₂R₆, —SO₂R₆, alkyl, cycloalkyl, spiro cycloalkyl, spiro heterocycloalkyl, alkoxy, aryl, amino, heterocyclyl or heteroaryl, wherein the alkyl, alkoxy, cycloalkyl, spiro cycloalkyl, aryl, heteroaryl or heterocyclyl may be optionally substituted with $R_7$, $R_{7a}$, $R_{7b}$, and $R_{7c}$; provided that $R_4$ is not cycloalkyl when (i) W is aryl, cycloalkyl, heteroaryl or heterocyclyl and (ii) Z is formula (d-1);

$R_5$, at each occurrence, is independently hydrogen, alkyl, cycloalkyl, aryl, haloalkyl, COR₆, CO₂R₆, SO₂NR₆R₆, or SO₂R₆;

$R_6$, at each occurrence, is independently alkyl, cycloalkyl, aryl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO₂, —CN, —CO₂H, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with $R_8$, $R_{8a}$, $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO₂, —CN, —CO₂H, tetrazolyl or thiol.

In one embodiment, compounds of formula I are provided wherein:

W is alkyl, aryl, cycloalkyl, heteroaryl or heterocyclyl, all of which may be optionally substituted with $R_1$, $R_{1a}$, $R_{1b}$, $R_{1c}$ and $R_{1d}$;

$R_{1a}$, $R_{1b}$, $R_{1c}$ and $R_{1d}$ are independently hydrogen, halogen, —OH, —CN, —NO₂, —CO₂R₆, —CONR₆R₆, —SO₂NR₆R₆, —SOR₆, —SO₂R₆, —NR₆SO₂R₆, —NR₆CO₂R₆, —OCONR₆R₆, tetrazolyl, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

L is a bond, O, S, SO₂, C(=O), CR₂R₂ₐ, CR₂R₆, SO₂NR₆, OCR₂R₂ₐ, OCR₂R₂ₐCR₂ᵦR₂c, CR₂R₂ₐO, CR₂ᵦR₂cCR₂R₂ₐO, SCR₂R₂ₐ, CR₂R₂ₐS, CR₂R₂ₐSO, CR₂R₂ₐSO₂, SO₂CR₂R₂ₐ, CR₂R₂ₐOCR₂ᵦR₂c, CR₂R₂ₐSCR₂ᵦR₂c, CR₂R₂ₐSO₂CR₂ᵦR₂c, SO₂NR₆CR₂ₐR₂ᵦ, COCR₂R₂ₐ, CR₂R₂ₐCO, CONR₆CR₂ₐR₂ᵦ, CR₂R₂ₐCR₂ᵦR₂cS, CR₂R₂ₐCR₂ᵦR₂cSO, or CR₂R₂ₐCR₂ᵦR₂cSO₂;

$R_2$, $R_{2a}$, $R_{2b}$ and $R_{2c}$ are independently hydrogen, halogen, —OH, alkyl, cycloalkyl, aryl or haloalkyl;

Z is selected from the following bicyclic heteroaryl groups:

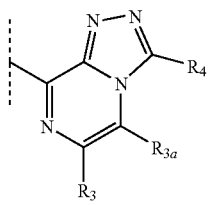

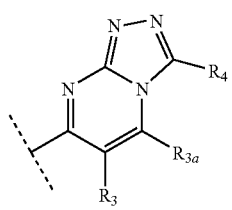

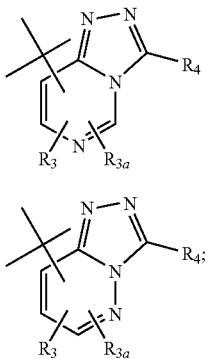

R$_3$ is hydrogen, halogen, —OH, —CN, —NO$_2$, —CO$_2$R$_6$, —CONR$_6$R$_6$, —SO$_2$NR$_6$R$_6$, —SOR$_6$, —SO$_2$R$_6$, —NR$_6$SO$_2$R$_6$, —NR$_6$CO$_2$R$_6$, —OCONR$_6$R$_6$, tetrazolyl, alkyl, haloalkyl, cycloalkyl, alkoxy, aryloxy, alkenyl, haloalkoxy, alkylthio, arylthio, arylsulfonyl, alkylamino, arylamino, heteroarylamino, aryl, heteroaryl or heterocyclyl, wherein the tetrazolyl, alkyl, cycloalkyl, aryl, heteroaryl or heterocyclyl may be optionally substituted with R$_7$, R$_{7a}$, R$_{7b}$, and R$_{7c}$;

R$_{3a}$ is hydrogen, halogen, —OH, —CN, —NO$_2$, —CO$_2$R$_6$, —CONR$_6$R$_6$, —SO$_2$NR$_6$R$_6$, —SOR$_6$, —SO$_2$R$_6$, —NR$_6$SO$_2$R$_6$, —NR$_6$CO$_2$R$_6$, —OCONR$_6$R$_6$, tetrazolyl, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with R$_7$, R$_{7a}$, R$_{7b}$, and R$_{7c}$;

R$_4$ is cycloalkyl, which may be optionally substituted with one or more substituents selected from halogen, —OH, —OR$_6$, —SR$_6$, —OCOR$_6$, —CN, —NR$_6$COR$_6$, —NR$_6$SO$_2$R$_6$, —COR$_6$, —CO$_2$R$_6$, —CO$_2$H, —OCONR$_6$R$_6$, —CONR$_6$R$_6$, —NR$_6$CO$_2$R$_6$, —SO$_2$R$_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with R$_7$, R$_{7a}$, R$_{7b}$, and R$_{7c}$; provided that R$_4$ is not cycloalkyl when (i) W is aryl, cycloalkyl, heteroaryl or heterocyclyl and (ii) Z is formula (d); or R$_4$ is alkyl, which may be optionally substituted with one or more substituents selected from halogen, —OH, —OR$_6$, —SR$_6$, —OCOR$_6$, —CN, —NR$_6$COR$_6$, —NR$_6$SO$_2$R$_6$, —COR$_6$, —CO$_2$R$_6$, —CO$_2$H, —OCONR$_6$R$_6$, —CONR$_6$R$_6$, —NR$_6$CO$_2$R$_6$, —SO$_2$R$_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with R$_7$, R$_{7a}$, R$_{7b}$, and R$_{7c}$;

R$_5$, at each occurrence, is independently hydrogen, alkyl, cycloalkyl, aryl, haloalkyl, COR$_6$ or CO$_2$R$_6$;

R$_6$, at each occurrence, is independently alkyl, cycloalkyl, aryl or heteroaryl, all of which may be optionally substituted with R$_7$, R$_{7a}$, R$_{7b}$, and R$_{7c}$;

R$_7$, R$_{7a}$, R$_{7b}$, and R$_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN, —CO$_2$H, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with R$_8$, R$_{8a}$, R$_{8b}$, and R$_{8c}$; and R$_8$, R$_{8a}$, R$_{8b}$, and R$_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN, —CO$_2$H, tetrazolyl or thiol.

In another embodiment, compounds of formula I are provided wherein:

W is alkyl, aryl, cycloalkyl or heteroaryl, all of which may be optionally substituted with R$_1$, R$_{1a}$, R$_{1b}$, R$_{1c}$ and R$_{1d}$;

R$_1$, R$_{1a}$, R$_{1b}$, R$_{1c}$ and R$_{1d}$ are independently hydrogen, halogen, —OH, —CN, —NO$_2$, —CO$_2$R$_6$, —CONR$_6$R$_6$, —SO$_2$NR$_6$R$_6$, —SOR$_6$, —SO$_2$R$_6$, —OCONR$_6$R$_6$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with R$_7$, R$_{7a}$, R$_{7b}$, and R$_{7c}$;

L is a bond, O, S, SO, SO$_2$, NR$_2$, CR$_2$R$_{2a}$, CR$_2$R$_6$, CR$_2$R$_{2a}$CR$_{2b}$R$_{2c}$, OCR$_2$R$_{2a}$, CR$_2$R$_{2a}$O, SCR$_2$R$_{2c}$, CR$_2$R$_{2a}$S, CR$_2$R$_{2a}$OR$_{2b}$R$_{2c}$, CR$_2$R$_{2a}$SCR$_{2b}$R$_{2c}$, CR$_2$R$_{2a}$SO$_2$CR$_{2b}$R$_{2c}$ or SO$_2$NR$_6$CR$_{2a}$R$_{2b}$;

R$_2$, R$_{2a}$, R$_{2b}$ and R$_{2c}$ are independently hydrogen, halogen, —OH, alkyl, cycloalkyl, aryl or haloalkyl;

Z is selected from the following bicyclic heteroaryl groups:

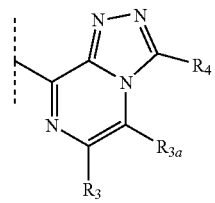

(a)

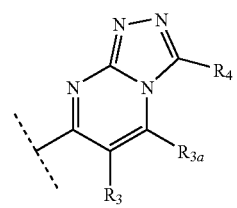

(b)

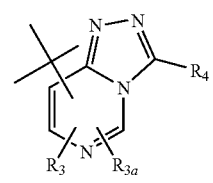

(c)

-continued

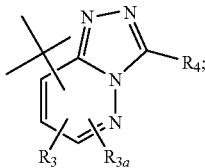

(d)

$R_3$ is hydrogen, halogen, —OH, —CN, —NO$_2$, —CO$_2$R$_6$, —CONR$_6$R$_6$, —SO$_2$NR$_6$R$_6$, —SOR$_6$, —SO$_2$R$_6$, —OCONR$_6$R$_6$, tetrazolyl, alkyl, haloalkyl, cycloalkyl, alkoxy, aryloxy, haloalkoxy, alkylthio, arylthio, arylsulfonyl, alkylamino, arylamino, heteroarylamino, aryl, heteroaryl or heterocyclyl, wherein the tetrazolyl, alkyl, cycloalkyl, aryl, heteroaryl or heterocyclyl may be optionally substituted, with $R_7$, $R_{7a}$, $R_{7b}$, and $R_{7c}$;

$R_{3a}$ is hydrogen, halogen, —OH, —CN, —NO$_2$, —CO$_2$R$_6$, —CONR$_6$R$_6$, —SO$_2$NR$_6$R$_6$, —SOR$_6$, —SO$_2$R$_6$, —OCONR$_6$R$_6$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_4$ is cycloalkyl, which may be optionally substituted with one or more substituents selected from halogen, —OH, —OR$_6$, —SR$_6$, —OCOR$_6$, —CN, —COR$_6$, —CO$_2$R$_6$, —CO$_2$H, —OCONR$_6$R$_6$, —CONR$_6$R$_6$, —SO$_2$R$_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; provided that $R_4$ is not cycloalkyl when (i) W is aryl, cycloalkyl or heteroaryl and (ii) Z is formula (d); or $R_4$ is alkyl, which may be optionally substituted with one or more substituents selected from halogen, —OH, —OR$_6$, —SR$_6$, —OCOR$_6$, —CN, —COR$_6$, —CO$_2$R$_6$, —CO$_2$H, —OCONR$_6$R$_6$, —CONR$_6$R$_6$, —SO$_2$R$_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN, —CO$_2$H, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with $R_8$, $R_{8a}$, $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN, —CO$_2$H, tetrazolyl or thiol.

In still another embodiment, compounds of formula I are provided wherein:

W is alkyl, aryl or cycloalkyl, all of which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —NO$_2$, —CO$_2$R$_6$, —CONR$_6$R$_6$, —SO$_2$NR$_6$R$_6$, —OCONR$_6$R$_6$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

L is a bond, O, S, SO, SO$_2$, C(=O), CR$_2$R$_{2a}$, CR$_2$R$_6$, OCR$_2$R$_{2a}$, CR$_2$R$_{2a}$O, SO$_2$NR$_6$CR$_{2a}$R$_{2b}$ or CR$_2$R$_{2a}$OCR$_{2b}$R$_{2c}$;

$R_2$, $R_{2a}$, $R_{2b}$ and $R_{2c}$ are independently hydrogen, halogen, —OH, alkyl, cycloalkyl, aryl or haloalkyl;

Z is selected from the following bicyclic heteroaryl groups:

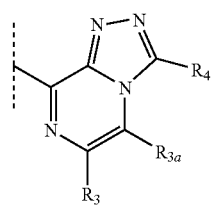

(a)

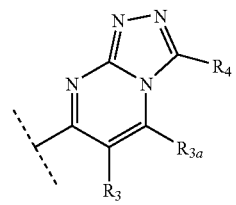

(b)

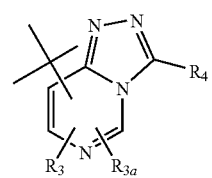

(c)

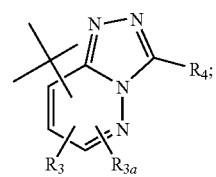

(d)

$R_3$ is hydrogen, halogen, —OH, —CN, —NO$_2$, —CO$_2$R$_6$, —CONR$_6$R$_6$, —SO$_2$NR$_6$R$_6$, —OCONR$_6$R$_6$, tetrazolyl, alkyl, haloalkyl, cycloalkyl, alkoxy, aryloxy, haloalkoxy, alkylthio, arylthio, arylsulfonyl, alkylamino, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_{3a}$ is hydrogen, halogen, —OH, —CN, —NO$_2$, —CO$_2$R$_6$, —CONR$_6$R$_6$, —SO$_2$NR$_6$R$_6$, —OCONR$_6$R$_6$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_4$ is cycloalkyl, which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_6R_6$, —$CONR_6R_6$, —$SO_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; provided that $R_4$ is not cycloalkyl when (i) W is aryl or cycloalkyl and (ii) Z is formula (d); or $R_4$ is alkyl, which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_6R_6$, —$CONR_6R_6$, —$SO_2R_6$, alkyl, cycloalkyl, spiro cycloalkyl, spiro heterocycloalkyl, aryl, amino, heterocyclyl or heteroaryl, wherein the alkyl, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with $R_8$, $R_{8a}$, $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol.

In yet still another embodiment, compounds of formula I are provided wherein:

W is alkyl, aryl or cycloalkyl, all of which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —$NO_2$, —$CO_2R_6$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

L is a bond, O, S, SO, $SO_2$, C(=O), $CR_2R_{2a}$, $CR_2R_6$, $OCR_2R_{2a}$, $CR_2R_{2a}O$, $SO_2NR_6CR_2R_{2b}$ or $CR_2R_{2a}OCR_{2b}R_{2c}$;

$R_2$, $R_{2a}$, $R_{2b}$ and $R_{2c}$ are independently hydrogen, halogen, —OH, alkyl, cycloalkyl, aryl or haloalkyl;

Z is selected from the following bicyclic heteroaryl groups:

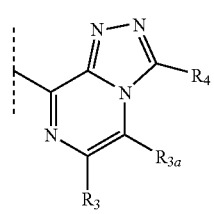

(a)

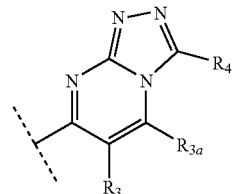

(b)

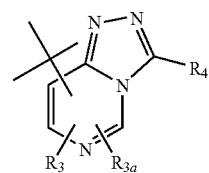

(c)

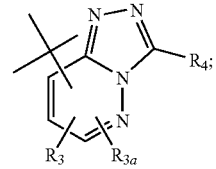

(d)

$R_3$ is hydrogen, halogen, —OH, —CN, —$NO_2$, —$CO_2R_6$, tetrazolyl, alkyl, haloalkyl, cycloalkyl, alkoxy, aryloxy, haloalkoxy, alkylthio, arylthio, arylsulfonyl, alkylamino, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_{3a}$ is hydrogen, halogen, —OH, —CN, —$NO_2$, —$CO_2R_6$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_4$ is cycloalkyl, which may be optionally substituted with one or more substituents selected from halogen, —OH, —$OR_6$, —$SR_6$, —CN, —$COR_6$, —$CO_2R_6$, —$CO_2H$, —$CONR_6R_6$, —$SO_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; provided that $R_4$ is not cycloalkyl when (i) W is aryl or cycloalkyl and (ii) Z is formula (d); or $R_4$ is alkyl, which may be optionally substituted with one or more substituents selected from halogen, —OH, —$OR_6$, —$SR_6$, —CN, —$COR_6$, —$CO_2R_6$, —$CO_2H$, —$CONR_6R_6$, —$SO_2R_6$, alkyl, alkoxy, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

R$_6$, at each occurrence, is independently alkyl, cycloalkyl, aryl or heteroaryl, all of which may be optionally substituted with R$_7$, R$_{7a}$, R$_{7b}$, and R$_{7c}$;

R$_7$, R$_{7a}$, R$_{7b}$, and R$_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN, —CO$_2$H, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with R$_8$, R$_{8a}$, R$_{8b}$, and R$_{8c}$; and R$_8$, R$_{8a}$, R$_{8b}$, and R$_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN, —CO$_2$H, tetrazolyl or thiol.

In one embodiment, compounds of formula I are provided wherein:

W is alkyl, aryl or cycloalkyl, all of which may be optionally substituted with R$_1$, R$_{1a}$, R$_{1b}$, R$_{1c}$ and R$_{1d}$;

R$_1$, R$_{1a}$, R$_{1b}$, R$_{1c}$ and R$_{1d}$ are independently hydrogen; halogen, —OH, —CN, —NO$_2$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with R$_7$, R$_{7a}$, R$_{7b}$, and R$_{7c}$;

L is a bond, O, S, SO, SO$_2$, C(═O), CR$_2$R$_{2a}$, CR$_2$R$_6$, OCR$_2$R$_{2a}$, CR$_2$R$_{2a}$O, SO$_2$NR$_6$CR$_2$$_a$R$_{2b}$ or CR$_2$R$_{2a}$OR$_{2b}$R$_{2c}$;

R$_2$, R$_{2a}$, R$_{2b}$ and R$_{2c}$ are independently hydrogen, halogen, —OH, alkyl, cycloalkyl, aryl or haloalkyl;

Z is selected from the following bicyclic heteroaryl groups:

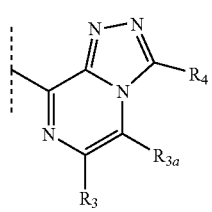

(a)

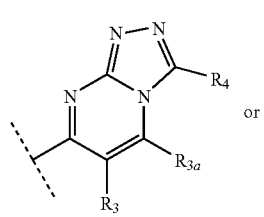

(b)

or

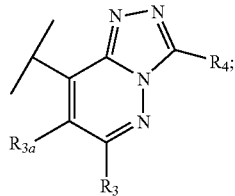

(d-1)

R$_3$ is hydrogen, halogen, —OH, —CN, —NO$_2$, tetrazolyl, alkyl, haloalkyl, cycloalkyl, alkoxy, aryloxy, haloalkoxy, alkylthio, arylthio, arylsulfonyl, alkylamino, arylamino, heteroarylamino, aryl, heteroaryl or heterocyclyl, wherein the tetrazolyl, alkyl, cycloalkyl, aryl, heteroaryl or heterocyclyl may be optionally substituted with R$_7$, R$_{7a}$, R$_{7b}$, and R$_{7c}$;

R$_{3a}$ is hydrogen, halogen, —OH, —CN, —NO$_2$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with R$_7$, R$_{7a}$, R$_{7b}$, and R$_{7c}$;

R$_4$ is cycloalkyl, which may be optionally substituted with one or more substituents selected from halogen, —OH, —OR$_6$, —SR$_6$, —CN, —COR$_6$, —CO$_2$R$_6$, —CO$_2$H, —CONR$_6$R$_6$, —SO$_2$R$_6$, alkyl, alkoxy, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with R$_7$, R$_{7a}$, R$_{7b}$, and R$_{7c}$; provided that R$_4$ is not cycloalkyl when (i) W is aryl or cycloalkyl and (ii) Z is formula (d-1);

R$_6$, at each occurrence, is independently alkyl, cycloalkyl, aryl or heteroaryl, all of which may be optionally substituted with R$_7$, R$_{7a}$, R$_{7b}$, and R$_{7c}$;

R$_7$, R$_{7a}$, R$_{7b}$, and R$_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, (heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN, —CO$_2$H, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with R$_8$, R$_{8a}$, R$_{8b}$, and R$_{8c}$; and R$_8$, R$_{8a}$, R$_{8b}$, and R$_{8c}$, at each occurrence, are independently halo, alkyl, haloalkyl, alkoxy, aryl, aryloxy, arylaryl, arylalkyl, arylalkyloxy, alkenyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN, —CO$_2$H, tetrazolyl or thiol.

In another embodiment, compounds of formula I are provided wherein:

W is alkyl, aryl or cycloalkyl, all of which may be optionally substituted with R$_1$, R$_{1a}$, R$_{1b}$, R$_{1c}$ and R$_{1d}$;

R$_1$, R$_{1a}$, R$_{1b}$, R$_{1c}$ and R$_{1d}$ are independently hydrogen, halogen, —OH, —CN, —NO$_2$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

L is a bond, O, S, SO, $SO_2$, $CR_2R_{2a}$, $CR_2R_6$, $OCR_2R_{2a}$, $CR_2R_{2a}O$, $SO_2NR_6CR_{2a}R_{2b}$ or $CR_2R_{2a}OCR_{2b}R_{2c}$;

$R_2$, $R_{2a}$, $R_{2b}$ and $R_{2c}$ are independently hydrogen, halogen, —OH, alkyl, cycloalkyl, aryl or haloalkyl;

Z is selected from the following bicyclic heteroaryl groups:

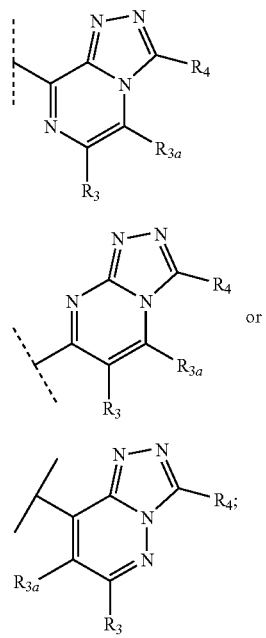

$R_3$ is hydrogen, halogen, —OH, —CN, —$NO_2$, tetrazolyl, alkyl, haloalkyl, cycloalkyl, alkoxy, aryloxy, haloalkoxy, alkylthio, arylthio, arylsulfonyl, alkylamino, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_{3a}$ is hydrogen, halogen, —OH, —CN, —$NO_2$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{1a}$, $R_{1b}$, and $R_{7c}$;

$R_4$ is alkyl, which may be optionally substituted with one or more substituents selected from halogen, —OH, —$OR_6$, —$SR_6$, —CN, —$COR_6$, —$CO_2R_6$, —$CO_2H$, —$CONR_6R_6$, —$SO_2R_6$, alkyl, alkoxy, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with $R_8$, $R_{8a}$, $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol.

In still another embodiment, compounds of formula I are provided wherein:

W is aryl or cycloalkyl, both of which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are hydrogen, halogen, —OH, —CN, —$NO_2$, tetrazolyl, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

L is a bond, O, S, C(=O), $CR_2R_{2a}$, $CR_2R_6$, $OCR_2R_{2a}$, $CR_2R_{2a}O$ or $CR_2R_{2a}OR_{2b}R_{2c}$;

$R_2$, $R_{2a}$, $R_{2b}$ and $R_{2c}$ are independently hydrogen, halogen, —OH, alkyl, cycloalkyl, aryl or haloalkyl;

Z is selected from the following bicyclic heteroaryl groups:

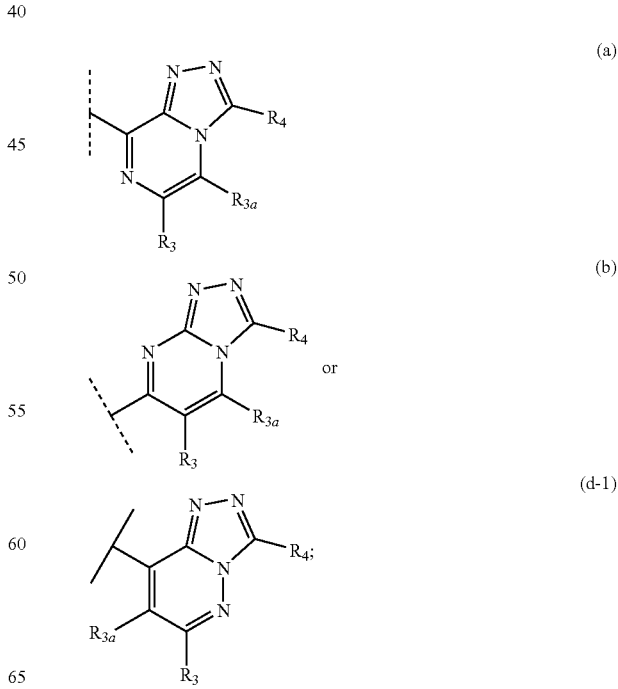

$R_3$ is hydrogen, halogen, —OH, —CN, —NO$_2$, tetrazolyl, alkyl, haloalkyl, cycloalkyl, alkoxy, aryloxy, haloalkoxy, alkylthio, arylthio, arylsulfonyl, alkylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_{3a}$ is hydrogen, halogen, —OH, —CN, —NO$_2$, tetrazolyl, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_4$ is cycloalkyl, which may be optionally substituted with one or more substituents selected from halogen, —OH, —OR$_6$, —SR$_6$, —CN, —COR$_6$, —CO$_2$R$_6$, —CO$_2$H, alkyl, alkoxy, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; provided that $R_4$ is not cycloalkyl when Z is formula (d-1); or $R_4$ is alkyl, which may be optionally substituted with one or more substituents selected from halogen, —OH, —OR$_6$, —SR$_6$, —CN, —COR$_6$, —CO$_2$R$_6$, —CO$_2$H, —CONR$_6$R$_6$, —SO$_2$R$_6$, alkyl, alkoxy, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl;

$R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN, —CO$_2$H, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with $R_8$, $R_{8a}$, $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN, —CO$_2$H, tetrazolyl or thiol.

In another embodiment, compounds of formula I are provided wherein:

W is phenyl or cyclopropyl, both of which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —NO$_2$, tetrazolyl, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl;

L is a bond, O, S, C(=O), CHR$_6$, SCH$_2$, OCH$_2$, CH$_2$O or CH$_2$OCH$_2$;

Z is selected from the following bicyclic heteroaryl groups:

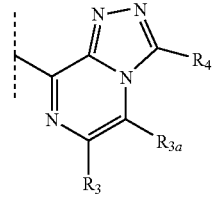

(a)

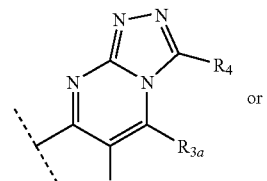

or (b)

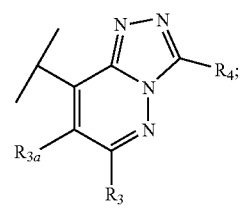

(d-1)

$R_3$ is hydrogen, halogen, —OH, —CN, —NO$_2$, tetrazolyl, alkyl, haloalkyl, cycloalkyl, alkoxy, aryloxy, haloalkoxy, alkylthio, arylthio, arylsulfonyl, alkylamino, aryl, heteroaryl or heterocyclyl;

$R_{3a}$ is hydrogen, halogen, —OH, —CN, —NO$_2$, tetrazolyl, alkyl, haloalkyl, cycloalkyl, alkoxy, aryloxy, haloalkoxy, alkylthio, arylthio, arylsulfonyl, allylamino, aminoalkyl, aryl, heteroaryl or heterocyclyl;

$R_4$ is cycloalkyl, which may be optionally substituted with one or more substituents selected from halogen, —OH, —OR$_5$, —SR$_6$, —CN, alkyl, alkoxy, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; provided that $R_4$ is not cycloalkyl when Z is formula (d-1); or $R_4$ is alkyl, which may be optionally substituted with one or more substituents selected from halogen, —OH, —OR$_6$, —SR$_6$, —CN, —COR$_6$, —CO$_2$R$_6$, —CO$_2$H, —CONR$_6$R$_6$, —SO$_2$R$_6$, alkyl, alkoxy, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl;

$R_7$, $R_{7a}$, $R_{7b}$, and $R_{7c}$, at each occurrence, are independently halo, alkyl, haloalkyl, alkoxy, aryl, aryloxy, arylalkyl, cycloalkyl, amino, —OH, hydroxyalkyl, heteroaryl, heteroaryloxy, heteroarylalkyl, alkylthio, arylalkylthio, —NO$_2$, —CN, —CO$_2$H or tetrazolyl; wherein the alkyl, alkoxy, aryl, aryloxy, arylalkyl, cycloalkyl, heteroaryl, heteroaryloxy, heteroarylalkyl, alkylthio, arylalkylthio or tetrazolyl may be optionally substituted with $R_8$, $R_{8a}$, $R_{8b}$, and $R_{8c}$; and R$_8$, R$_{8a}$, R$_{8b}$, and R$_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN, —CO$_2$H, tetrazolyl or thiol.

In one embodiment, compounds of formula I are provided wherein L is a bond or O.

In another embodiment, compounds of the present invention are selected from the compounds exemplified in the examples.

In another embodiment, the present invention relates to pharmaceutical compositions comprised of a therapeutically effective amount of a compound of the present invention, alone or, optionally, in combination with a pharmaceutically acceptable carrier and/or one or more other agent(s).

In another embodiment, the present invention relates to methods of inhibiting the activity of the enzyme 11-beta-hydroxysteroid dehydrogenase type I comprising administering to a mammalian patient, for example, a human patient, in need thereof a therapeutically effective amount of a compound of the present invention, alone, or optionally, in combination with another compound of the present invention and/or at least one other type of therapeutic agent.

In another embodiment, the present invention relates to a method for preventing, inhibiting, or treating the progression or onset of diseases or disorders associated with the activity of the enzyme 11-beta-hydroxysteroid dehydrogenase type I comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

In another embodiment, the present invention relates to a method for preventing, inhibiting, or treating the progression or onset of diabetes, hyperglycemia, obesity, dyslipidemia, hypertension and cognitive impairment comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In still another embodiment, the present invention relates to a method for preventing, inhibiting, or treating the progression or onset of diabetes, comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In yet still another embodiment, the present invention relates to a method for preventing, inhibiting, or treating the progression or onset of hyperglycemia comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of obesity comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In one embodiment, the present invention relates to a method for preventing, inhibiting, or treating the progression or onset of dyslipidemia comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of hypertension comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of cognitive impairment comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to the use of a compound of the present invention in the preparation of a medicament that may be used for inhibiting the activity of the enzyme 11-beta-hydroxysteroid dehydrogenase type I comprising administering to a mammalian patient, for example, a human patient, in need thereof a therapeutically effective amount of a compound of the present invention, alone, or optionally, in combination with another compound of the present invention and/or at least one other type of therapeutic agent.

In another embodiment, the present invention relates to the use of a compound of the present invention in the preparation of a medicament that may be used for preventing, inhibiting, or treating the progression or onset of diseases or disorders associated with the activity of the enzyme 11-beta-hydroxysteroid dehydrogenase type I comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to the use of a compound of the present invention in the preparation of a medicament that may be used for preventing, inhibiting, or treating the progression or onset of diabetes, hyperglycemia, obesity, dyslipidemia, hypertension and cognitive impairment comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In still another embodiment, the present invention relates to the use of a compound of the present invention in the preparation of a medicament that may be used for preventing, inhibiting, or treating the progression or onset of diabetes, comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In yet still another embodiment, the present invention relates to the use of a compound of the present invention in the preparation of a medicament that may be used for preventing, inhibiting, or treating the progression or onset of hyperglycemia comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to the use of a compound of the present invention in the preparation of a medicament that may be used for preventing, inhibiting, or treating the progression or onset of obesity comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In one embodiment, the present invention relates to the use of a compound of the present invention in the preparation of a medicament that may be used for preventing, inhibiting, or treating the progression or onset of dyslipidemia comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to the use of a compound of the present invention in the preparation of a medicament that may be used for preventing, inhibiting, or treating the progression or onset of hypertension comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to the use of a compound of the present invention in the preparation of a medicament that may be used for preventing, inhibiting, or treating the progression or onset of cognitive impairment comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for treating a metabolic disorder.

In another embodiment, the present invention also provides the use of a compound of the present invention for the manufacture of a medicament for the treatment of a metabolic disorder.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment of a metabolic disorder.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of a metabolic disorder.

In another preferred embodiment, the present invention provides a novel article of manufacture, further comprising: (d) a second container;

wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat a metabolic disorder.

In another preferred embodiment, the present invention provides a novel article of manufacture, further comprising: (d) a second container;

wherein components (a) and (b) are located within the second container and component (c) is located within or outside of the second container.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Young, S. D. et al., *Antimicrobial Agents and Chemotherapy*, 2602-2605 (1995).

To the extent that compounds of the formula I, and salts thereof, may exist in their tautomeric form, all such tautomeric forms are contemplated herein as part of the present invention.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, including monocyclic alkyl, bicyclic alkyl (or bicycloalkyl) and tricyclic alkyl, containing a total of 3 to 20 carbons forming the ring, preferably 3 to 15 carbons, more preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl,

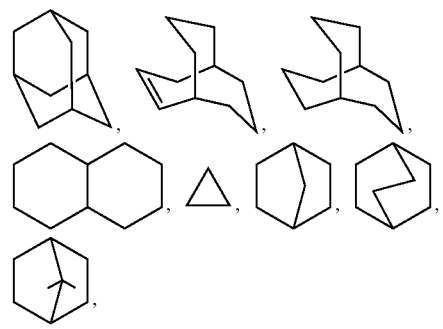

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings
for example

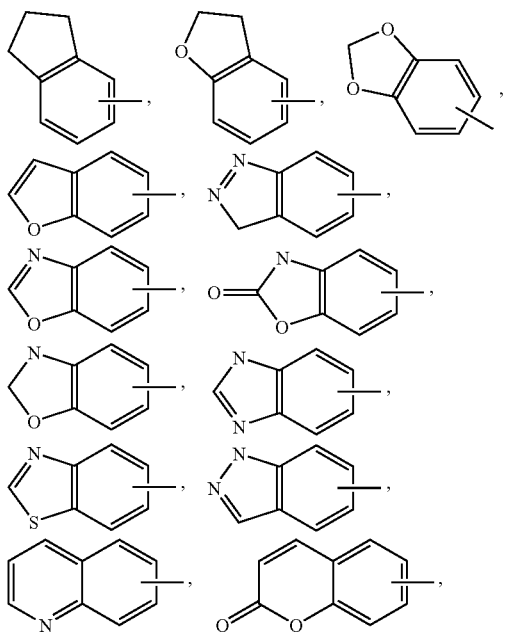

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl or 4-diarylalkyl-1-piperazinyl, all of which may be optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 4- to 14-membered monocyclic, bicyclic or tricyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and Spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO$_2$ group.

The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmidic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch. 31 (Academic Press, 1996);

b) *Design of Prodrugs*, edited by H. Bundgaard (Elsevier, 1985);

c) *A Textbook of Drug Design and Development*, P. Krogsgaard-Larson and H. Bundgaard, eds., Ch. 5, pp. 113-191 (Harwood Academic Publishers, 1991); and d) *Hydrolysis in Drug and Prodrug Metabolism*, Bernard Testa and Joachim M. Mayer (Wiley-VCH, 2003).

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit 11-beta-HSD1 or effective to treat or prevent metabolic disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

Synthesis

Compounds of formula I may be prepared as shown in the following reaction schemes and description thereof, as well as relevant literature procedures that may be used by one skilled in the art. Exemplary reagents and procedures for these reactions appear hereinafter and in the working examples set forth below.

Scheme I

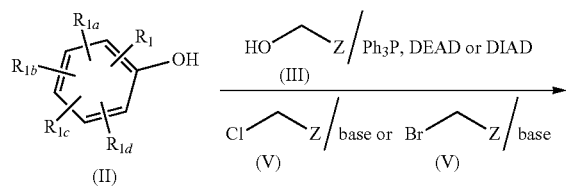

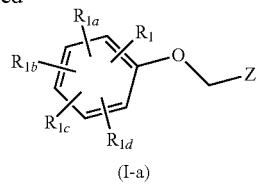

Scheme I describes a method for preparing compounds of formula I-a (a subset of compounds of formula I). A phenol intermediate II can be obtained commercially, prepared by methods known in the literature or by other methods known to one skilled in the art. Formation of a compound I-a can be carried out from a phenol II and an alcohol III using triphenylphosphine and DEAD or DIAD, commonly known as the Mitsunobu Reaction. Alternatively, a compound I-a can be obtained from alkylation of a phenol II with a chloride IV or a bromide V in the presence of an appropriate base, such as sodium carbonate or DIEA.

Scheme II

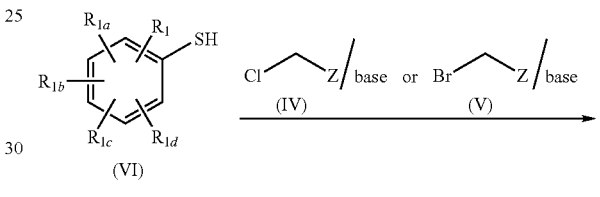

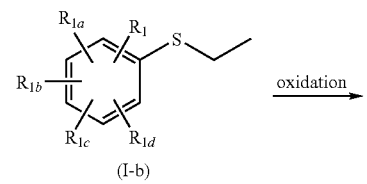

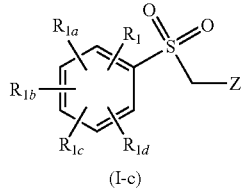

Scheme II describes a method for preparing compounds of formula I-b and formula I-c (subsets of compounds of formula I). A thiophenol intermediate VI can be obtained commercially, prepared by methods known in the literature or by other methods known to one skilled in the art. Formation of a compound I-b can be obtained from alkylation of a thiophenol VI with a chloride IV or a bromide V in the presence of an appropriate base, such as sodium carbonate or DIEA. Subsequent oxidation of a compound I-b with an appropriate oxidizing reagent such as mCPBA, Oxone®, p-toluenesulfonic peracid generated in situ (*Tetrahedron*, 52:5773-5787 (1996)) or by other reagents known to one skilled in the art provides a compound I-c.

Scheme III

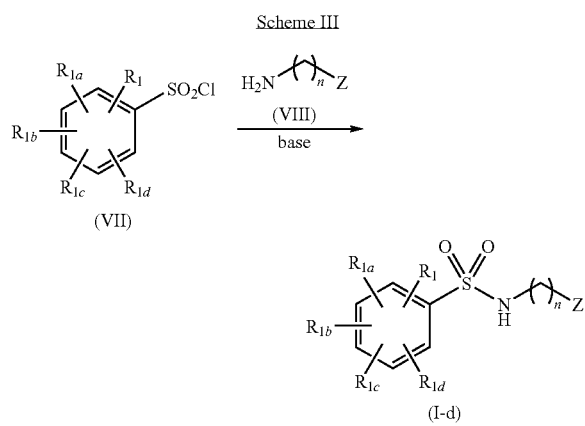

Scheme III describes a method for preparing compounds of formula I-d (a subset of compounds of formula I). An arylsulfonyl chloride intermediate VII can be obtained commercially, prepared by methods known in the literature or by other methods known to one skilled in the art. Formation of a compound I-d can be achieved from the reaction of a compound of formula VII with an amine VIII in the presence of an appropriate base such as pyridine, DIEA or other reagents known to one skilled in the art to provide a compound I-d.

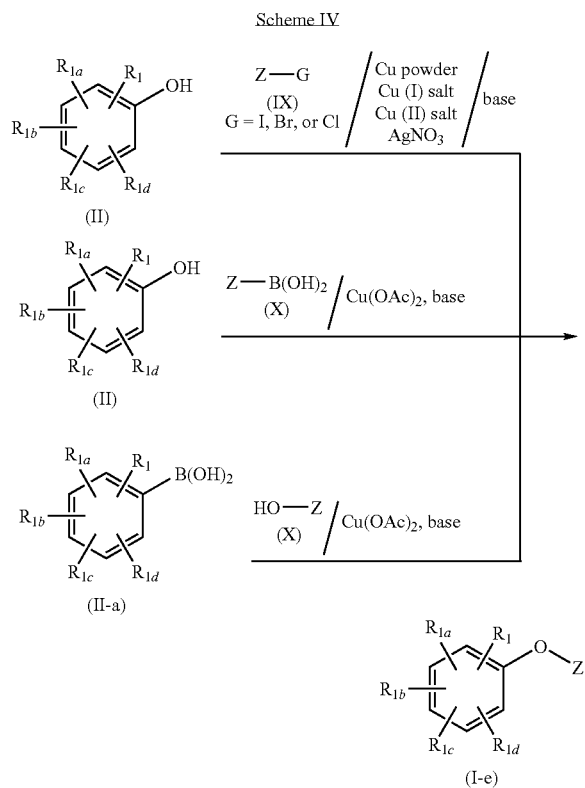

Scheme IV describes a method for preparing compounds of formula I-e (a subset of compounds of formula I). A phenol intermediate II can be obtained commercially, prepared by methods known in the literature or by other methods known to one skilled in the art. Formation of a compound I-e can be achieved from treatment of a potassium salt of a phenol II and a chloro, bromo- or iodo-substituted intermediate IX (G is Cl, Br or I) in the presence of copper powder, copper (I) salt or copper (II) salt at elevated temperature, commonly known as Ullmann ether synthesis (*Tetrahedron*, 40:1433-1456 (1984)). The reactions can be carried out under a conventional procedure or done in a microwave reactor. Alternatively, a compound I-e can be obtained via coupling reaction of a phenol II and a bromo-, chloro- and iodo-substituted intermediate IX (G is Br, Cl or I) in the presence of silver nitrate and a base such as potassium hydroxide at elevated temperature (*Syn. Comm.*, 32:813-817 (2002)). Furthermore, a compound I-e can be obtained from a copper acetate-mediated aryl ether synthesis using a phenol II and an arylboronic acid X or a phenol XI and an arylboronic acid II-a (*Tetrahedron Lett.*, 39:2937-2940 (1998)).

Scheme V

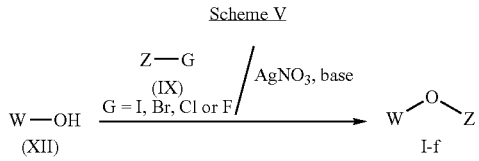

Scheme V describes a method for preparing compounds of formula I-f (a subset of compounds of formula I). A hydroxyl intermediate XII can be obtained commercially, prepared by methods known in the literature or by other methods known to one skilled in the art. Compound I-f can be obtained via coupling reaction of a hydroxyl XII and a bromo-, and chloro- or iodo-substituted intermediate IX (G is Br, Cl, I) in the presence of silver nitrate and a base such as potassium hydroxide at elevated temperature. The reactions can be carried out under a conventional procedure or done in a microwave reactor.

Scheme VI

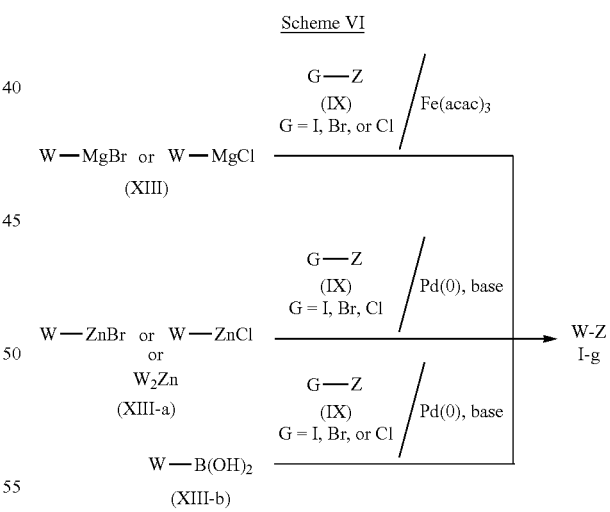

Scheme VI describes a method for preparing compounds of formula I-g (a subset of compounds of formula I). An intermediate XIII, or XIII-a, or XIII-b can be obtained commercially, prepared by methods known in the literature or by other methods known to one skilled in the art. Formation of a compound I-g can be achieved from treatment of a Grignard reagent XIII and a chloro, bromo- or iodo-substituted intermediate IX (G is Cl, Br or I) in the presence of iron acetylacetonate (*Organic Lett.*, 7(11):2169 (2005)). Alternatively, a compound I-g can be obtained via coupling reaction of an organo zinc halide or organo zinc XIII-a with a bromo-, chloro- or iodo-substituted intermediate IX (G is Br, Cl, I) in the presence of a palladium catalyst and a base such as potassium carbonate at elevated temperature. The reactions can be carried out under a conventional procedure or done in a microwave reactor. Furthermore, a compound I-g can be obtained from a palladium-mediated C—C coupling reaction using a non-aryl boronic acid XIII-b and a bromo-, chloro- or iodo-substituted intermediate IX (G is Br, Cl, I) in the presence of palladium catalyst and a base such as potassium carbonate at elevated temperature, commonly known as the Suzuki or modified Suzuki reaction (*J. Organomet. Chem.*, 576:147-168 (1999)).

Scheme VII

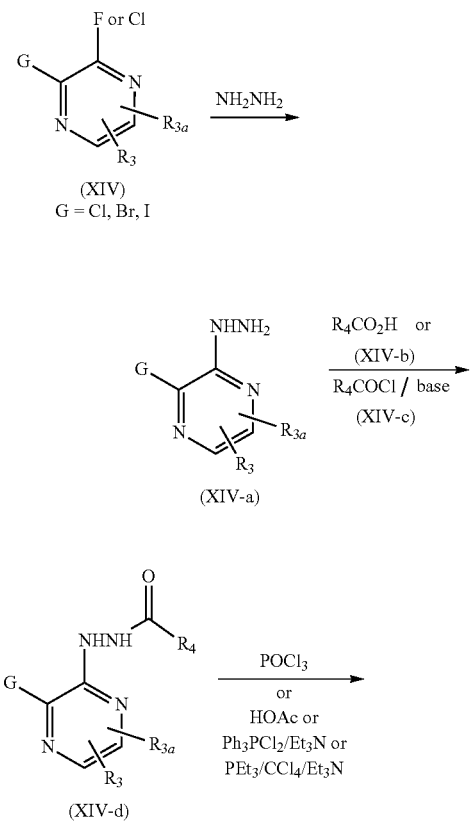

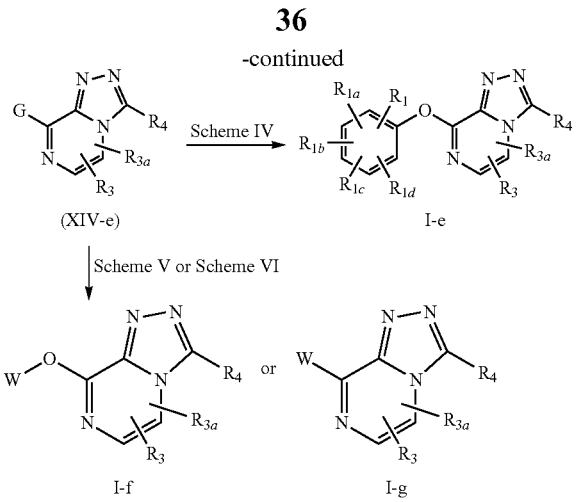

Scheme VII describes a method for preparing compounds of formula I-e, I-f and I-g (subsets of compounds of formula I where Z is a triazolopyrazine group). A chloro- or fluoropyrazine intermediate XIV can be obtained commercially, prepared by methods known in the literature or by other methods known to one skilled in the art. Reaction of a compound of formula XIV with hydrazine can be carried out at elevated temperature to provide an intermediate XIV-a. Acylation of an intermediate XIV-a with an acid XIV-b using an appropriate set of amide coupling reagents such NMM/isobutylchloroformate, EDAC/HOBT or other reagents described in *The Practice of Peptide Synthesis*, $2^{nd}$ Ed., Spring-Verlag, Bodanszy, Miklos (1993) provides a hydrazide intermediate XIV-d. Alternatively, an acyl hydrazide XIV-d can be prepared from the reaction of a compound of formula XIV-a and an acid chloride XIV-c in the presence of an appropriate base such as DIEA or TEA. Formation of triazolopyrazine XIV-e can be achieved from the reaction of XIV-d with POCl$_3$ at an elevated temperature. Formation of triazolopyrazine XIV-e can also be achieved from XIV-d in the presence of acetic acid at an elevated temperature, either under a conventional procedure or a microwave reactor. Alternatively, formation of triazolopyrazine XIV-e can be achieved from the reaction of XIV-d with Ph$_3$PCl$_2$ in the presence of a base such as TEA or by P(alkyl)$_3$/CCl$_4$ in the presence of a base such as TEA or DIPEA, or other methods known to one skilled in the art. Formation of a compound of formula I-e, I-f and I-g can be achieved using reactions described in Schemes IV to VI or by other methods known to one skilled in the art.

Scheme VIII

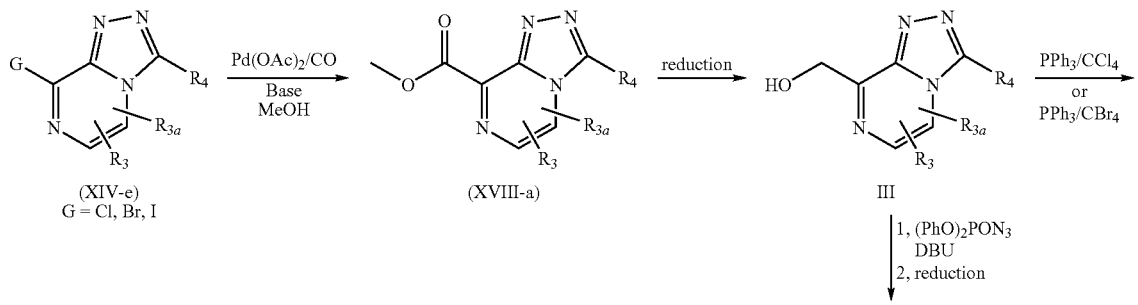

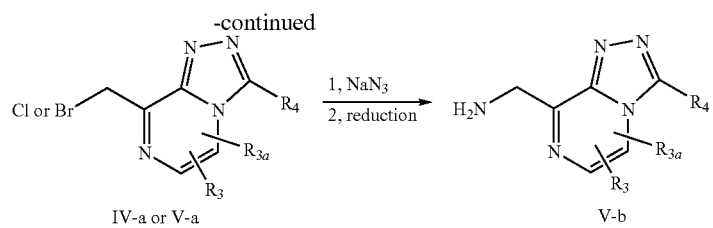

IV-a or V-a → V-b

Scheme VIII describes a method for preparing compounds of formula XVIII-a, III, IV-a, V-a or V-b. An intermediate XVIII-a can be obtained by carboxylation of XIV-e in the presence of a palladium catalyst and carbon monooxide, or prepared by methods known in the literature or by other methods known to one skilled in the art. Reduction of the carbonyl group to an alcohol to generate compound III can be performed by a reducing reagent such as $NaBH_4$, or other reducing reagent such as DIBAL or by methods known in the literature or by other methods known to one skilled in the art. Formation of a compound IV-a or V-a can be achieved by reaction of a compound III with $PPh_3/CCl_4$ or $PPh_3/CBr_4$ in the presence of a base such as TEA, or prepared by methods known in the literature or by other methods known to one skilled in the art. Formation of amine V-b can be achieved by a transformation of III or IV-a or V-a, both methods known in the literature or by other methods known to one skilled in the art.

prepared by methods known in the literature or by other methods known to one skilled in the art. Reaction of a compound of formula XV with hydrazine was carried out at elevated temperature to provide an intermediate XV-a. Acylation of intermediate XV-a with acid XV-b using an appropriate set of amide coupling reagents such NMM/isobutyl-chloformate, EDAC/HOBT or other reagents described in *The Practice of Peptide Synthesis*, $2^{nd}$ Ed., Spring-Verlag, Bodanszy, Miklos (1993) provides a hydrazide intermediate XV-d. Alternatively, the acyl hydrazide XV-d can be prepared from the reaction of a compound of formula XV-a and an acid chloride XV-c in the presence of an appropriate base such as DIEA or TEA. Formation of triazolopyrimidine XV-e (or I-h) can be achieved from the reaction of XV-d with $POCl_3$ at an elevated temperature. Formation of triazolopyrimidine XV-e (or I-h) can also be achieved from XV-d in the presence of acetic acid at an elevated temperature, either under a conventional procedure or a microwave reactor. Alternatively, for-

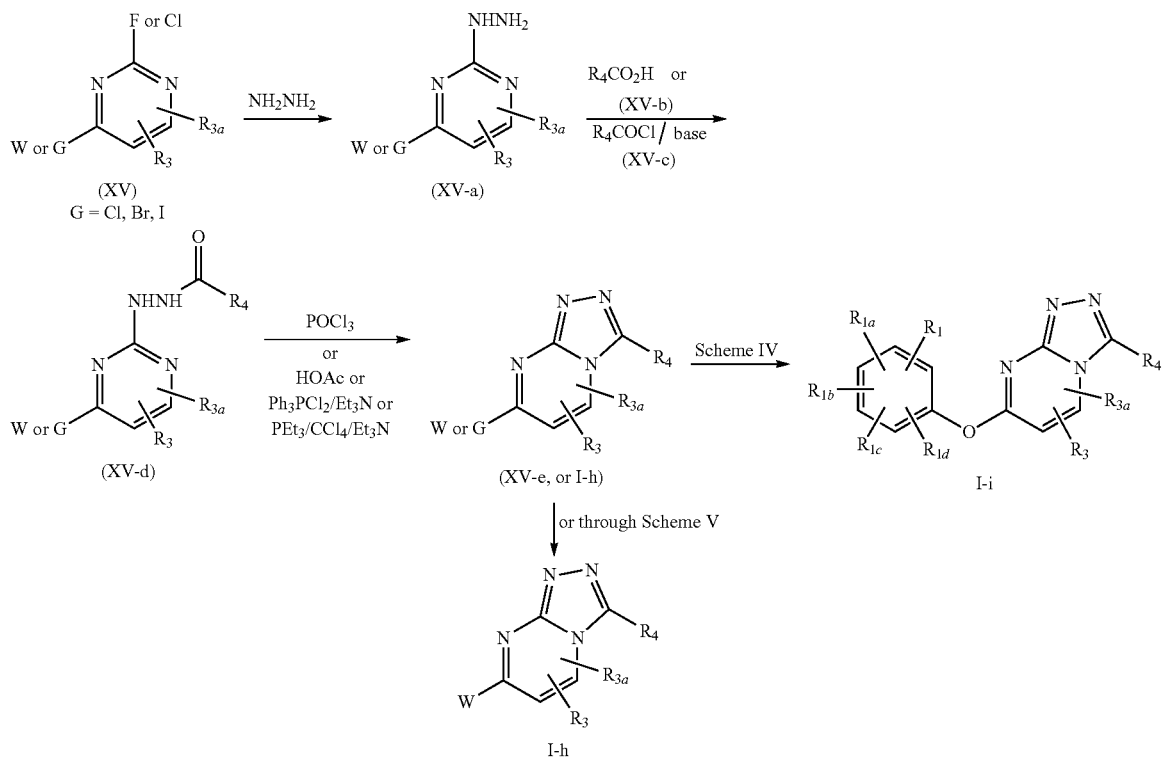

Scheme IX

Scheme IX describes a method for preparing compounds of formula I-i and I-h (subsets of compounds of formula I where Z is a triazolopyrimidine group). A chloro- or fluoro-pyrimidine intermediate XV can be obtained commercially, mation of triazolopyrimidine XV-e (or I-h) can be achieved from the reaction of XV-d with $Ph_3PCl_2$ in the presence of a base such as TEA or by $P(alkyl)_3/CCl_4$ in the presence of a base such as TEA or DIPEA, or other methods known to one skilled in the art. Formation of a compound of formula I-i and I-h can be achieved using reactions described in Schemes IV to VI or by other methods known to one skilled in the art.

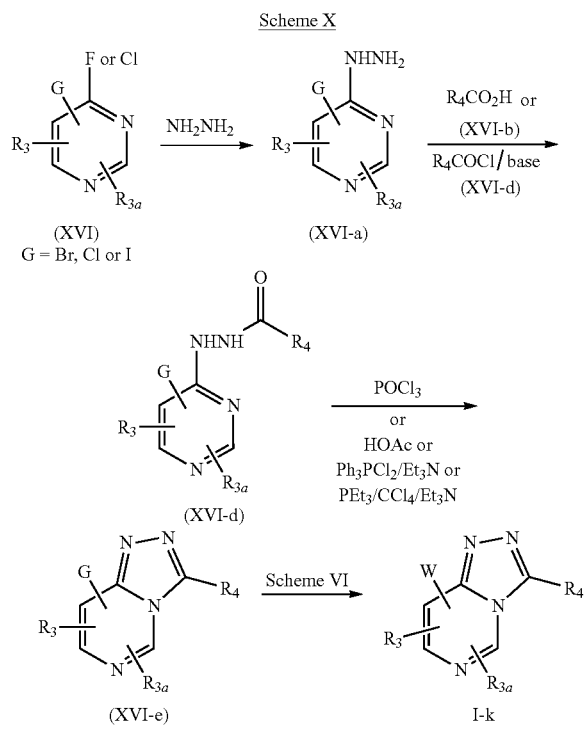

Scheme X

Scheme X describes a method for preparing compounds of formula I-k (a subset of compounds of formula I where Z is a triazolopyrimidine group). A chloro- or fluoropyrimidine intermediate XVI can be obtained commercially, prepared by methods known in the literature or by other methods known to one skilled in the art. Reaction of a compound of formula XVI with hydrazine was carried out at elevated temperature to provide an intermediate XVI-a. Acylation of intermediate XVI-a with an acid XVI-b using an appropriate set of amide coupling reagents such NMM/isobutylchloformate, EDAC/HOBT or other reagents described in *The Practice of Peptide Synthesis*, $2^{nd}$ Ed., Spring-Verlag, Bodanszy, Miklos (1993) provides an acyl hydrazide intermediate XVI-d. Alternatively, hydrazide XVI-d can be prepared from the reaction of a compound of formula XVI-a and an acid chloride XVI-c in the presence of an appropriate base such as DIEA or TEA. Formation of triazolopyrimidine XVI-e can be achieved from the reaction of XVI-d with $POCl_3$ at an elevated temperature. Formation of triazolopyrimidine XVI-e can also be achieved from XVI-d in the presence of acetic acid at an elevated temperature, either under a conventional procedure or a microwave reactor. Alternatively, formation of triazolopyrazine XVI-e can be achieved from the reaction of XVI-d with $Ph_3PCl_2$ in the presence of a base such as TEA or by $P(alkyl)_3/CCl_4$ in the presence of a base such as TEA or DIPEA, or other methods known to one skilled in the art. Formation of a compound of formula I-k can be achieved using reactions described in Scheme VI or by other methods known to one skilled in the art.

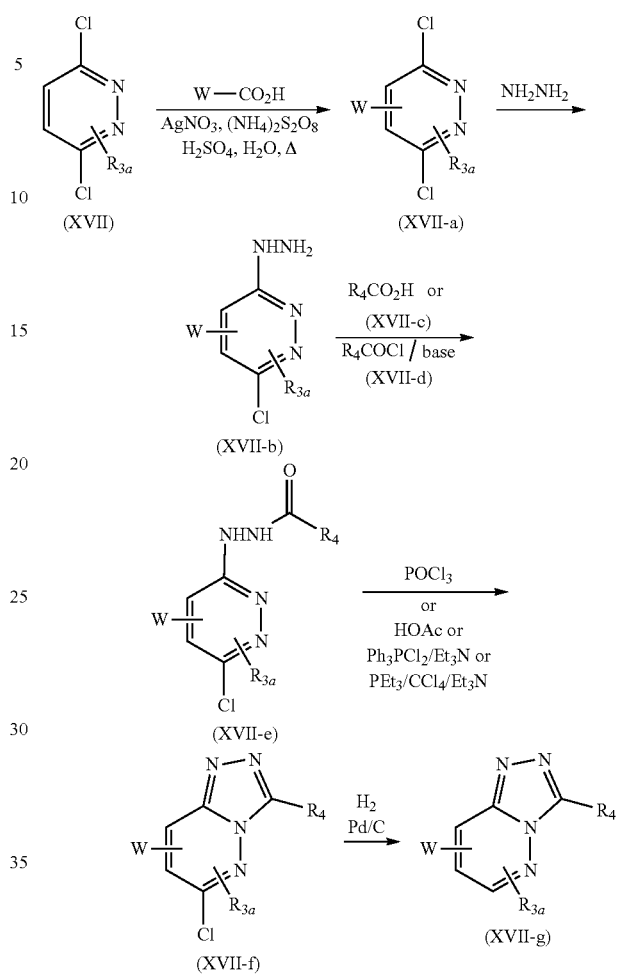

Scheme XI

Scheme XI describes a method for preparing compounds of formula XVII-g (a subset of compounds of formula I where Z is a triazolopyridazine group). A dichloropyridazine intermediate XVII, obtained commercially or prepared by methods known in the literature or by other methods known to one skilled in the art, can be converted to the substituted analog XVII-a under Minisci reaction conditions as described by Samaritoni and Babbitt (*J. Het. Chem.*, 28:583 (1991)). Reaction of a compound of formula XVII-a with hydrazine can be carried out at elevated temperature to provide an intermediate XVII-b. Acylation of an intermediate XVII-b with an acid XVII-c using an appropriate set of amide coupling reagents such NMM/isobutylchloformate, EDAC/HOBT or other reagents described in *The Practice of Peptide Synthesis*, $2^{nd}$ Ed., Spring-Verlag, Bodanszy, Miklos (1993) provides a hydrazide intermediate XVII-e. Alternatively, an acyl hydrazide XVII-e can be prepared from the reaction of a compound of formula XVII-b and an acid chloride XVII-d in the presence of an appropriate base such as DIEA or TEA. Formation of triazolopyridazine XVII-f can be achieved from the reaction of XVII-e with $POCl_3$ at an elevated temperature. Formation of triazolopyridazine XVII-f can also be achieved from XVII-e in the presence of acetic acid at an elevated temperature, either under a conventional procedure or a microwave reactor. Alternatively, formation of triazolopyridazine XVII-f can be achieved from the reaction of XVII-e with Ph$_3$PCl$_2$ in the presence of a base such as TEA or by P(alkyl)$_3$/CCl$_4$ in the presence of a base such as TEA or DIPEA, or other methods known to one skilled in the art. Dechlorination of XVII-e to yield XVII-g can be accomplished under hydrogenolytic conditions in the presence of catalytic palladium on carbon in solvents such as methanol, ethyl acetate, tetrahydrofuran, methylene chloride, or by other methods known to one skilled in the art.

Scheme XII

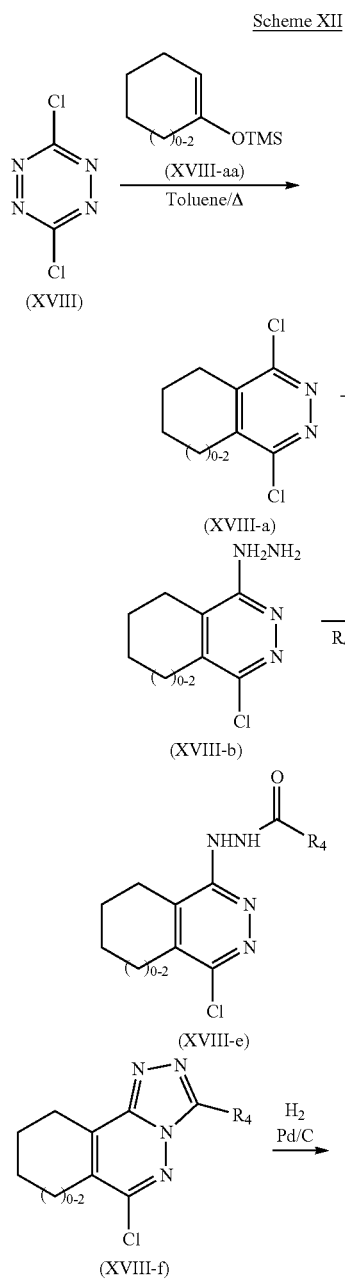

(1998)). Reaction of a compound of formula XVIII-a with hydrazine can be carried out at elevated temperature to provide an intermediate XVIII-b. Acylation of an intermediate XVIII-b with an acid XVIII-c using an appropriate set of amide coupling reagents such NMM/isobutylchloformate, EDAC/HOBT or other reagents described in *The Practice of Peptide Synthesis*, 2$^{nd}$ Ed., Spring-Verlag, Bodanszy, Miklos (1993) provides a hydrazide intermediate XVIII-e. Alternatively, an acyl hydrazide XVIII-e can be prepared from the reaction of a compound of formula XVIII-b and an acid chloride XVIII-d in the presence of an appropriate base such as DIEA or TEA. Formation of triazolopyridazine XVIII-f can be achieved from the reaction of XVIII-e with POCl$_3$ at an elevated temperature. Formation of triazolopyridazine XVIII-f can also be achieved from XVIII-e in the presence of acetic acid at an elevated temperature, either under a conventional procedure or a microwave reactor. Alternatively, formation of triazolopyridazine XVIII-f can be achieved from the reaction of XVIII-e with Ph$_3$PCl$_2$ in the presence of a base such as TEA or by P(alkyl)$_3$/CCl$_4$ in the presence of a base such as TEA or DIPEA, or other methods known to one skilled in the art. Dechlorination of XVIII-f to yield XVIII-g can be accomplished under hydrogenolytic conditions in the presence of catalytic palladium on carbon in solvents such as methanol, ethyl acetate, tetrahydrofuran, methylene chloride, or by other methods known to one skilled in the art.

Scheme XIII

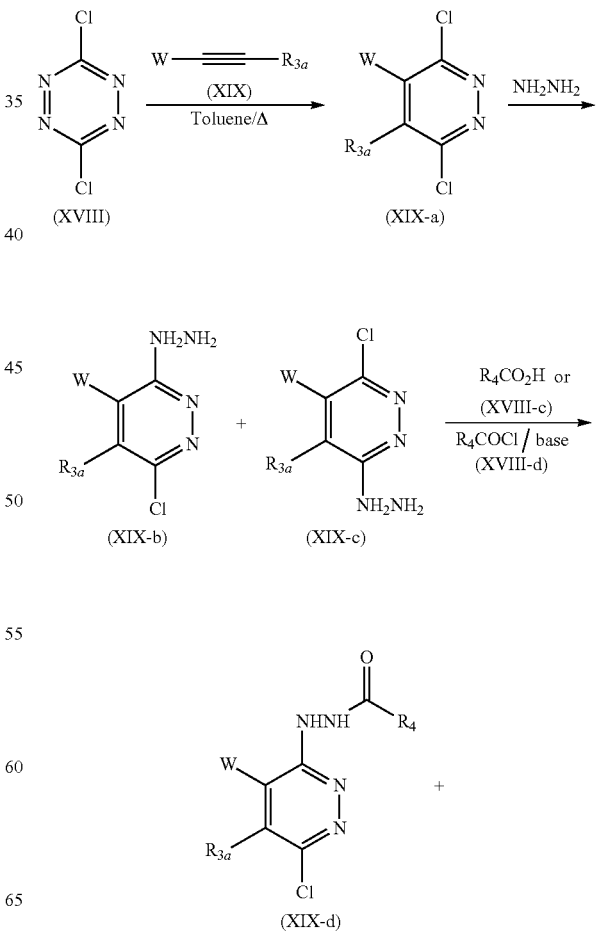

Scheme XII describes a method for preparing compounds of formula XVIII-g (a subset of compounds of formula I where Z is a triazolopyridazine group). Dichlorotetrazine XVIII can be converted to dichloropyridazines such as XVIII-a by reaction with cyclic trimethylsilyl enol ethers such as XVIII-aa in toluene at reflux using the procedure described by Sparey and Harrison (*Tet. Lett.*, 39:5873

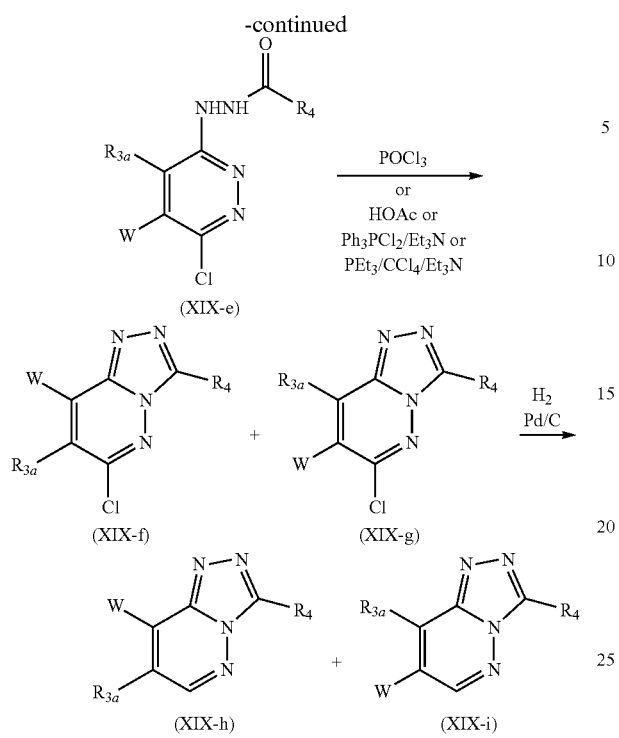

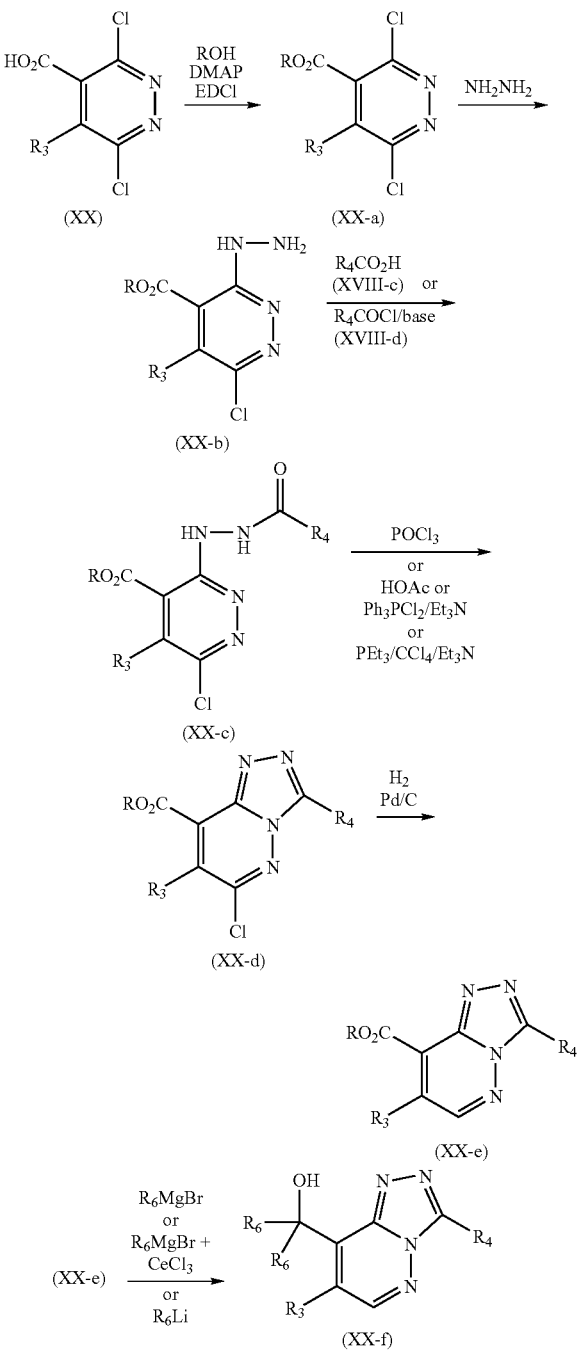

Scheme XIII describes a method for preparing compounds of formula XIX-h and XIX-i (a subset of compounds of formula I where Z is a triazolopyridazine group). Dichlorotetrazine XVIII can be converted to dichloropyridazines such as XIX-a by reaction with alkynes such as XIX in toluene at reflux using the procedure described by Sparey and Harrison (*Tet. Lett.*, 39:5873 (1998)). Reaction of a compound of formula XIX-a with hydrazine was carried out at elevated temperature to provide a mixture of regioisomeric intermediates XIX-b and XIX-c. Acylation of intermediates XIX-b and XIX-c with an acid XVIII-c using an appropriate set of amide coupling reagents such NMM/isobutylchloformate, EDAC/HOBT or other reagents described in *The Practice of Peptide Synthesis*, 2$^{nd}$ Ed., Spring-Verlag, Bodanszy, Miklos (1993) provides hydrazide regioisomeric intermediates XIX-d and XIX-e. Alternatively, acyl hydrazide XIX-d and XIX-e can be prepared from the reaction of a compounds of formula XIX-b and XIX-c and an acid chloride XVIII-d in the presence of an appropriate base such as DIEA or TEA. Formation of triazolopyridazines of formula XIX-f and XIX-g can be achieved from the reaction of compounds of formula XIX-d and XIX-e with POCl$_3$ at an elevated temperature. Formation of triazolopyridazines XIX-f and XIX-g can also be achieved from XIX-d and XIX-e in the presence of acetic acid at an elevated temperature, either under a conventional procedure or a microwave reactor. Alternatively, formation of triazolopyridazines XIX-f and XIX-g can be achieved from the reaction of XIX-d and XIX-e with Ph$_3$PCl$_2$ in the presence of a base such as TEA or by P(alkyl)$_3$/CCl$_4$ in the presence of a base such as TEA or DIPEA, or other methods known to one skilled in the art. Dechlorination of XIX-f and XIX-g to yield XIX-h and XIX-i can be accomplished under hydrogenolytic conditions in the presence of catalytic palladium on carbon in solvents such as methanol, ethyl acetate, tetrahydrofuran, methylene chloride, or by other methods known to one skilled in the art. Separation of the reioisomeric intermediates or products may be carried out at any stage depending on the relative ease of chromatographic purification by methods known to one skilled in the art.

Scheme XIV describes a method for preparing compounds of formula XX-f (a subset of compounds of formula I where Z is a triazolopyridazine group). Dichloropyridazine carboxylic acid XX may be converted to the ester XX-a using an alcohol, DMAP, and EDCI (EDAC), or by other acylation condition known to one skilled in the art. Reaction of a compound of formula XX-a with hydrazine was carried out at room temperature or elevated temperature to provide an intermediate XX-b. Acylation of an intermediate XX-b with an acid XVIII-c using an appropriate set of amide coupling reagents such NMM/isobutylchloformate, EDAC/HOBT or other reagents described in *The Practice of Peptide Synthesis, 2nd* Ed., Spring-Verlag, Bodanszy, Miklos (1993) provides a hydrazide intermediate XX-c. Alternatively, an acyl hydrazide XX-c can be prepared from the reaction of a compound of formula XX-b and an acid chloride XVIII-d in the presence of an appropriate base such as DIEA or TEA. Formation of triazolopyridazine XX-d can be achieved from the reaction of XX-c with $POCl_3$ at an elevated temperature. Formation of triazolopyridazine XX-d can also be achieved from XX-c in the presence of acetic acid at an elevated temperature, either under a conventional procedure or a microwave reactor. Alternatively, formation of triazolopyridazine XX-d can be achieved from the reaction of XX-c with $Ph_3PCl_2$ in the presence of a base such as TEA or by $P(alkyl)_3/CCl_4$ in the presence of a base such as TEA or DIPEA, or other methods known to one skilled in the art. Dechlorination of XX-d to yield XX-e can be accomplished under hydrogenolytic conditions in the presence of catalytic palladium on carbon in solvents such as methanol, ethyl acetate, tetrahydrofuran, methylene chloride, or by other methods known to one skilled in the art. Compound XX-e can be converted to carbinol XX-f by the use of two equivalents of a Grignard reagent, a Grignard reagent plus cerium trichloride, or a lithium reagent using methods known to one skilled in the art.

reagent plus cerium trichloride, or a lithium reagent to give compound XXI-e. Compound XXI-e can also be produced by the reaction of compound IX with butyllithium or a lithium/naphthalene mixture (to generate the intermediate organomagnesium halide or organolithium) followed by reaction with a ketone XXI-d as described by Wang et al. (*Tet. Lett.*, 41:4335 (2000)) or by using methods known to one skilled in the art.

EXAMPLES

The following working Examples serve to better illustrate, but not limit, some of the preferred embodiments of the present invention.

General

The term HPLC refers to a Shimadzu high performance liquid chromatography with one of following methods:

Method A: Phenomenex C18 5 micron 4.6×50 mm column using a 4 minute gradient of 0-100% solvent B [90% MeOH:10% $H_2O$:0.2% $H_3PO_4$] and 100-0% solvent A [10% MeOH:90% $H_2O$:0.2% $H_3PO_4$] with 4 mL/min flow rate and a 1 min. hold, an ultra violet (UV) detector set at 220 nm.

Method B: Phenomenex S5 ODS 4.6×30 mm column, gradient elution 0-100% B/A over 2 min (solvent A=10%

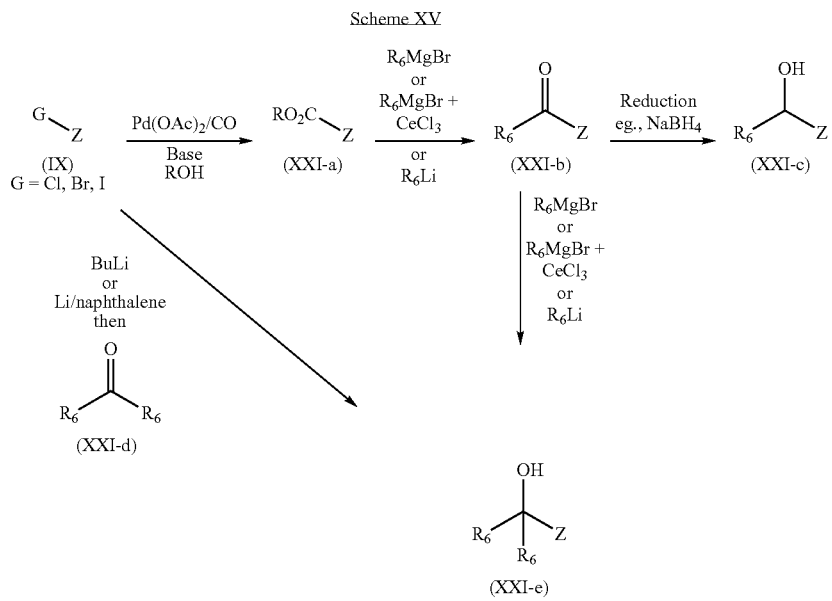

Scheme XV

Scheme XV describes a method for preparing compounds of formula XXI-b, XXI-c and XXI-e. A compound represented by IX, where Z is defined as previously described in the Claims and G=Cl, Br, or I, can be carbonylated using an appropriate catalyst such as palladium acetate under an atmosphere of carbon monoxide in the presence of a suitable base such as potassium carbonate when conducted in an alcoholic solvent to provide ester XXI-a. Compound XXI-a can be converted to carbonyl compound XXI-b by the use of one equivalent of a Grignard reagent, a Grignard reagent plus cerium trichloride, or a lithium reagent using methods known to one skilled in the art. Compound XXI-b can be converted to carbinol XXI-c by reduction with an appropriate reagent such as sodium borohydride. Compound XXI-b can be reacted with a second equivalent of a Grignard reagent, a Grignard MeOH/$H_2O$ containing 0.1% TFA, solvent B=90% MeOH/$H_2O$ containing 0.1% TFA), flow rate 5 mL/min, UV detection at 220 nm.

Method C: YMC S7 ODS 3.0×50 mm column, gradient elution 0-100% B/A over 2 min (solvent A=10% MeOH/$H_2O$ containing 0.1% TFA, solvent B=90% MeOH/$H_2O$ containing 0.1% TFA), flow rate 5 mL/min, UV detection at 220 nm.

Method D: YMC S-5 C18 5 micron 4.6×50 mm column using a 4 minute gradient of 0-100% solvent B [90% $CH_3CN$:10% $H_2O$:0.1% TFA] and 100-0% solvent A [10% $CH_3CN$:90% $H_2O$:0.1% TFA] with 4 mL/min flow rate and a 1 min. hold (100% B), an ultra violet (UV) detector set at 220 nm.

The term prep HPLC refers to an automated Shimadzu HPLC system using a mixture of solvent A (10% MeOH/90% $H_2O$/0.1% TFA) and solvent B (90% MeOH/10% $H_2O$/0.1%

TFA) or a mixture of solvent A (10% CH₃CN/90% H₂O/0.1% TFA) and solvent B (90% CH₃CN/10% H₂O/0.1% TFA). The preparative columns were packed with YMC or Phenomenex ODS C18 5 micron resin or equivalent.

ABBREVIATIONS

The following abbreviations are employed in the Examples and elsewhere herein:
Ph=phenyl
Bn=benzyl
i-Bu=iso-butyl
Me=methyl
Et=ethyl
Pr=propyl
Bu=butyl
AIBN=2,2'-Azobisisobutyronitrile
Boc or BOC=tert-butoxycarbonyl
Cbz=carbobenzyloxy or carbobenzoxy or benzyloxycarbonyl
DCM=dichloromethane
DEAD=Diethyl azodicarboxylate
DIAD=Diisopropyl azodicarboxylate
DIEA=N,N-diisopropylethylamine
DIPEA=Diisopropylethylamine
DMA=N,N-dimethylacetylamide
DMF=N,N-dimethylformamide
DMSO=dimethylsulfoxide
EtOAc=ethyl acetate
EDAC=3-ethyl-3'-(dimethylamino)propyl-carbodiimide hydrochloride (or 1-[(3-(dimethyl)amino)propyl])-3-ethylcarbodiimide hydrochloride); EDCl
FMOC=fluorenylmethoxycarbonyl
HOAc or AcOH=acetic acid
HOAT=1-hydroxy-7-azabenzotriazole
HOBT=1-hydroxybenzotriazole
LAH=lithium aluminum hydride
mCPBA=3-Chloroperoxybenzoic acid
NMM=N-methyl morpholine
NBS=N-Bromosuccinimide
n-BuLi=n-butyllithium
Oxone®=Monopersulfate
Pd/C=palladium on carbon
PtO₂=platinum oxide
PyBOP reagent=benzotriazol-1-yloxy-tripyrrolidino phosphonium hexafluorophosphate
Pd(dppf)Cl₂—CH₂Cl₂=1,1'-Bis(diphenylphosphino)ferrocene-palladium(II)dichloride dichloromethane complex
SOCl₂=Thionyl chloride
TBAF=tetrabutylammonium fluoride
TBS=tert-Butyldimethylsilyl
TMS=trimethylsilyl
TEA=triethylamine
TFA=trifluoroacetic acid
THF=tetrahydrofuran
equiv=equivalent(s)
min=minute(s)
h or hr=hour(s)
L=liter
mL=milliliter
μL=microliter
g=gram(s)
mg=milligram(s)
mol=mole(s)
mmol=millimole(s)
meq=milliequivalent
RT=room temperature
sat or sat'd=saturated
aq.=aqueous
TLC=thin layer chromatography
HPLC=high performance liquid chromatography
HPLC R_t=HPLC retention time
LC/MS=high performance liquid chromatography/mass spectrometry
MS or Mass Spec=mass spectrometry
NMR=nuclear magnetic resonance
mp=melting point Example 1

3-(2-(4-Chlorophenyl)propan-2-yl)-8-cyclopropyl-[1,2,4]triazolo[4,3-a]pyrazine

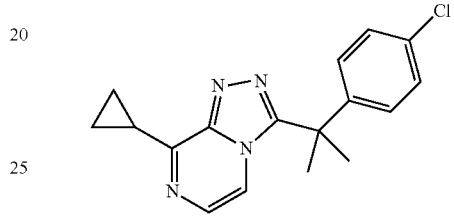

Compound 1A: 2-Chloro-3-hydrazinylpyrazine

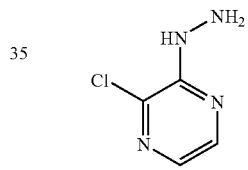

2,3-Dichloropyrazine (25 g) and anhydrous hydrazine (21 ml) were dissolved in pyridine (100 mL) and heated to 60° C. After 3 h, the reaction was concentrated in vacuo to yield a residue. The residue was rinsed with water and the filtered. The resulting solid was collected by filtration and dried at 40° C. in vacuo to afford Compound 1A as a light yellow solid (20.3 g, 88%).

Compound 1B: 2-(4-Chlorophenyl)-N'-(3-chloropyrazine-2-yl)-2-methylpropanehydrazide

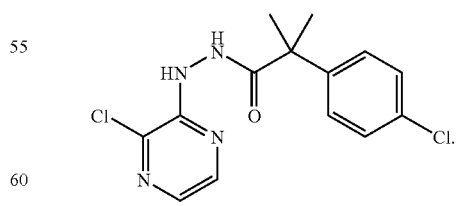

To a 0° C. solution of 2-(4-chlorophenyl)-2-methylpropanoic acid (99.3 mg, 0.50 mmol) in THF (2 mL) was added 4-methylmorpholine (60.5 μL, 0.55 mmol). After 10 minutes, isobutyl chloroformate (67.4 μL, 0.52 mmol) was added dropwise over 2 minutes. After 2.5 h, a solution of Compound 1A (72.3 mg, 0.50 mmol) in THF (3 mL) was added dropwise over 2 minutes. After 10 minutes the cooling bath was removed and the reaction mixture was warmed to room temperature. After 3 h at room temperature, water (5 mL) and ethyl acetate (10 mL) were added, and the resulting mixture was stirred for 10 minutes. At the conclusion of this period, the organic phase was separated, dried over Na$_2$SO$_4$, and then concentrated in vacuo to yield a residue. The residue was purified by flash chromatography (SiO$_2$, 0-100% ethyl acetate/hexanes) to provide compound 1B, which was used directly in the preparation of compound 1C set forth below. LC/MS (m/z)=325 (M+H)$^+$.

Compound 1C: 8-Chloro-3-(2-(4-chlorophenyl)propan-2yl)-1,2,41-triazolo[4,3-a]pyrazine

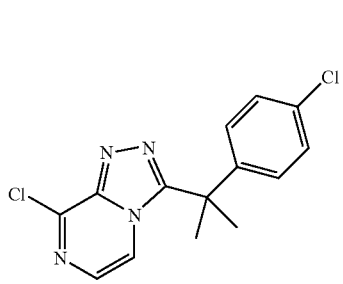 [SMILES: CC(C)(c1ccc(Cl)cc1)c1nnc2c(Cl)nccn12]

Compound 1B was dissolved in THF (3 mL) and CCl$_4$ (2 mL). The resulting solution was cooled to 0° C. Once at the prescribed temperature, DIPEA (697 µL, 4.0 mmol) was added. Triethylphosphine (221 µL, 1.5 mmol) was then added dropwise over a 3 minute period. Upon completion of addition, the reaction was allowed to slowly warm to room temperature where it stirred for 16 h. After 16 h, water (5 mL) and ethyl acetate (5 mL) were added, and the resulting mixture was stirred vigorously for 10 minutes. After this time, the organic phase was separated, dried over Na$_2$SO$_4$, and then concentrated in vacuo to yield a residue. The residue was purified by flash chromatography (SiO$_2$, 0-100% ethyl acetate/hexanes) to provide compound 1C (98.7 mg, 64%). LC/MS (m/z)=307 (M+H)$^+$.

Example 1

Compound 1C (92.2 mg, 0.30 mmol) and Fe(acac)$_3$ (21.2 mg, 0.06 mmol) were dissolved in THF (1.5 mL) and 1-methyl-2-pyrrolidinone (188 µL) and the resulting solution was cooled to 0° C. Once at the prescribed temperature, cyclopropylmagnesium bromide (1.20 mL, 0.60 mmol, 0.5 M solution in THF) was added over a 1 min period. The resulting mixture was stirred for an additional 1 h. After the 1 h, cyclopropylmagnesium bromide (1.20 mL, 0.60 mmol, 0.5 M solution in THF) was added, and the resulting mixture was stirred for 16 h. At the conclusion of this period, additional Fe(acac)$_3$ (21.2 mg, 0.06 mmol) and cyclopropylmagnesium bromide (1.20 mL, 0.60 mmol, 0.5 M solution in THF) were added. Upon completion of addition, the reaction mixture was stirred for an hour, quenched with water and then partitioned between ethyl acetate (10 mL) and water (5 mL). The organic phase was separated, dried over Na$_2$SO$_4$, and then concentrated in vacuo. The resulting residue was purified by flash chromatography (SiO$_2$, 0-100% ethyl acetate/hexanes) to afford Example 1 as an off-white solid (71.5 mg, 76%). HPLC t$_R$ (Method D): 2.29 min (>99% pure). LC/MS (m/z)=313 (M+H)$^+$.

Example 2

3-(1-(4-Chlorophenyl)cyclobutyl)-8-cyclopropyl-[1,2,4]triazolo[4,3-a]pyrazine

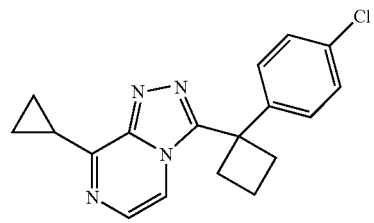 [SMILES: Clc1ccc(C2(c3nnc4c(C5CC5)nccn34)CCC2)cc1]

Compound 2A: 1-(4-Chlorophenyl)-N'-(3-chloropyrazine-2-yl)cyclobutanecarbohydrazide

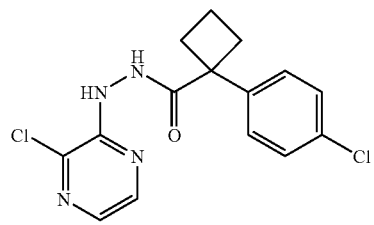 [SMILES: O=C(NNc1nccnc1Cl)C1(c2ccc(Cl)cc2)CCC1]

To a 0° C. solution of 1-(4-chlorophenyl)cyclobutanecarboxylic acid (105.3 mg, 0.50 mmol) in THF (2 mL) was added 4-methylmorpholine (60.5 µL, 0.55 mmol). The reaction mixture was stirred for 10 minutes, and then isobutyl chloroformate (67.4 µL, 0.52 mmol) was added dropwise over a 2 minute period. Upon completion of addition, the reaction mixture was stirred for 1 h. A solution of Compound 1A (72.3 mg, 0.50 mmol) in THF (3 mL) was then added dropwise over a 2 minute period. The resulting mixture was stirred for 10 minutes and then the cooling bath was removed. The reaction mixture was allowed to warm to room temperature where it stirred for 1 h. After this time, water (5 mL) and ethyl acetate (10 mL) were added, and the resulting mixture was stirred for 10 minutes. At the conclusion of this period, the organic phase was separated, dried over Na$_2$SO$_4$, and then concentrated in vacuo. The resulting residue was purified by flash chromatography (SiO$_2$, 0-60% ethyl acetate/hexanes) to afford compound 2A, which was used directly in the preparation of compound 2B set forth below. LC/MS (m/z)=337 (M+H)+.

Compound 2B: 8-Chloro-3-(1-(4-chlorophenyl)cy-clobutyl)-1,2,41-triazolo[4,3-a]pyrazine

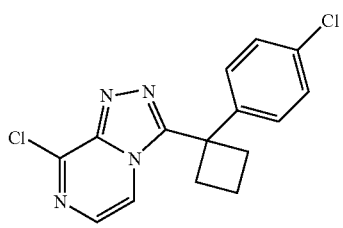 [SMILES: Clc1ccc(C2(c3nnc4c(Cl)nccn34)CCC2)cc1]

Compound 2A was dissolved in THF (3 mL) and CCl$_4$ (2 mL) and the resulting solution was cooled to 0° C. Once at the prescribed temperature, DIPEA (697 μL, 4.0 mmol) was added. Triethylphosphine (221 μL, 1.5 mmol) was then added dropwise over a 3 minute period. The resulting mixture was stirred for 10 minutes, and then the ice-bath was removed. The mixture was stirred for an additional 1 h and then water (5 mL) and ethyl acetate (5 mL) were added. The resulting mixture was stirred vigorously for 10 minutes. After this time, the organic phase was separated, dried over Na$_2$SO$_4$, and then concentrated in vacuo to yield a residue. The residue was purified by flash chromatography (SiO$_2$, 0-60% ethyl acetate/hexanes) to afford compound 2B as an off-white solid (32.6 mg, 20% yield from compound 1A). LC/MS (m/z)=319 (M+H)+.

Example 2

Compound 2B (31.9 mg, 0.10 mmol)) and Fe(acac)$_3$ (7.1 mg, 0.02 mmol) were dissolved in THF (0.5 mL) and 1-methyl-2-pyrrolidinone (62.5 μL). The resulting solution was cooled to 0° C. and then cyclopropylmagnesium bromide (400 μL, 0.20 mmol, 0.5 M solution in THF) was added over a 1 min period. Upon completion of addition, the reaction mixture was stirred for 1 h. At the conclusion of this period, the reaction mixture was quenched with a 50% saturated NH$_4$Cl solution and then partitioned between ethyl acetate (10 mL) and 50% saturated NH$_4$Cl solution (5 mL). The organic phase was separated, dried over Na$_2$SO$_4$, and then concentrated in vacuo to yield a residue. The residue was purified by automated flash chromatography (SiO$_2$, 0-60% ethyl acetate/hexanes) to afford Example 2 as an off-white foam (24.9 mg, 77%). HPLC t$_R$ (Method D): 2.41 min (97% pure). LC/MS (m/z)=325 (M+H)+.

Example 3

3-(1-(4-Chlorophenyl)cyclopropyl)-7-cyclopropyl-[1,2,4]triazolo[4,3-a]pyrimidine

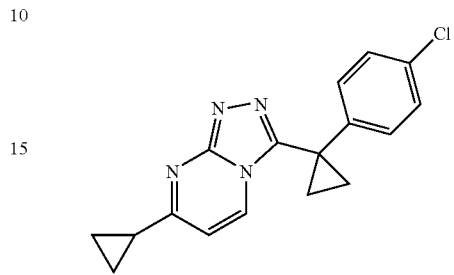

Compound 3A: 2-Chloro-4-cyclopropylpyrimidine

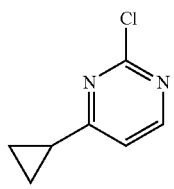

Argon was bubbled through a mixture of 2,4-dichloropyrimidine (298 mg, 2.0 mmol), cyclopropylboronic acid (172 mg, 2.0 mmol), and K$_3$PO$_4$ (1.06 g, 5.0 mmol) in THF (10 mL) in a crimp-top reaction tube for 10 minutes. After this period, Pd(dppf)$_2$Cl$_2$—CH$_2$Cl$_2$ (163 mg, 0.2 mmol) was added, and the vessel was capped. The resulting mixture was heated to 90° C. for 17 h. After this time, the reaction mixture was partitioned between water (2 mL) and diethyl ether (6 mL). The organic phase was separated, dried over Na$_2$SO$_4$, and then concentrated in vacuo. The resulting residue was purified by flash chromatography (SiO$_2$, 0-100% ethyl acetate/hexanes) to afford compound 3A, which was used in the preparation of compound 3B set forth below, as a colorless oil (108 mg, 35%). LC/MS (m/z)=155 (M+H)+.

Compound 3B: 4-Cyclopropyl-2-hydrazinylpyrimidine

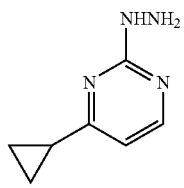 [SMILES: NNc1nccc(C2CC2)n1]

Compound 3A and anhydrous hydrazine (204 μL, 6.5 mmol) were dissolved in pyridine (2.6 mL). The reaction mixture was heated to 60° C. where it stirred for 4 h. At the conclusion of this period, the reaction mixture was concentrated in vacuo to yield a residue. The residue was purified by flash chromatography (SiO₂, 0-100% ethyl acetate/hexanes) to afford compound 3B as a white solid (85.4 mg, 88%). LC/MS (m/z)=151 (M+H)⁺.

Compound 3C: 1-(4-Chlorophenyl)-N'-(4-cyclopropylpyrimidine-2-yl)cyclopropanecarbohydrazide

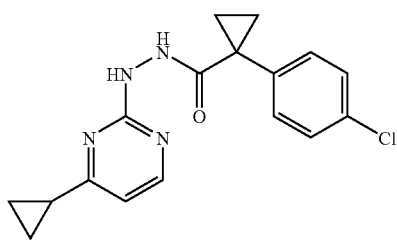 [SMILES: O=C(NNc1nccc(C2CC2)n1)C1(c2ccc(Cl)cc2)CC1]

To a 0° C. solution of 1-(4-chlorophenyl)cyclopropanecarboxylic acid (98.3 mg, 0.50 mmol) in THF (2 mL) was added 4-methylmorpholine (60.5 µL, 0.55 mmol). Upon completion of addition, the mixture was stirred for 10 minutes, and then isobutyl chloroformate (67.4 µL, 0.52 mmol) was added dropwise over a 2 minute period. Upon completion of addition, the reaction mixture was stirred for 1 h. After this time, a solution of hydrazine 3B (75.1 mg, 0.50 mmol) in THF (3 mL) was added dropwise over a 2 minute period. The resulting mixture was stirred for 10 minutes and then the cooling bath was removed. The reaction mixture was warmed to room temperature over a 1 h period. After this time, water (5 mL) and ethyl acetate (10 mL) were added, and the resulting mixture was stirred for 10 minutes. At the conclusion of this period, the organic phase was separated, dried over Na₂SO₄, and then concentrated in vacuo. The resulting residue was purified by flash chromatography (SiO₂, 0-60% ethyl acetate/hexanes) to afford compound 3C as a pale-yellow solid (121 mg, 74%). LC/MS (m/z)=329 (M+H)⁺.

Example 3

Compound 3C (69.0 mg, 0.21 mmol) was dissolved in POCl₃ (2 mL) and the resulting mixture was heated to reflux where it stirred for 3 h. After this time, the reaction mixture was concentrated in vacuo to yield a residue. The residue was partitioned between ethyl acetate and water, and the pH was adjusted to 7 with 1N NaOH. Once at the prescribed pH, the organic layer was separated, dried over Na₂SO₄, and then concentrated in vacuo to yield a residue. This residue was purified by flash chromatography (SiO₂, 0-100% ethyl acetate/hexanes) to afford Example 3 as an off-white solid (16.0 mg, 25%) HPLC $t_R$ (Method D): 1.88 min (>99% pure). LC/MS (m/z)=311 (M+H)⁺.

Example 4

8-(2-(Trifluoromethoxy)phenoxy)-3-(1-(4-chlorophenyl)cyclopropyl)-[1,2,4]triazolo[4,3-a]pyrazine

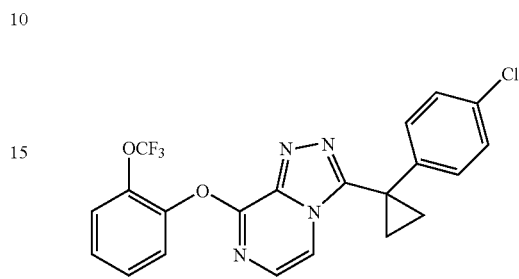

Compound 4A: 1-(4-Chlorophenyl)-N'-(3-chloropyrazine-2-yl)cyclopropanecarbohydrazide

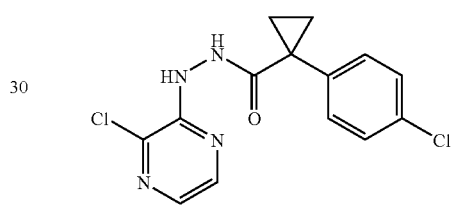

To a 0° C. solution of 1-(4-chlorophenyl)cyclopropanecarboxylic acid (0.77 g, 3.92 mmol) in THF (15 mL) was added 4-methylmorpholine (0.43 g, 4.3 mmol). The resulting mixture was stirred for 5 minutes, and then isobutyl chloroformate (0.56 g, 4.14 mmol) was added dropwise over 5 minutes. The resulting mixture was stirred for 1 h, and then a solution of compound 1A (0.56 g, 3.92 mmol) in THF/DMF/NMM (10 ml/2 ml/2 ml) was added. Upon completion of addition, the reaction mixture was warmed to room temperature where it stirred for 4 h. After this time, brine (15 mL) and ethyl acetate (50 mL) were added. The organic phase was separated, dried over Na₂SO₄, and then concentrated in vacuo. The resulting residue was purified by flash chromatography (SiO₂, 0-85% ethyl acetate/hexanes) to afford compound 4A as a solid (0.78 g, 61%). LC/MS (m/z)=323 (M+H)⁺.

Compound 4B: 8-Chloro-3-(1-(4-chlorophenyl)cyclopropyl)-1,2,4-triazolo[4,3-a]pyrazine

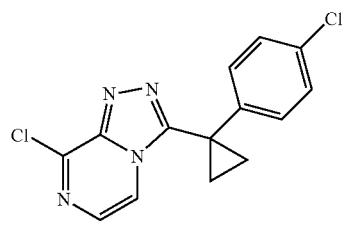 [SMILES: Clc1ccc(C2(c3nnc4c(Cl)nccn34)CC2)cc1]

Compound 4A (0.342 g, 1.06 mmol) was dissolved in POCl$_3$ (5 mL) and the resulting mixture was heated to 115° C. were it stirred for 12 h. At the conclusion of this period, the reaction mixture was concentrated in vacuo to yield a residue. The residue was partitioned between ethyl acetate and water, and the pH was adjusted to 7 with 10N NaOH. Once at the prescribed pH, the organic layer was separated, dried over Na$_2$SO$_4$, and then concentrated in vacuo to yield a residue. The residue was purified by flash chromatography (SiO$_2$, 0-100% ethyl acetate/hexanes) to afford compound 4B as an off-white solid (0.24 g, 74%). LC/MS (m/z)=306 (M+H)$^+$.

Example 4

A mixture of compound 4B (30.5 mg, 0.1 mmol), 2-(trifluoromethoxy)-phenol (36 mg, 0.2 mmol), silver nitrate (17 mg, 0.1 mmol) and KOH (8.2 mg, 0.2 mmol) in 1 ml of DMF was heated to 80° C. in a sealed tube for 4 h. At the conclusion of this period, the reaction mixture was cooled to room temperature. Once at the prescribed temperature, 3 ml of brine was added and the resulting mixture was extracted with ethyl acetate (3×5 ml). The organic layer was separated and concentrated in vacuo to yield a residue. The residue was purified by prep HPLC to afford Example 4 as an off-white solid (35 mg, 78%) HPLC R$_t$ (Method A): 3.66 min. LC/MS (m/z)=447 (M+H)$^+$.

Examples 5 to 27

Examples 5 to 27 in Table 1 were synthesized according to the procedures described in Examples 1 to 4 above, or by other similar methods known to one skilled in the art, with other appropriate reagents.

TABLE 1

| Example No. | Structure | LC/MS (ES+, M + H) | HPLC purity (%) |
| --- | --- | --- | --- |
| 5 | 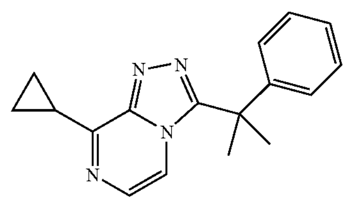 [SMILES: CC(C)(c1ccccc1)c1nnc2c(C3CC3)nccn12] | 279 | 97 |
| 6 | 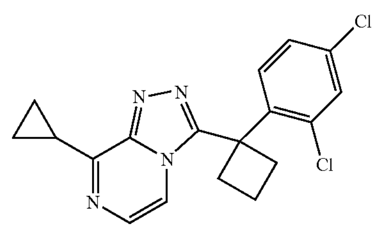 [SMILES: Clc1ccc(C2(c3nnc4c(C5CC5)nccn34)CCC2)c(Cl)c1] | 359 | 97 |
| 7 | 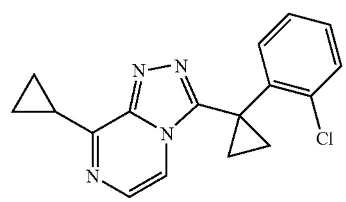 [SMILES: Clc1ccccc1C1(c2nnc3c(C4CC4)nccn23)CC1] | 311 | 97 |
| 8 | 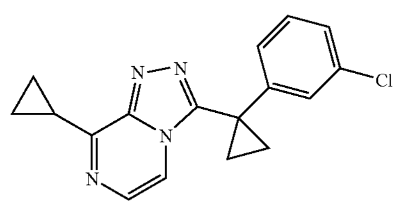 [SMILES: Clc1cccc(C2(c3nnc4c(C5CC5)nccn34)CC2)c1] | 311 | 97 |
| 9 | 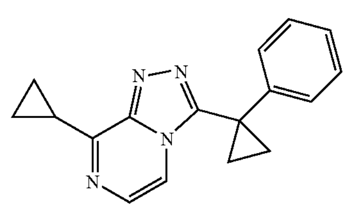 [SMILES: c1ccc(C2(c3nnc4c(C5CC5)nccn34)CC2)cc1] | 277 | 97 |

TABLE 1-continued

| Example No. | Structure | LC/MS (ES+, M + H) | HPLC purity (%) |
|---|---|---|---|
| 10 | 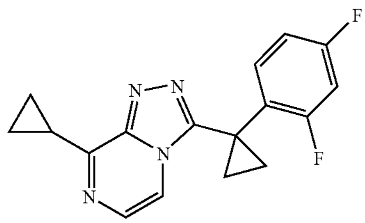 [SMILES: Fc1ccc(C2(c3nnc4c(C5CC5)nccn34)CC2)c(F)c1] | 313 | 96 |
| 11 | 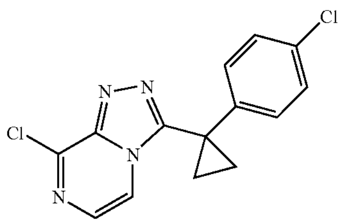 [SMILES: Clc1ccc(C2(c3nnc4c(Cl)nccn34)CC2)cc1] | 306 | >95 |
| 12 | 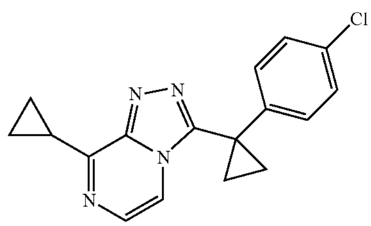 [SMILES: Clc1ccc(C2(c3nnc4c(C5CC5)nccn34)CC2)cc1] | 311 | >95 |
| 13 | 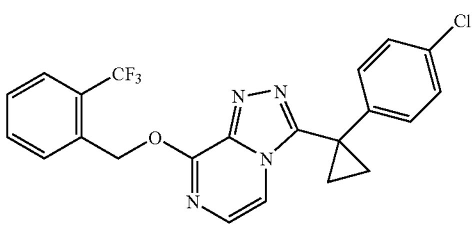 [SMILES: FC(F)(F)c1ccccc1COc1nccn2c(C3(c4ccc(Cl)cc4)CC3)nnc12] | 445 | >95 |
| 14 | 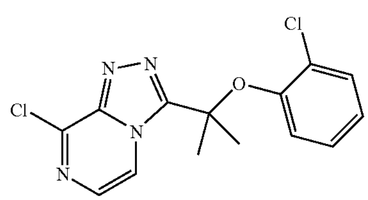 [SMILES: CC(C)(Oc1ccccc1Cl)c1nnc2c(Cl)nccn12] | 324 | >95 |
| 15 | 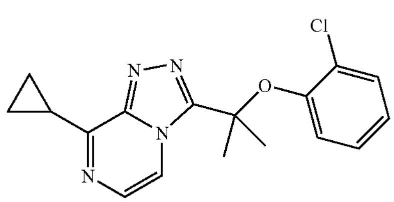 [SMILES: CC(C)(Oc1ccccc1Cl)c1nnc2c(C3CC3)nccn12] | 329 | >95 |
| 16 | 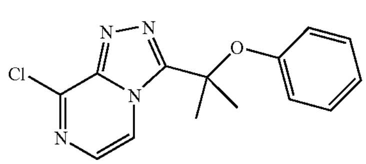 [SMILES: CC(C)(Oc1ccccc1)c1nnc2c(Cl)nccn12] | 289 | >95 |

TABLE 1-continued
| Example No. | Structure | LC/MS (ES+, M + H) | HPLC purity (%) |
|---|---|---|---|
| 17 | 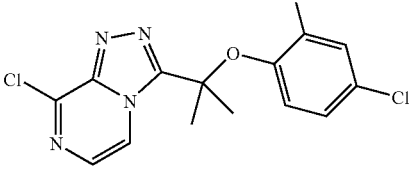 | 358 | >95 |
| 18 | 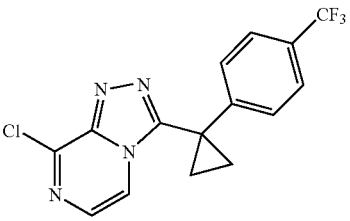 [SMILES: FC(F)(F)c1ccc(C2(c3nnc4c(Cl)nccn34)CC2)cc1] | 339 | >95 |
| 19 | 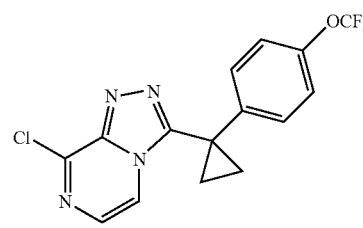 | 355 | >95 |
| 20 | 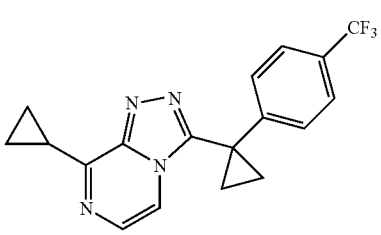 [SMILES: FC(F)(F)c1ccc(C2(c3nnc4c(C5CC5)nccn34)CC2)cc1] | 345 | >95 |
| 21 | 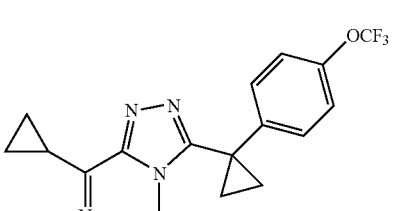 | 361 | >95 |
| 22 | 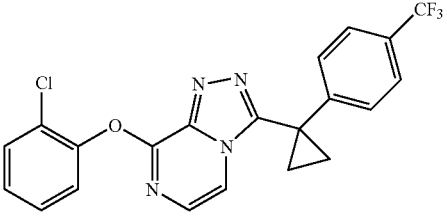 [SMILES: FC(F)(F)c1ccc(C2(c3nnc4c(Oc5ccccc5Cl)nccn34)CC2)cc1] | 431 | >95 |
| 23 | 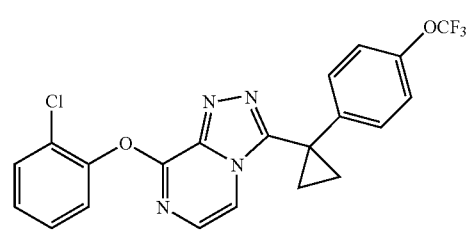 [SMILES: FC(F)(F)Oc1ccc(C2(c3nnc4c(Oc5ccccc5Cl)nccn34)CC2)cc1] | 447 | >95 |

TABLE 1-continued

| Example No. | Structure | LC/MS (ES+, M + H) | HPLC purity (%) |
|---|---|---|---|
| 24 | 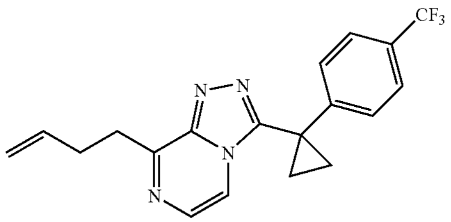 [SMILES: C=CCCc1nccn2c(C3(c4ccc(C(F)(F)F)cc4)CC3)nnc12] | 359 | >95 |
| 25 | 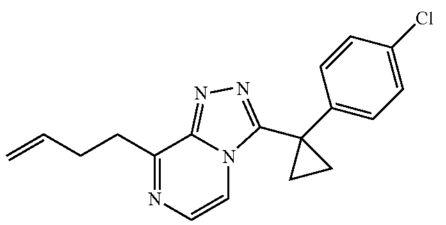 [SMILES: C=CCCc1nccn2c(C3(c4ccc(Cl)cc4)CC3)nnc12] | 325 | >95 |
| 26 | 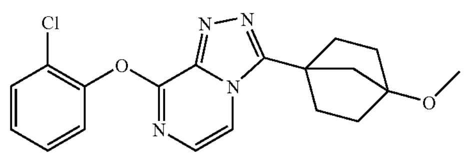 [SMILES: COC12CCC(c3nnc4c(Oc5ccccc5Cl)nccn34)(CC1)C2] | 371 | >95 |
| 27 | 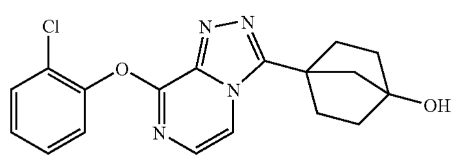 [SMILES: OC12CCC(c3nnc4c(Oc5ccccc5Cl)nccn34)(CC1)C2] | 357 | >95 |

Example 28

3-(1-(4-Chlorophenyl)cyclopropyl)thieno[2,3-e][1,2,4]triazolo[4,3-c]pyrimidine

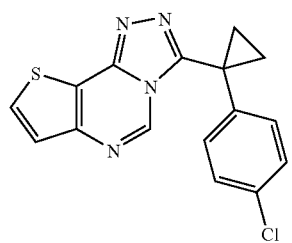 [SMILES: Clc1ccc(C2(c3nnc4c5sccc5ncn34)CC2)cc1]

Compound 28A:
4-Hydrazinylthieno[3,2d]pyrimidine

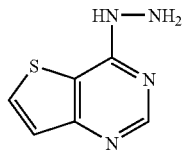 [SMILES: NNc1ncnc2ccsc12]

To a suspension of 4-chlorothieno[3,2-d]pyrimidine (1.71 g, 10 mmol) THF (10 mL) was added hydrazine (640 mg, 20 mmol) and the mixture was stirred at room temperature for 64 hours. The thick, pale tan slurry was filtered and the solid (desired product) was washed with THF (2×4 mL) and hexane (2×4 mL). This provided 1.968 g of crude compound 28A as a pale tan powder which was used as is in the next step. LC/MS (m/z)=167 (M+H)⁺.

Compound 28B: 1-(4-Chlorophenyl)-N'-(thieno[3,2-d]pyrimidin-4-yl)cyclopropanecarbohydrazide

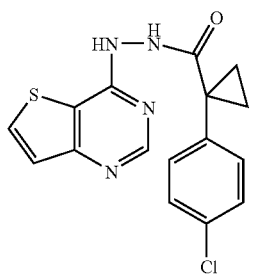 [SMILES: O=C(NNc1ncnc2ccsc12)C1(c2ccc(Cl)cc2)CC1]

To a solution of 1-(4-chlorophenyl)cyclopropanecarboxylic acid (1.97 g, 10 mmol) in 20 mL of THF was added NMM (1.11 g, 11 mmol). The resulting mixture was cooled to 0° C. and then isobutyl chloroformate (1.37 g, 10 mmol) was added. After 20 minutes at 0° C., compound 28A (1.66 g, 10 mmol) was added to the resulting white suspension. Upon completion of addition, the reaction mixture was allowed to warm to rt and stirred overnight. EtOAc (300 mL) and water (100 mL) was added. The aqueous layer was removed and the EtOAc layer (which contained the desired product as a precipitate) was washed successively with 100 mL of saturated aqueous sodium bicarbonate, ammonium chloride, and brine. The EtOAc layer (containing a solid precipitate) was filtered and the solid was washed with EtOAc (2×5 mL) to provide compound 28B as a tan powder (805 mg, 23%). LC/MS (m/z)=345.8 (M+H)⁺.

Example 28

To a slurry of compound 28B (35 mg, 0.1 mmol) in 1 mL of THF and 0.5 mL of carbon tetrachloride was added diisopropylethylamine (129 mg, 1.0 mmol). Upon completion of addition, the reaction mixture was cooled to 0° C. and then triethylphosphine (59 mg, 0.5 mmol) was added. The resulting mixture was stirred at 0° C. for 30 minutes and then water (2 mL) was added. The aqueous suspension was extracted with EtOAc (2×5 mL) and the combined extracts concentrated to give 47 mg of a yellow oil. This material was purified using silica gel chromatography (1% methanol in methylene chloride) followed by further purification of mixed fractions using silica gel preparative TLC (one Whatman 500 micron plate) to yield Example 28 as a pale yellow foam (21 mg, 64%). LC/MS (m/z)=327.8 (M+H)⁺.

Example 29

3-(1-(4-Chlorophenyl)cyclopropyl)-7,8,9,10-tetrahydro-[1,2,4]-triazolo[3,4-a]phthalazine TFA Salt

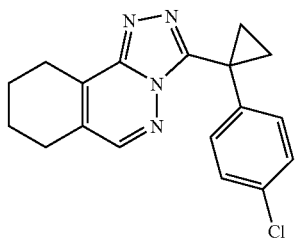 [SMILES: Clc1ccc(C2(c3nnc4c5c(cnn34)CCCC5)CC2)cc1]

Compound 29A: 1-Chloro-4-hydrazinyl-5,6,7,8-tetrahydrophthalazine

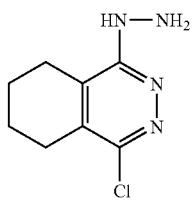 [SMILES: NNc1nnc(Cl)c2c1CCCC2]

To 1,4-dichloro-5,6,7,8-tetrahydrophthalazine (406 mg, 2.0 mmol) in 2 mL THF was added hydrazine (704 uL, 704 mm, 12 mmol) and the mixture heated at 60° C. for 5.5 hours. To the mixture was added 3 mL of water and 10 mL EtOAc. The resulting suspension was filtered, washed with water (3×5 mL) and concentrated to provide Compound 29A as a pale tan powder (222 mg, 56%). LC/MS (m/z)=199.7 (M+H)⁺.

Compound 29B: N'-(4-Chloro-5,6,7,8-tetrahydrophthalazin-1-yl)-1-(4-chlorophenyl)cyclopropanecarbohydrazide

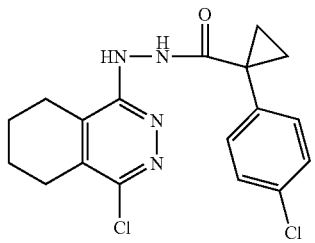 [SMILES: O=C(NNc1nnc(Cl)c2c1CCCC2)C1(c2ccc(Cl)cc2)CC1]

To a solution of 1-(4-chlorophenyl)cyclopropanecarboxylic acid (50 mg, 0.25 mmol) in 0.5 mL of THF was added NMM (28 mg, 0.28 mmol). The resulting mixture was cooled to 0° C. and then isobutyl chloroformate (34 mg, 0.25 mmol) was added. After 10 minutes, compound 29A (50 mg, 0.25 mmol) was added to the resulting white suspension. Upon completion of addition, the reaction mixture was stirred for 110 minutes and then EtOAc (3 mL) was added. Upon completion of addition, the resulting mixture was washed successively with 3 mL of saturated aqueous ammonium chloride, sodium bicarbonate, and brine; dried over magnesium sulfate, filtered, and then concentrated to provide compound 29B as an off-white powder (44 mg, 47%). LC/MS (m/z)=378.7 (M+H)+.

Compound 29C: 6-Chloro-3-(1-(4-chlorophenyl)cyclopropyl)-7,8,9,10-tetrahydro-[1,2,4]-triazolo[3,4-a]phthalazine

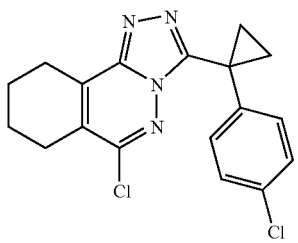

To a suspension of compound 29B (44 mg, 0.117 mmol) in 0.5 mL of THF and 0.2 mL of carbon tetrachloride was added diisopropylethylamine (120.7 mg, 0.936 mmol). Upon completion of addition, the reaction mixture was cooled to 0° C. and then triethylphosphine (55.2 mg, 0.468 mmol) was added. The resulting mixture was stirred for 40 minutes and then EtOAc (3 mL) was added. Upon completion of addition, the mixture was washed successively with 3 mL of saturated aqueous ammonium chloride, sodium bicarbonate, and brine; dried over magnesium sulfate, filtered, and concentrated to yield a residue. The residue was taken up in methanol (2 mL) water (1 mL) and TFA (3 drops). The resulting mixture was heated to reflux briefly and then allowed to cool to room temperature. Once at room temperature, the white precipitate that formed was filtered and washed with a 2:1 mixture of methanol and water (3×1 mL) to yield compound 29C as white crystals (24 mg, 57%, >95% HPLC purity). LC/MS (m/z)=360.7 (M+H)+.

Example 29

To 10% Pd—C (7 mg, 6.58 μmol) under nitrogen in a 25 mL pear-shaped flask equipped with a stirbar was added a suspension of compound 29C (16 mg, 0.045 mmol) in methanol (1 mL). The reaction mixture was flushed three times with vacuum then hydrogen (1 atm) and then stirred under an atmosphere of hydrogen (1 atm) for 15 h. After this time, the reaction mixture was through a Celite plug (~4 mm id×10 mm, using 3×1 mL methanol rinse) and then concentrated to yield crude solids (16 mg). The crude solids were purified by prep HPLC to give Example 29 as a pale yellow, oily solid (9 mg, 0.021 mmol, 46% yield). LC/MS (m/z)=325.8 (M+H)+.

Example 30

7-(Adamant-2-yl)-6-chloro-3-(2-phenyl)propan-2-yl)-[1,2,4]triazolo[4,3-b]pyridazine

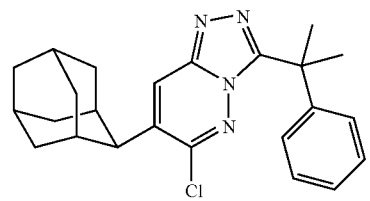 [SMILES: CC(C)(c1ccccc1)c1nnc2cc(C3C4CC5CC(C4)CC3C5)c(Cl)nn12]

Compound 30A:
4-(Adamant-2-yl)-3,6-dichloropyridazine

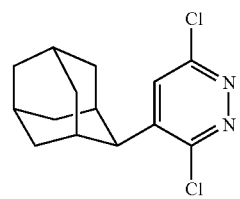 [SMILES: Clc1cc(C2C3CC4CC(C3)CC2C4)c(Cl)nn1]

To a suspension of 1-adamantane carboxylic acid (6309 mg, 35.0 mmol), 3,6-dichloropyridazine (1490 mg, 10 mmol), and sulfuric acid (800 μL, 15 mmol) in water (15 mL) was added silver(I) nitrate (425 mg, 2.5 mmol). Upon completion of addition, the mixture was heated to 70° C. Once at the prescribed temperature, a solution of ammonium peroxydisulfate (5705 mg, 25 mmol) in water (15 mL) was added during a 15 minute period. During addition, a slow evolution of gas was observed. Upon completion of addition, the reaction mixture was heated at 70° C. for 35 minutes. After this time, the grey-tan suspension was cooled to 0° C., and then adjusted to a pH of 9-10 using conc. aq. NH4OH (8-9 mL). Once at the prescribed pH, the suspension was filtered and washed with water (3×15 mL). The resulting solids were slurried in ether (20 mL), filtered and then rinsed with ether (3×20 mL). The filtrate and ethereal washes were combined and then concentrated to yield compound 30A as a tan solid (923 mg, 33%). LC/MS (m/z)=284 (M+H)+.

Compound 30B:
4-(Adamant-2-yl)-3-chloro-6-hydrazinopyridazine

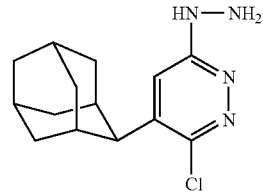 [SMILES: NNc1cc(C2C3CC4CC(C3)CC2C4)c(Cl)nn1]

To Compound 30A (330 mg, 1.17 mmol) was added 3 mL of THF and then hydrazine (373 mg, 11.7 mmol). The resulting mixture was capped and then placed in a 60° C. oil bath for 225 minutes. After this time, the mixture was cooled to RT and then concentrated to yield a residue. The residue was suspended in methanol (2 mL) and then heated to reflux. The resulting mixture was cooled to room temperature, filtered, and then washed with methanol (2×1 mL) to yield compound 30B as a tan solid (74 mg, 23%). LC/MS (m/z)=289.8 (M+H)$^+$.

Compound 30C: N'-(5-Adamant-2-yl-6-chloropyridazin-3-yl)-2-methyl-2-phenylpropanehydrazide

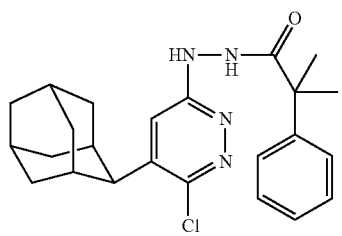 [SMILES: CC(C)(C(=O)NNc1cc(C2C3CC4CC(C3)CC2C4)c(Cl)nn1)c1ccccc1]

To a solution of 2-methyl-2-phenylpropanoic acid (27.7 mg, 0.169 mmol) and 4-methylmorpholine (20.39 μL, 0.185 mmol) in 0.5 mL THF at 0° C. added isobutyl chloroformate (22.14 μL, 169 mmol). Upon completion of addition, the mixture was stirred for 10 min and then solid compound 30B (47 mg, 0.169 mmol) was added. The reaction mixture was stirred for 75 min and then EtOAc (3 mL) was added. Upon completion of addition, the reaction mixture was washed successively with 2 mL each of saturated aqueous ammonium chloride, sodium bicarbonate, and then brine. The mixture was dried over magnesium sulfate, filtered and then concentrated to give crude compound 30C (76 mg). LC/MS (m/z)= 425.9 (M+H)$^+$.

Example 30

To a solution of compound 30C (76 mg, 0.179 mmol) and DIPEA (0.250 mL, 1.431 mmol) in THF (0.7 mL) and CCl$_4$ (0.3 mL) stirred at 0° C. was added triethylphosphine (0.106 mL, 0.715 mmol). Upon completion of addition, an emulsion containing much yellow precipitate was formed. The emulsion was stirred for 30 min and then EtOAc (3 mL) was added. The resulting mixture was washed successively with 2 mL each of saturated aqueous ammonium chloride, sodium bicarbonate, and brine; dried over magnesium sulfate, filtered and then concentrated to yield a residue. The residue was purified by prep HPLC to give Example 30 (26 mg, 28%). LC/MS (m/z)=407.9 (M+H)$^+$.

Examples 31 to 33

Examples 31 to 33 in Table 2 were synthesized in a similar manner as that described in Example 34 below, or by other similar methods known to one skilled in the art, with other appropriate reagents.

TABLE 2

| Example No. | Structure | LC/MS (ES+, M + H) | HPLC purity (%) |
|---|---|---|---|
| 31 | 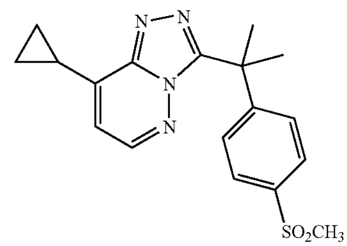 [SMILES: CC(C)(c1ccc(S(C)(=O)=O)cc1)c1nnc2c(C3CC3)ccnn12] | 356 | 100 |
| 32 | 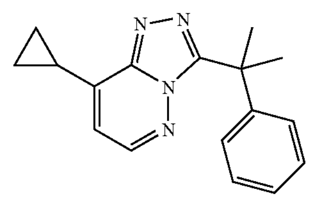 [SMILES: CC(C)(c1ccccc1)c1nnc2c(C3CC3)ccnn12] | 279 | 97 |
| 33 | 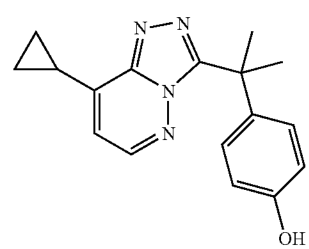 [SMILES: CC(C)(c1ccc(O)cc1)c1nnc2c(C3CC3)ccnn12] | 295 | 95 |

Example 34

3-(2-(4-Chlorophenyl)propan-2-yl)-8-cyclopropyl-[1,2,4]-triazolo[4,3-b]pyridazine

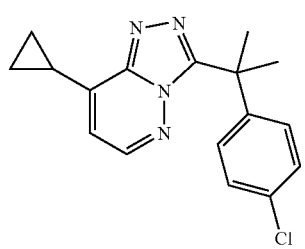 [SMILES: CC(C)(c1ccc(Cl)cc1)c1nnc2c(C3CC3)ccnn12]

Compound 34A: 6-Chloro-4-cyclopropyl-3-hydrazinylpyridazine

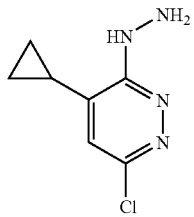 [SMILES: NNc1nnc(Cl)cc1C1CC1]

To a solution of 3,6-dichloro-4-cyclopropylpyridazine (3.2 g, 15.07 mmol) in THF (30 mL) was added hydrazine (1.893 mL, 60.3 mmol). The reaction mixture was heated at 60° C. for 9 h. After this time, the reaction mixture was cooled to rt. Once at the prescribed temperature, H$_2$O (30 mL) was added to the mixture, and the resulting mixture was extracted with EtOAc (3×30 mL). The combined extracts were dried over Na$_2$SO$_4$ and then concentrated by rotary evaporation to yield a crude residue. The residue was dissolved in MeOH (12 mL) and then purified via preparative HPLC to yield compound 34A (400 mg, 14%) as a yellow solid. LC/MS (m/z)=185.1 (M+H)$^+$.

Compound 34B: 6-Chloro-3-(2-(4-chlorophenyl)propan-2-yl)-8-cyclopropyl-[1,2,4]triazolo[4,3-b]pyridazine

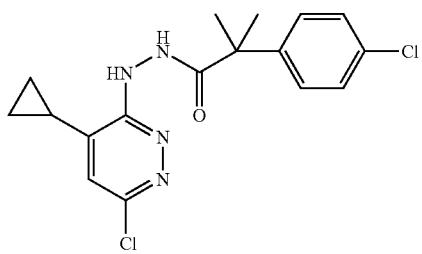 [SMILES: CC(C)(C(=O)NNc1nnc(Cl)cc1C1CC1)c1ccc(Cl)cc1]

To a solution of 2-(4-chlorophenyl)-2-methylpropanoic acid (48.9 mg, 0.246 mmol) and 4-methylmorpholine (0.030 ml, 0.271 mmol) in THF (1 mL) at 0° C. was added isobutyl chloroformate (0.032 ml, 0.246 mmol). Upon completion of addition, the resulting mixture was stirred for 15 min. After this time, a solution of compound 34A (50 mg, 0.271 mmol) in THF (1.5 mL) was added and the reaction mixture was stirred for 10 min. At the conclusion of this period, the reaction mixture was quenched with saturated aq. NaHCO$_3$ and then diluted with EtOAc (5 mL). After stirring for 5 min., the organic layer was separated and washed with saturated aq. NH$_4$Cl and aq. NaCl. The organic layer was dried over anhydrous sodium sulfate and then concentrated by rotary evaporation to yield compound 34B (92 mg) as a crude yellow solid with a purity of 83%. The crude product was utilized in the next step without further purification. LC/MS (m/z)=366 (M+H)$^+$.

Compound 34C: 6-Chloro-3-(2-(4-chlorophenyl)propan-2-yl)-8-cyclopropyl-[1,2,4]triazolo[4,3-b]pyridazine

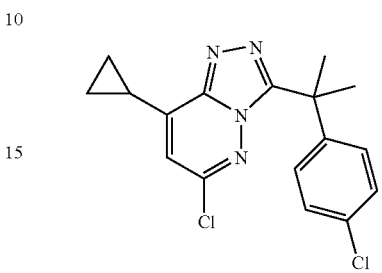

To a solution of compound 34B (82 mg, 0.224 mmol) in THF (0.8 mL) and CCl$_4$ (0.6 mL) was added DIPEA (0.392 mL, 2.245 mmol). The mixture was cooled to 0° C. and then triethylphosphine (0.332 mL, 2.245 mmol) was added. Upon the completion of the addition, the reaction mixture was stirred for 20 min. After this time, the reaction mixture was quenched with saturated aq. NaHCO$_3$ and then mixed with EtOAc (6 ml). The resulting mixture was vigorously stirred for 10 min. The organic layer was collected, washed with saturated aq. NH$_4$Cl followed by saturated aq. NaCl, dried over anhydrous Na$_2$SO$_4$, and then concentrated by rotary evaporation to yield compound 34C (90 mg) as the crude product with a purity about 85%. The crude product was utilized in the next step without further purification. LC/MS (m/z)=347.1 (M+H)$^+$.

Example 34

To a flask flushed with N$_2$ and Pd/C (22 mg, 10% wt) in MeOH (0.5 mL) was added a solution of Compound 34C (90 mg, 0.220 mmol) in MeOH (0.5 mL). The reaction mixture was evacuated and filled with H$_2$ and then a H$_2$ balloon was placed on the top of the flask. The reaction mixture was stirred at rt under H$_2$ atmosphere for 5 h. Upon completion of the reaction, the reaction mixture was filtered through Celite to remove the insolubles, purified via preparative HPLC and then neutralized to yield Example 34 (22 mg, 31%) as a white solid. LC/MS (m/z)=313.2 (M+H)$^+$.

Example 35

2-(3-(1-(4-Chlorophenyl)cyclopropyl)-[1,2,4]triazolo[4,3-a]pyrazin-8-yl)propan-2-ol TFA salt

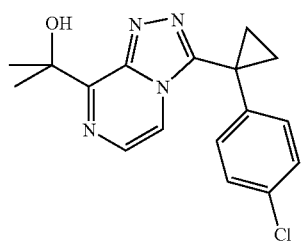 [SMILES: CC(C)(O)c1nccn2c(C3(c4ccc(Cl)cc4)CC3)nnc12]

Compound 35A: 1-(4-Chlorophenyl)-N'-(3-chloro-pyrazin-2-yl)cyclopropanecarbohydrazide

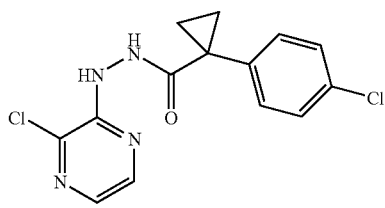 [SMILES: O=C(NNc1nccnc1Cl)C1(c2ccc(Cl)cc2)CC1]

To a solution of 1-(4-chlorophenyl)cyclopropanecarboxylic acid (6300 mg, 32.0 mmol) and 4-methylmorpholine (3.87 mL, 35.2 mmol) in THF (100 mL) at 0° C. was added isobutyl chloroformate (4.21 mL, 32.0 mmol). After completion of addition, the reaction mixture was stirred for 25 min, and then a solution of 2-chloro-3-hydrazinylpyrazine (5095 mg, 35.2 mmol) in THF (60 mL) was added. The resulting mixture was stirred for 45 min. After that time, the reaction mixture was quenched with saturated aq. $NaHCO_3$ and then extracted with EtOAc (25 mL). The organic layer was collected, washed with saturated aq. $NH_4Cl$ followed by aq. NaCl., dried over $Na_2SO_4$ and then concentrated by rotary evaporation to yield compound 35A (10 g, 97% yield) as a yellow solid. The crude product was utilized in the next step without further purification. LC/MS (m/z)=323.1 [M+1]$^+$.

Compound 35B: 8-Chloro-3-(1-(4-chlorophenyl)cyclopropyl)-[1,2,4]-triazolo[4,3-a]pyrazine

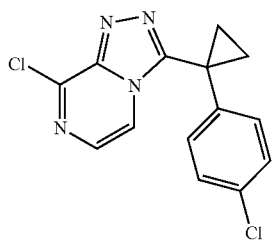 [SMILES: Clc1ccc(C2(c3nnc4c(Cl)nccn34)CC2)cc1]

To a solution of compound 35A (10 g, 30.9 mmol) in THF (80 mL) and $CCl_4$ (30 mL) was added DIPEA (27.0 mL, 155 mmol). Upon completion of addition, the resulting mixture was cooled to 0° C. and triethylphosphine (22.85 mL, 155 mmol) was slowly added. The reaction mixture was stirred for 40 min and then analyzed by LC/MS, which indicated that all of the reactants had been consumed. The reaction mixture was quenched with saturated aq. $NaHCO_3$ and then diluted with EtOAc (300 ml). The organic layer was collected, washed with saturated aq. $NH_4Cl$, followed by aq. NaCl, dried over $Na_2SO_4$, and then concentration by rotary evaporation to yield a yellow residue. The yellow residue was purified via ISCO column chromatography to yield compound 35B (4.7 g) as a yellow solid. LC/MS (m/z)=305.1 (M+H)$^+$.

Example 35

To a suspension of lithium pieces (1024 mg, 147 mmol) in THF (20 mL) was slowly added a solution of compound 35B (300 mg, 0.983 mmol) and acetone (1.08 mL, 14.75 mmol) in THF (5 mL) at −78° C. The suspension was stirred at −78° C. for 30 minutes and then warmed to 0° C., where it stirred for 15 minutes. After this time, the reaction mixture was re-cooled to −78° C. and the majority of the remaining lithium pieces were removed via spatula. Water was added to the cold solution, and the resulting mixture was allowed to warm to RT. Once at the prescribed temperature, the aqueous solution was extracted with ethyl acetate followed by 10% MeOH/$CHCl_3$. The organic extracts were combined, dried over $MgSO_4$, and concentrated by rotary evaporation to yield a residue. The residue was purified via column chromatography ($SiO_2$, 0-100% ethyl acetate/hexanes–20% methanol/ethyl acetate), followed by prep HPLC to yield Example 35 as a colorless oil (8.3 mg, 0.018 mmol, 2% yield). HPLC $R_t$ (Method B): 1.83 min. LC/MS (m/z)=329 (M+H)$^+$.

Example 36

2-(3-(1-(4-Chlorophenyl)cyclopropyl)-[1,2,4]-triazolo[4,3-b]pyridazin-8-yl)propan-2-ol

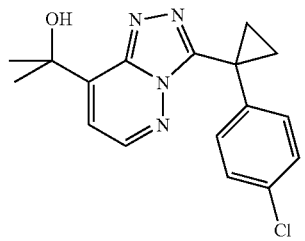 [SMILES: CC(C)(O)c1ccnn2c(C3(c4ccc(Cl)cc4)CC3)nnc12]

Compound 36A: Ethyl 3,6-dichloropyridazine-4-carboxylate

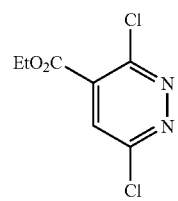 [SMILES: CCOC(=O)c1cc(Cl)nnc1Cl]

To a solution of 3,6-dichloropyridazine-4-carboxylic acid (5 g, 25.9 mmol), EtOH (4.77 g, 104 mmol), and DMAP (317 mg, 2.59 mmol) in THF (30 mL) was added EDCI (5.46 g, 28.5 mmol). The reaction mixture was stirred for 50 min. After this time, the solvent was removed in vacuo and EtOAc (200 mL) was added. Upon completion of addition, the resulting mixture was washed with 100 mL each of water, saturated aqueous $NaHCO_3$, and brine, dried over $MgSO_4$, filtered and then concentrated to give compound 36A (4.4 g, 77%) as a pale yellow oil. LC/MS (m/z)=222 (M+H)⁺.

Compound 36B: Ethyl 6-chloro-3-hydrazinylpyridazine-4-carboxylate

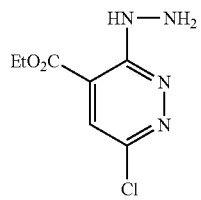 [SMILES: CCOC(=O)c1cc(Cl)nnc1NN]

To a solution of compound 36A (13.8 g, 62.4 mmol) in THF (60 mL) was added hydrazine hydrate (6.68 mL, 137 mmol). Upon completion of addition, the clear, pale yellow solution immediately turned red-brown and cloudy. A tan suspension with a red-brown thick oily precipitate on the walls of the flask developed shortly thereafter. The mixture was stirred for 80 min and the THF solution and precipitate was decanted away from the dark, oily residue. The oily residue was rinsed with THF (2×10 mL) and added to the decanted THF/solid mixture. Water (60 mL) was added to the THF slurry and the resulting mixture was heated to near reflux and then allowed to cool to RT with stirring. Once at the prescribed temperature, the mixture was filtered and the collected solid was washed with water (3×20 mL) to yield crude compound 36B (9.93 g) as a tan-orange solid. A portion of the crude material (8.762 g) was dissolved in EtOH (100 mL). The resulting solution was heated to reflux and then allowed to cool to room temperature where it was stirred for 2 hours (after 10-20 minutes crystals began to form). After this time, the mixture was filtered and the solid was washed with EtOH (3×5 mL) followed by hexane (3×20 mL) to give compound 36B (5.99 g) as orange crystalline needles. LC/MS (m/z)=217.6 (M+H)⁺.

Compound 36C: Ethyl 6-chloro-3-(2-(1-(4-chlorophenyl)cyclopropanecarbonyl)-hydrazinyl)-pyridazine-4-carboxylate

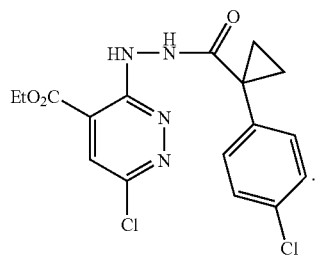 [SMILES: CCOC(=O)c1cc(Cl)nnc1NNC(=O)C1(c2ccc(Cl)cc2)CC1]

To a solution of 1-(4-chlorophenyl)cyclopropanecarboxylic acid (2.00 g, 10.16 mmol) in 40 mL THF was added 4-methylmorpholine (1.68 mL, 15.23 mmol). Upon completion of addition, the solution temperature was lowered to 0° C., and ethyl chloroformate (1.10 g, 10.16 mmol) was added with stirring. Upon completion of addition, the mixture was stirred at 0° C. for 30 minutes, and then compound 36B (2.20 g, 10.16 mmol) was added. The reaction mixture was stirred at 0° C. for another hour. After this time, the reaction mixture was quenched with water (10 mL) and then extracted with ethyl acetate (60+30 mL). The combined organic extracts were dried over MgSO₄ and concentrated by rotary evaporation to yield a residue. The residue was purified by column chromatography (0-50% ethyl acetate/hexanes) to provide compound 36C (3.75 g, 93% yield) as a yellow powder. LC/MS (m/z)=395 (M+H)⁺.

Compound 36D: Ethyl 6-chloro-3-(1-(4-chlorophenyl)cyclopropyl)-[1,2,4]triazolo[4,3-b]pyridazine-8-carboxylate

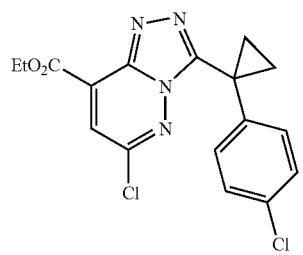 [SMILES: CCOC(=O)c1cc(Cl)nn2c(C3(c4ccc(Cl)cc4)CC3)nnc12]

Compound 36C (3.74 g, 9.46 mmol) was dissolved in CH₂Cl₂ (40 mL) and the resulting solution was cooled to −78° C. Once at the prescribed temperature, DIPEA (8.26 mL, 47.3 mmol), triethylphosphine (2.236 g, 18.93 mmol), and carbon tetrachloride (13.73 mL, 142 mmol) were added sequentially. Upon completion of addition, the mixture was stirred at −78° C. for 20 minutes and then at 0° C. for 10 minutes. After this time, H₂O was added and the organic layer was separated from the aqueous layer. The aqueous layer was extracted again with CH₂Cl₂. The organic extracts were combined, dried over MgSO₄, and concentrated by rotary evaporation to yield a residue. The residue was purified by column chromatography (SiO₂, 0-50% ethyl acetate/hexanes) to yield compound 36D (1.59 g, 45% yield) as a yellow powder. LC/MS (m/z)=377 (M+H)⁺.

Compound 36E: Methyl 3-(1-(4-chlorophenyl)cyclopropyl)-[1,2,4]triazolo[4,3-b]pyridazine-8-carboxylate

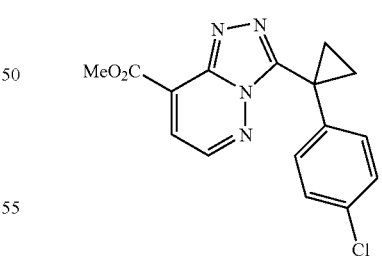

To a solution of compound 36D (1.50 g, 3.98 mmol) in ethyl acetate (45 mL) and methanol (15 mL) was added DIPEA (3.13 mL, 17.89 mmol) and 5% Pd/C (0.3 g). The resulting mixture was degassed and then stirred under H₂ balloon for 12 hours. After this time, the mixture was analyzed by LC-MS, which indicated that mono-dechlorination and transesterification had occurred. The catalyst was filtered off and the liquid portion was concentrated by rotary evaporation to yield a residue. The residue was purified by column chromatography (SiO$_2$, 0-100% ethyl acetate/hexanes) to provide compound 36E (0.63 g, 48% yield) as a yellow powder. LC/MS (m/z)=329 (M+H)$^+$.

Compound 36F: 1-(3-(1-(4-Chlorophenyl)cyclopropyl)-[1,2,4]-triazolo[4,3-b]pyridazin-8-yl)ethanone

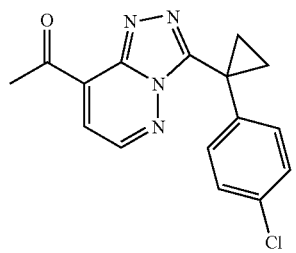 [SMILES: CC(=O)c1ccnn2c(C3(c4ccc(Cl)cc4)CC3)nnc12]

To a solution of compound 36E (45 mg, 0.137 mmol) in THF (5 mL) was added fresh anhydrous cerium (III) chloride (101 mg, 0.411 mmol) under argon. Upon completion of addition, the mixture was cooled to −78° C. where it stirred for 5 minutes. After this time, a solution of methylmagnesium chloride in THF (0.091 mL, 3 M, 0.274 mmol) was added at −78° C. The resulting mixture was stirred at −78° C. for 20 minutes and then another equivalent of a solution of methylmagnesium chloride in THF (0.046 mL, 3 M, 0.137 mmol) was added. The mixture continued to be stirred at −78° C. under argon for 5 minutes. At the conclusion of this period, the reaction was stopped by the addition of aqueous 1N HCl (2 mL) to the cold solution (−78° C.). The resulting mixture was slowly warmed to room temperature and then an aqueous 1N NaOH solution was added to adjust the pH value to about 8. Once at the prescribed pH, the reaction mixture was extracted with 10% CH$_3$OH/EtOAc followed by 10% CH$_3$OH/CHCl$_3$. The combined organic extracts were dried over MgSO$_4$ and concentrated by rotary evaporation to yield a residue. The residue was purified by column chromatography (SiO$_2$, 0-80% ethyl acetate/hexanes) to afford compound 36F (19.9 mg, 47% yield) as yellow crystals. LC/MS (m/z)= 313 (M+H)$^+$.

Example 36

To a solution of compound 36F (19.9 mg, 0.064 mmol) in THF (5 mL) was added anhydrous cerium (III) chloride (62.7 mg, 0.255 mmol) under argon. Upon completion of addition, the resulting mixture was cooled to −78° C. where it stirred for 5 minutes. At the conclusion of this period, a solution of methylmagnesium chloride in THF (0.042 mL, 3 M, 0.127 mmol) was added at −78° C. The resulting mixture was stirred at −78° C. for 15 minutes. An additional solution of methylmagnesium chloride in THF (0.025 mL, 3 M, 0.076 mmol) was added, and the mixture was stirred at −78° C. for 5 minutes. After this time, the reaction was stopped by the addition of aqueous 1N HCl (1 mL) to the cold solution (−78° C.). The reaction mixture was slowly warmed to room temperature and then an aqueous 1N NaOH solution was added to adjust the pH value to about 8. Once at the prescribed pH, the mixture was extracted with 10% CH$_3$OH/EtOAc followed by 10% CH$_3$OH/CHCl$_3$. The combined organic extracts were dried over MgSO$_4$ and then concentrated by rotary evaporation to yield a residue. The residue was purified by prep HPLC to afford Example 36 as a white powder (10 mg, 35% yield). LC/MS (m/z)=329 (M+H)$^+$.

Examples 37 to 48

Examples 37 to 48 in Table 3 were synthesized according to the procedures described above, or by other similar methods known to one skilled in the art, with other appropriate reagents.

TABLE 3

| Example No. | Structure | LC/MS (ES+, M + H) | HPLC purity (%) |
|---|---|---|---|
| 37 | [8-cyclopropyl-3-(2-phenoxypropan-2-yl)-[1,2,4]triazolo[4,3-a]pyrazine] | 295 | >95 |
| 38 | [8-cyclopropyl-3-(2-(2,4-dichlorophenoxy)propan-2-yl)-[1,2,4]triazolo[4,3-a]pyrazine] | 363 | >95 |
| 39 | [8-cyclopropyl-3-(2-(3-chlorophenyl)propan-2-yl)-[1,2,4]triazolo[4,3-a]pyrazine] | 313 | >95 |

TABLE 3-continued

| Example No. | Structure | LC/MS (ES+, M + H) | HPLC purity (%) |
|---|---|---|---|
| 40 | 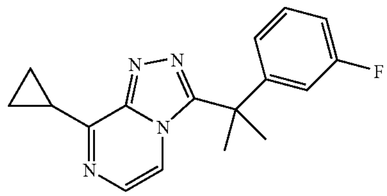 [SMILES: CC(C)(c1cccc(F)c1)c1nnc2c(C3CC3)nccn12] | 297 | >95 |
| 41 | 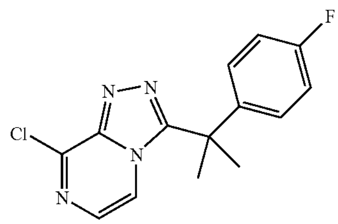 [SMILES: CC(C)(c1ccc(F)cc1)c1nnc2c(Cl)nccn12] | 291 | >95 |
| 42 | 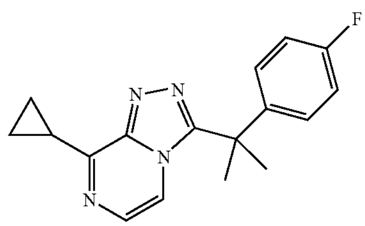 [SMILES: CC(C)(c1ccc(F)cc1)c1nnc2c(C3CC3)nccn12] | 297 | >95 |
| 43 | 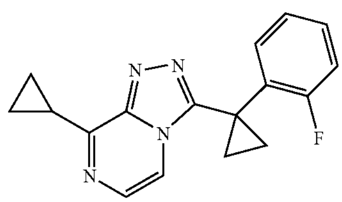 | 295 | >95 |
| 44 | 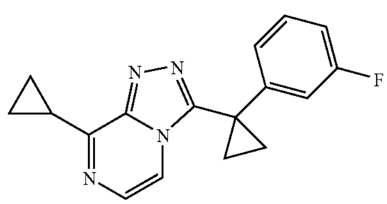 [SMILES: Fc1cccc(C2(c3nnc4c(C5CC5)nccn34)CC2)c1] | 295 | >95 |
| 45 | 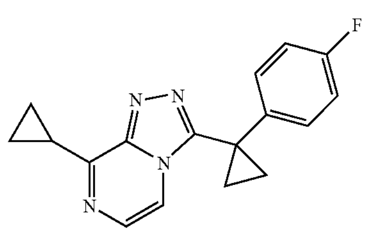 [SMILES: Fc1ccc(C2(c3nnc4c(C5CC5)nccn34)CC2)cc1] | 295 | >95 |
| 46 | 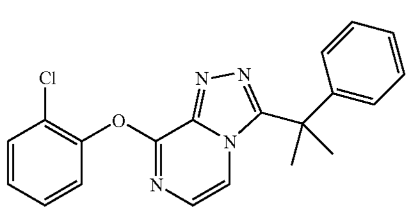 [SMILES: CC(C)(c1ccccc1)c1nnc2c(Oc3ccccc3Cl)nccn12] | 365 | >95 |

TABLE 3-continued

| Example No. | Structure | LC/MS (ES+, M + H) | HPLC purity (%) |
|---|---|---|---|
| 47 | 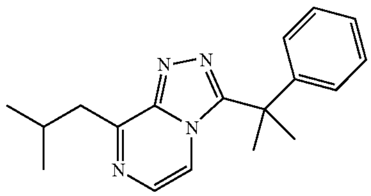 [SMILES: CC(C)Cc1nccn2c(C(C)(C)c3ccccc3)nnc12] | 295 | >95 |
| 48 | 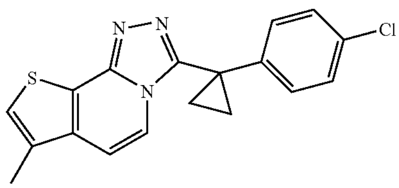 [SMILES: Cc1csc2c1ccn1c(C3(c4ccc(Cl)cc4)CC3)nnc21] | 341 | >95 |

Assay(S) for 11-Beta-Hydroxysteroid Dehydrogenase Activity

The in vitro inhibition of recombinant human 11beta-HSD1 was determined as follows.

[$^3$H]-Cortisone with a specific radioactivity of 50 Ci/mmol (ART 743, Lot: 050906) was from American Radiolabeled Chemicals, Inc. (St Louis, Mo.); monoclonal ab to Cortisol (P01-9294M-P, Lot: L-28) was from East Coast Bio., (North Berwick, Me.); Protein A-yttrium silicate, type-1, SPA bead NJ® (RPN-143) was from Amersham LifeSciences, (Piscataway, N.J.); 384 well-Optiplate384® (#6007299) was from PerkinElmer (Boston, Mass.); DPBS, pH 7.4 (14040) is from GIBCO, (Grand Island, N.Y.); carbenoxolone (C4790) is from Sigma, (St Louis, Mo.).

Full length recombinant human 11β-HSD1 cDNAs and the cDNA encoding human 11β-HSD2 were expressed stably in HEK 293 EBNA cells. Cells were grown in DMEM (high glucose) containing MEM non-essential amino acids, L-glutamine, hygromycin B (200 μg/ml), and G-418 (200 μg/ml) in the presence of 10% FBS.

Human 11β-HSD1 transfected HEK 293 EBNA cells were grown to 80% confluency and the cell pellet was quick frozen and stored at −80° C. before purification. Cell paste, 40 g from −80° C. storage, was thawed in water and then 100 ml of homogenization buffer H (0.01 M sodium phosphate pH 6.5 containing 0.25 M sucrose and protease inhibitor cocktail (Roche #1836145 1 tablet per 50 ml) were added to completely thaw the paste. The cell paste suspension was homogenized using a Polytron for 20 seconds to create a homogeneous mixture. Additional buffer H was added to a volume of 300 ml and cells were broken open using a N2-bomb (at 4° C.) in two batches by treating at 500 psi. The extract was centrifuged at 750×g for 30 min. The supernatant was centrifuged at 20,000×g for 30 min. The supernatant was further centrifuged at 105,000×g for 60 min. The 105,000×g pellet was resuspended in buffer H and centrifuged at 105,000×g for 60 min. The microsome pellet was scraped from the bottom of tube and resuspended in 0.01M phosphate buffer, pH 6.5 containing protease inhibitors (Roche #1836145, 1 tablet per 50 ml). Aliquots were stored at −80° C. until needed. The protein concentration was measured by the BioRad method using BSA standard.

Compounds were dissolved in DMSO to obtain 10 mM stock concentrations. From the 10 mM stock, the compounds were diluted in DMSO to achieve the concentrations.

11β-HSD1 SPA Enzyme Assay

11β-HSD1 was assayed by Scintillation Proximity assay in a 384-well PerkinElmer white plate. The dose response of the compounds was determined using 11 half-log dilutions of compound in DMSO in duplicate. To each well, 0.5 μl of compound dilution in DMSO were added. 15 μl of assay buffer (for blanks) or 15 μl of human microsomes in assay buffer were added next and the plates were incubated for 10 min at room temperature. The final microsomal protein concentration was 1.1 μg/assay. Duplicates were in the same plate one row below the other. 10 μl of $^3$H-cortisone (final concentration 40 nM) was added to each well and the plate was spun down to mix and bring down the contents to the bottom of the wells. The plates were incubated at room temperature with gentle shaking for 4 hrs. The reaction was stopped with addition of 10 μl of 10 mM carbenoxolone. Then, 0.5 mg of yttrium silicate SPA beads coupled to anti-cortisol antibody in 20 μl were added to all the wells of plate, which were spun down once more and incubated at room temperature overnight. The plate was read in a TopCount® (1 min/well). Data were uploaded automatically to Tool Set, a Lead Evaluation informatics program for data capture and calculation. Graphs were generated with the Curve Master program.

Compounds of the present invention were tested in the assay described immediately above and the results shown in the Table 4 below were obtained.

TABLE 4

| Example | h HSD1 IC$_{50}$ (nM) |
|---|---|
| 1 | 1.8 |
| 3 | 453 |
| 4 | 0.5 |
| 6 | 0.6 |
| 16 | 6033 |
| 25 | 1.3 |
| 27 | 336 |
| 28 | 86 |
| 29 | 12 |
| 31 | 1501 |
| 35 | 7.9 |
| 36 | 1.2 |
| 38 | 1.8 |
| 41 | 5126 |
| 49 | 10000 |

The in vivo inhibition of recombinant human 11beta-HSD1 was determined as follows.

Studies were conducted utilizing diet induced obese (DIO) mice obtained from Jackson Laboratory (ME, USA). These mice were fed a 60% fat diet (Research Diets D12492) soon after weaning and kept on this diet for 24 weeks. These mice were individually housed. All mice were housed under controlled temperature (23° C.) and lighting (12 hours of light between 6 am to 6 pm, 12 hours of dark) with free access to water. The animals continued on this diet and were utilized for experimentation at 30 to 32 weeks of age, at which time these mice weighed 45 to 55 grams.

The basic model of 11-dehydrocorticosterone (DHC) administration to mice to produce corticosterone has been reported in the literature for clinical and preclinical evaluation of the activity of 11β-HSD. Essentially DHC (Steraloids INC, Newport R.I.), was suspended in the vehicle at a concentration of 10 mg/kg in a volume of 7.5 ml/kg of mouse body weight. For a typical study, non-fasting mice were weighed and separated into groups (n=6) where body weights are not statistically different from each other. Animals were bled via a tail knick, for a 0 time sample and then dosed orally (7.5 ml/kg) with vehicle or drug. At 60 minutes post administration of vehicle or compound, mice were bled again via the tail tip and dosed orally (7.5 ml/kg) with DHC 10 mg/kg. All animals were subsequently bled at 30, 60 and 120 minutes post DHC dosing. Thirty-five microliters of whole blood are collected per time point in microvette tubes coated with EDTA (Sarstedt Tubes Microvette CB 300/Haematology Potassium EDTA #16.444.300) and kept on ice. Samples were centrifuged at 4° C. in a Beckman Coulter centrifuge for 10 minutes at 2500 RPM. Plasma was separated and collected and immediately frozen at −20° C. until corticosterone analysis could be assessed.

Plasma Corticosterone was measured using an ETA (IDS AC-14F1). Samples were measured at (1:2) for the −30 (or −60 minute) and 0 time point and (1:10) for the 30, 60 and 120 minutes time points. AUC was calculated using Graphpad and the zero timepoint was used as the baseline. One way ANOVA was calculated using Sigmastat. A p value of less that 0.05 via post hoc analysis with Dunnett's was used to determine statistical significance.

The vehicle utilized for the suspension of the compounds was 0.5% methocel; 0.1% tween 80 in water. Methocel Cellulose (M-0262) was purchased from Sigma-Aldrich, St Louis, Mo. 6. Tween 80 (274364) was purchased from Sigma-Aldrich, St Louis, Mo. Compounds were administered in 7.5 ml/kg volumes at final dosages of 0.1 to 300 mg/kg depending on the study and compound evaluated.

Utilities and Combinations

A. Utilities

The compounds of the present invention possess activity as inhibitors of the enzyme 11-beta-hydroxysteroid dehydrogenase type I, and, therefore, may be used in the treatment of diseases associated with 11-beta-hydroxysteroid dehydrogenase type 1 activity. Via the inhibition of 11-beta-hydroxysteroid dehydrogenase type I, the compounds of the present invention may preferably be employed to inhibit or modulate glucocorticoid production, thereby interrupting or modulating cortisone or cortisol production.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, delayed wound healing, atherosclerosis and its sequelae (acute coronary syndrome, myocardial infarction, angina pectoris, peripheral vascular disease, intermittent claudication), abnormal heart function, myocardial ischemia, stroke, Metabolic Syndrome, hypertension, obesity, dislipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma and inflammatory diseases, such as, rheumatoid arthritis, Cushing's Disease, Alzheimer's Disease and osteoarthritis.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents,* 1:1-24 (2001).

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other 11-beta-hydroxysteroid dehydrogenase type I inhibitors or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dislipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, memory enhancing agents, cognition promoting agents and anti-inflammatory agents.

Examples of suitable anti-diabetic agents for use in combination with the compounds of the present invention include insulin and insulin analogs: LysPro insulin, inhaled formulations comprising insulin; glucagon-like peptides; sulfonylureas and analogs: chlorpropamide, glibenclamide, tolbutamide, tolazamide, acetohexamide, glypizide, glyburide, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; thiazolidinediones: ciglitazone, pioglitazone, troglitazone, rosiglitazone; PPAR-gamma agonists; PPAR-alpha agonists; PPAR alpha/gamma dual agonists; SGLT2 inhibitors; dipeptidyl peptidase-IV (DPP4) inhibitors; glucagon-like peptide-1 (GLP-1) receptor agonists; aldose reductase inhibitors; RXR agonists: JTT-501, MCC-555, MX-6054, DRF2593, G1-262570, KRP-297, LG100268; fatty acid oxidation inhibitors: clomoxir, etomoxir; α-glucosidase inhibitors: precose, acarbose, miglitol, emiglitate, voglibose, MDL-25,637, camiglibose, MDL-73,945; beta-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386,398; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER17411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, C798023; and galanin receptor agonists.

Other suitable thiazolidinediones include Mitsubishi's MCC-555 (disclosed in U.S. Pat. No. 5,594,016), Glaxo-Wellcome's GL-262570, englitazone (CP-68722, Pfizer), or darglitazone (CP-86325, Pfizer, isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi).

Suitable PPAR alpha/gamma dual agonists include AR-HO39242 (Astra/Zeneca), GW-409544 (Glaxo-Wellcome), KRP297 (Kyorin Merck), as well as those disclosed by Murakami et al., "A Novel Insulin Sensitizer Acts As a Coligand for Peroxisome Proliferation—Activated Receptor Alpha (PPAR alpha) and PPAR gamma; Effect of PPAR alpha Activation on Abnormal Lipid Metabolism in Liver of Zucker Fatty Rats", *Diabetes,* 47:1841-1847 (1998), and WO 01/21602, the disclosure of which is incorporated herein by reference, employing dosages as set out therein, which compounds designated as preferred are preferred for use herein.

Suitable alpha2 antagonists also include those disclosed in WO 00/59506, employing dosages as set out herein.

Suitable SGLT2 inhibitors include T-1095, phlorizin, WAY-123783, and those described in WO 01/27128.

Suitable DPP4 inhibitors include saxagliptan, sitagliptan, vildagliptan, and denagliptan.

Suitable aldose reductase inhibitors include those disclosed in WO 99/26659.

Suitable meglitinides include nateglinide (Novartis) or KAD1229 (PF/Kissei).

Examples of glucagon-like peptide-1 (GLP-1) receptor agonists include Exenatide (Byetta™), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DAC™).

Other anti-diabetic agents that can be used in combination with compounds of the invention include ergoset and D-chiroinositol.

Suitable anti-ischemic agents include, but are not limited to, those described in the Physicians' Desk Reference and NHE inhibitors, including those disclosed in WO 99/43663.

Examples of suitable lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na+/bile acid cotransporter inhibitors, upregulators of LDL receptor activity, bile acid sequestrants, cholesterol ester transfer protein inhibitors (e.g., CP-529414 (Pfizer)), and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983, and U.S. Pat. No. 5,962,440.

The HMG CoA reductase inhibitors which may be employed in combination with one or more compounds of formula I include mevastatin and related compounds, as disclosed in U.S. Pat. No. 3,983,140, lovastatin, (mevinolin) and related compounds, as disclosed in U.S. Pat. No. 4,231,938, pravastatin, and related compounds, such as disclosed in U.S. Pat. No. 4,346,227, simvastatin, and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772; cerivastatin, as disclosed in U.S. Pat. Nos. 5,006,530 and 5,177,080; atorvastatin, as disclosed in U.S. Pat. Nos. 4,681,893, 5,273,995, 5,385,929 and 5,686,104; atavastatin (Nissan/Sankyo's nisvastatin (NK-104)), as disclosed in U.S. Pat. No. 5,011,930; visastatin (Shionogi-Astra/Zeneca (ZD-4522)) as disclosed in U.S. Pat. No. 5,260,440.

Preferred hypolipidemic agents are pravastatin, lovastatin, simvastatin, atorvastatin, fluvastatin, cerivastatin, atavastatin, and ZD-4522.

The fibric acid derivatives which may be employed in combination with one or more compounds of formula I include fenofibrate, gemfibrozil, clofibrate, bezafibrate, ciprofibrate, clinofibrate, and the like, probucol, and related compounds, as disclosed in U.S. Pat. No. 3,674,836, fenofibrate and gemfibrozil being preferred, bile acid sequestrants, such as cholestyramine, colestipol and DEAE-Sephadex (Secholex®, Policexide), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in *Drugs of the Future,* 24:9-15 (1999) (Avasimibe); Nicolosi et al., "The ACAT inhibitor, CI-1011 is effective in the prevention and regression of aortic fatty streak area in hamsters", *Atherosclerosis* (Shannon, Irel.), 137(1): 77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.,* 16(1):16-30 (1998); Smith, C. et al., "RP 73163: a bioavailable alkylsulfinyl-diphenylimidazole ACAT inhibitor", *Bioorg. Med. Chem. Lett.,* 6(1):47-50 (1996); Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways,* CRC Press, Inc., publ., Ruffolo, Jr., R. R. et al., eds., pp. 173-198 (1995); Sliskovic et al., "ACAT inhibitors: potential anti-atherosclerotic agents", *Curr. Med. Chem.,* 1(3):204-25 (1994); Stout et al., "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl] ureas with enhanced hypocholesterolemic activity", *Chemtracts: Org. Chem.*, 8(6):359-362 (1995), or TS-962 (Taisho Pharmaceutical Co. Ltd.).

The hypolipidemic agent may be an upregulator of LDL receptor activity, such as MD-700 (Taisho Pharmaceutical Co. Ltd) and LY295427 (Eli Lilly).

Examples of suitable cholesterol absorption inhibitors for use in combination with the compounds of the invention include ezetimibe (Zetia®).

Examples of suitable ileal $Na^+$/bile acid cotransporter inhibitors for use in combination with the compounds of the invention include compounds as disclosed in *Drugs of the Future*, 24:425-430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", *Brit. J. Pharmacology*, 120:1199-1206 (1997), and Cornicelli et al., "15-Lipoxygenase and its Inhibition: A Novel Therapeutic Target for Vascular Disease", *Current Pharmaceutical Design*, 5:11-20 (1999).

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a cannabinoid receptor 1 antagonist or inverse agonist, a beta 3 adrenergic agonist, a lipase inhibitor, a serotonin (and dopamine) reuptake inhibitor, a thyroid receptor beta drug, and/or an anorectic agent.

Cannabinoid receptor I antagonists and inverse agonists which may be optionally employed in combination with compounds of the present invention include rimonabant, SLV 319, CP-945598 (Pfizer), SR-147778 (Sanofi-Aventis), MK0364 (Merck) and those discussed in Hertzog, D. L., *Expert Opin. Ther. Patents*, 14:1435-1452 (2004).

The beta 3 adrenergic agonists which may be optionally employed in combination with compounds of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983, and 5,488,064, with AJ9677, L750, 355, and CP331648 being preferred.

Examples of lipase inhibitors which may be optionally employed in combination with compounds of the present invention include orlistat or ATL-962 (Alizyme), with orlistat being preferred.

The serotonin (and dopamine) reuptake inhibitor and/or modulator which may be optionally employed in combination with a compound of formula I may be sibutramine, topiramate (Johnson & Johnson), APD-356 (Arena) or axokine (Regeneron), with sibutramine and APD-356 being preferred.

Examples of thyroid receptor beta compounds which may be optionally employed in combination with compounds of the present invention include thyroid receptor ligands, such as those disclosed in WO 97/21993 (U. Cal SF), WO 99/00353 (KaroBio), and WO 00/039077 (KaroBio), with compounds of the KaroBio applications being preferred.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); MCHR1 antagonist (e.g., GSK 856464); galanin receptor antagonists; MCR-4 antagonists (e.g., HP-228); leptin or mimetics; urocortin mimetics, CRF antagonists, and CRF binding proteins (e.g., RU-486, urocortin).

Further, the compounds of the present invention may be used in combination with HIV protease inhibitors, including but not limited to Reyataz® and Kaletra®.

Examples of suitable memory enhancing agents, anti-dementia agents, or cognition promoting agents for use in combination with the compounds of the present invention include, but are not limited to, donepezil, rivastigmine, galantamine, memantine, tacrine, metrifonate, muscarine, xanomelline, deprenyl and physostigmine.

Examples of suitable anti-inflammatory agents for use in combination with the compounds of the present invention include, but are not limited to, prednisone, acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha, prednisolone, methylprednisolone, dexamethazone, flucatisone, betamethasone, hydrocortisone and beclomethasone.

The aforementioned patents and patent applications are incorporated herein by reference.

The above other therapeutic agents, when employed in combination with the compounds of the present invention may be used, for example, in those amounts indicated in the Physicians' Desk Reference, as in the patents set out above, or as otherwise determined by one of ordinary skill in the art.

The compounds of formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of structure I (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

What is claimed is:

1. A compound of formula (Ia)

W-L-Z (Ia) and/or enantiomers, diastereomers or pharmaceutically acceptable salts thereof, wherein:

W is $—C(=O)R_6$, $—C(OH)R_6(R_6)$, $—C(=O)OR_6$, $—C(=O)NR_6R_6$, alkyl, alkenyl, aryl, cycloalkyl, heteroaryl or heterocyclyl, wherein the alkyl, alkenyl, aryl, cycloalkyl, heteroaryl or heterocyclyl may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, $—OH$, $—CN$, $-NO_2$, $—CO_2R_6$, $—CONR_6R_6$, $—SO_2NR_6R_6$, $—SOR_6$, $—SO_2R_6$, $—NR_6SO_2R_6$, $—NR_6CO_2R_6$, $—OCONR_6R_6$, tetrazolyl, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

or alternatively any two $R_1$, $R_{1a}$, $R_{1b}$, $R_{1c}$ and $R_{1d}$ can be taken together to form a fused cycloalkyl, aryl, heteroaryl, heterocyclyl ring or spiro heterocyclyl ring;

L is a bond, O, SO, $SO_2$, $C(=O)$, alkenyl, cycloalkyl, $CR_2R_{2a}$, $CR_2R_6$, $CR_2R_{2a}CR_{2b}R_{2c}$, $SO_2NR_6$, $OCR_2R_{2a}$, $OCR_2R_{2a}CR_{2b}R_{2c}$, $CR_2R_{2a}O$, $CR_{2b}R_{2c}CR_2R_{2aO, N(R5)}$) $CR_2R_{2a}$, $_{CR2}R_{2a}SO$, $CR_2R_{2a}SO_2$, $SOCR_2R_{2a}$, $SO_2CR_2R_2$, $CR_2R_{2a}OCR_{2b}R_{2c}$, $CR_2R_{2a}SCR_{2b}R_{2c}$, $CR_2R_{2a}SO_2CR_{2b}R_{2c}$, $SO_2NR_6CR_2R_{2b}$, $COCR_2R_{2a}$, $CR_2R_{2a}CO$, $CONR_6CR_2R_{2b}$, $CR_2R_{2a}CR_{2b}R_{2c}S$, $CR_2R_{2a}CR_{2b}R_{2c}SO$, $CR_2R_{2a}CR_{2b}R_{2c}SO_2$;

$R_2$, $R_{2a}$, $R_{2b}$ and $R_{2c}$ are independently hydrogen, halogen, $—OH$, alkyl, cycloalkyl, aryl, or haloalkyl;

or alternatively any two $R_2$, $R_{2a}$, $R_{2b}$, and $R_{2c}$ can be taken together to which the atom they are attached to form a cycloalkyl, halogen substituted cycloalkyl or heterocyclyl ring; Z is:

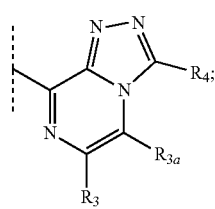

(a)

$R_3$ is hydrogen, halogen, $—OH$, $—CN$, $—NO_2$, $—CO_2R_6$, $—CONR_6R_6$, $—SO_2NR_6R_6$, $—SOR_6$, $—SO_2R_6$, $—NR_6SO_2R_6$, $—NR_6CO_2R_6$, $—OCONR_6R_6$, tetrazolyl, alkyl, haloalkyl, cycloalkyl, alkoxy, aryloxy, alkenyl, haloalkoxy, alkylthio, arylthio, arylsulfonyl, alkylamino, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_{1a}$ is hydrogen, halogen, $—OH$, $—CN$, $—NO_2$, $—CO_2R_6$, $—CONR_6R_6$, $—SO_2NR_6R_6$, $—SOR_E$, $—SO_2R_6$, $—NR_6SO_2R_6$, $—NR_6CO_2R_6$, $—OCONR_6R_6$, tetrazolyl, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_4$ is cycloalkyl, which may be optionally substituted with one or more substituents selected from halogen, $—SR_6$, $—OCOR_6$, $—CN$, $—NR_6COR_6$, $—NR_6SO_2R_6$, $—COR_E$, $—CO_2R_6$, $—OCONR_6R_6$, $—CONR_6R_6$, $—NR_6CO_2R_6$, $—SO_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; or $R_4$ is heterocyclyl, which may be optionally substituted with one or more substituents selected from halogen, $—OR_6$, $—SR_6$, $—OCOR_6$, $—CN$, $—NR_6COR_6$, $—NR_6SO_2R_6$, $—COR_E$, $—CO_2R_6$, $—OCONR_6R_6$, $—CONR_6R_6$, $—NR_6CO_2R_6$, $—SO_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; or $R_4$ is alkyl substituted with one or more substituents selected from $—OR_6$, $—SR_6$, $—OCOR_6$, $—CN$, $—NR_6COR_6$, $—NR_6SO_2R_6$, $—COR_6$, $—OCONR_6R_6$, $—CONR_6R_6$, $—NR_6CO_2R_6$, $—SO_2R_6$, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_5$, at each occurrence, is independently hydrogen, alkyl, cycloalkyl, aryl, haloalkyl, $COR_6$, $CO_2R_6$, $SO_2NR_6R_6$, or $SO_2R_6$;

$R_6$, at each occurrence, is independently H, alkyl, cycloalkyl, aryl or heteroaryl, all of which, where possible, may be optionally substituted with $R_7$, $R_{7a}$, $R_{7b}$, and $R_{7c}$; or two $R_6$'s may be taken together with the atom to which they are attached to form a 3- to 7-membered cycloalkyl or heterocyclyl ring, which may be optionally substituted with $R_7$, $R_{7a}$, $R_{7b}$ and $R_{7c}$;

$R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, -OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with $R_g$, $R_{ga}$, $R_{gb}$, and $R_{8c}$; and $R_g$, $R_{ga}$, $R_{gb}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol.

2. The compound as defined in claim 1, wherein W is alkyl, aryl, cycloalkyl, heteroaryl or heterocyclyl, all of which may be optionally substituted with $R_1$, $R_{1a}$, $R_{1b}$, $R_{1c}$ and $R_{1d}$.

3. The compound as defined in claim 1, wherein W is phenyl or cyclopropyl, both of which are optionally substituted with $R_1$, $R_{1a}$, $R_{1b}$, $R_{1c}$ and $R_{1d}$.

4. The compound as defined in claim 1, wherein: $R_4$ is cycloalkyl, which may be optionally substituted with one or more substituents selected from halogen, —OH, —$OR_6$, —$SR_6$, —$OCOR_6$, —CN, —$NR_6COR_6$, —$NR_6SO_2R_6$, —$COR_E$, —$CO_2R_6$, —$CO_2H$, —$OCONR_6R_6$, —$CONR_6R_6$, —$NR_6CO_2R_6$, —$SO_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; or $R_4$ is alkyl substituted with one or more substituents selected from —OH, —$OR_6$, —$SR_6$, —$OCOR_6$, —CN, —$NR_6COR_6$, —$NR_6SO_2R_6$, —$COR_6$, —$OCONR_6R_6$, —$CONR_6R_6$, —$NR_6CO_2R_6$, —$SO_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_5$, at each occurrence, is independently hydrogen, alkyl, cycloalkyl, aryl, haloalkyl, $COR_6$, $CO_2R_6$, $SO_2NR_6R_6$, or $SO_2R_6$;

$R_6$, at each occurrence, is independently alkyl, cycloalkyl, aryl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with $R_8$, $R_{8a}$, $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol.

5. The compound as defined in claim 1, wherein:

W is alkyl, aryl, cycloalkyl, heteroaryl or heterocyclyl, all of which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —$NO_2$, —$CO_2R_6$, —$CONR_6R_6$, —$SO_2NR_6R_6$, —$SOR_6$, —$SO_2R_6$, —$NR_6SO_2R_6$, —$NR_6CO_2R_6$, —$OCONR_6R_6$, tetrazolyl, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

L is a bond, $SO_2$, C(=O), $CR_2R_{2a}$, $CR_2R_6$, $SO_2NR_6$, $OCR_2R_{2a}$, $OCR_2R_{2a}CR_{2b}R_{2c}$, $CR_2R_{2a}O$, $CR_{2b}R_{2c}CR_2R_{2a}O$, $CR_2R_{2a}SO$, $CR_2R_{2a}SO$, $SO_2CR_2R_{2a}$, $CR_2R_{2a}OCR_{2b}R_{2c}$, $CR_2R_{2a}SCR_{2b}R_{2c}$, $CR_2R_{2a}SO_2CR_{2b}R_{2c}$, $SO_2NR_6CR_{2a}R_{2b}$, $COCR_2R_{2a}$, $CR_2R_{2a}CO$, $CONR_6CR_{2a}R_{2b}$, $CR_2R_{2a}CR_{2b}R_{2c}$, $CR_2R_{2a}CR_{2b}R_{2c}SO$ or $CR_2R_{2a}CR_{2b}R_{2c}SO_2$;

$R_2$, $R_{2a}$, $R_{2b}$ and $R_2$ are independently hydrogen, halogen, —OH, alkyl, cycloalkyl, aryl or haloalkyl;

$R_3$ is hydrogen, halogen, —OH, —CN, —$NO_2$, —$CO_2R_6$, —$CONR_6R_6$, —$SO_2NR_6R_6$, —$SOR_6$, —$SO_2R_6$, —$NR_6SO_2R_6$, —$NR_6CO_2R_6$, —$OCONR_6R_6$, tetrazolyl, alkyl, haloalkyl, cycloalkyl, alkoxy, aryloxy, alkenyl, haloalkoxy, alkylthio, arylthio, arylsulfonyl, alkylamino, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_{3a}$ is hydrogen, halogen, —OH, —CN, —$NO_2$, —$CO_2R_6$, —$CONR_6R_6$, —$SO_2NR_6R_6$, —$SOR_6$, —$SO_2R_6$, —$NR_6SO_2R_6$, —$NR_6CO_2R_6$, —$OCONR_6R_6$, tetrazolyl, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_4$ is cycloalkyl, which may be optionally substituted with one or more substituents selected from halogen, —OH, —$OR_6$, —$SR_6$, —$OCOR_6$, —CN, —$NR_6COR_6$, —$NR_6SO_2R_6$, —$COR_6$, —$CO_2R_6$, —$CO_2H$, —$OCONR_6R_6$, —$CONR_6R_6$, —$NR_6CO_2R_6$, —$SO_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; or $R_4$ is alkyl substituted with one or more substituents selected from halogen, OH, -$OR_6$, $^-SR_6$, —$OCOR_6$, —CN, —$NR_6COR_6$, —$NR_6SO_2R_6$, —$COR_6$, —$OCONR_6R_6$, —$CONR_6R_6$, —$NR_6CO_2R_6$, —$SO_2R_6$, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_5$, at each occurrence, is independently hydrogen, alkyl, cycloalkyl, aryl, haloalkyl, $COR_6$ or $CO_2R_6$;

$R_6$, at each occurrence, is independently alkyl, cycloalkyl, aryl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, -OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, -$NO_2$, -CN, -$CO_2H$, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with $R_8$, $R_{8a}$, $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, -OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol.

6. The compound as defined in claim 1, wherein:

W is alkyl, aryl, cycloalkyl or heteroaryl, all of which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —$NO_2$, —$CO_2R_6$, —$CONR_6R_6$, —$SO_2NR_6R_6$, —$SOR_6$, —$SO_2R_6$, —$OCONR_6R_6$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

L is a bond, O, SO, $SO_2$, C(=O), $CR_2R_{2a}$, $CR_2R_6$, $CR_2R_{2a}CR_{2b}R_{2c}$, $OCR_2R_{2a}$, $CR_2R_{2a}O$, $CR_2R_{2a}OCR_{2b}R_{2c}$, $CR_2R_{2a}SCR_{2b}R_{2c}$, $CR_2R_{2a}SO_2CR_{2b}R_{2c}$ or $SO_2NR_6CR_{2a}R_{2b}$;

$R_2$, $R_{2a}$, $R_{2b}$ and $R_{2c}$ are independently hydrogen, halogen, —OH, alkyl, cycloalkyl, aryl or haloalkyl;

$R_3$ is hydrogen, halogen, —OH, —CN, —$NO_2$, —$CO_2R_6$, —$CONR_6R_6$, —$SO_2NR_6R_6$, —$SOR_6$, —$SO_2R_6$, —$OCONR_6R_6$, tetrazolyl, alkyl, haloalkyl, cycloalkyl, alkoxy, aryloxy, haloalkoxy, alkylthio, arylthio, arylsulfonyl, alkylamino, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_{3a}$ is hydrogen, halogen, —OH, —CN, —$NO_2$, —$CO_2R_6$, —$CONR_6R_6$, —$SO_2NR_6R_6$, —$SOR_6$, —$SO_2R_6$, —$OCONR_6R_6$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_4$ is cycloalkyl, which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_6R_6$, —$CONR_6R_6$, —$SO_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; or $R_4$ is alkyl substituted with one or more substituents selected from —OH, —$OR_6$, —$SR_6$, —$OCOR_6$, —CN, —$COR_6$, —$OCONR_6R_6$, —$CONR_6R_6$, —$SO_2R_6$, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with Rg, $R_{8a}$, $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol.

7. The compound as defined in claim 1, wherein:

W is alkyl, aryl or cycloalkyl, all of which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —$NO_2$, —$CO_2R_6$, —$CONR_6R_6$, —$SO_2NR_6R_6$, —$OCONR_6R_6$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

L is a bond, O, SO, $SO_2$, C(=O), $CR_2R_{2a}$, $CR_2R_6$, $OCR_2R_{2a}$, $CR_2R_{2a}O$, $SO_2NR_6CR_2{_a}R_{2b}$ or $CR_2R_{2a}OCR_{2b}R_{2c}$;

$R_2$, $R_{2a}$, $R_{2b}$ and $R_2$ are independently hydrogen, halogen, —OH, alkyl, cycloalkyl, aryl or haloalkyl;

$R_3$ is hydrogen, halogen, —OH, —CN, —$NO_2$, —$CO_2R_6$, —$CONR_6R_6$, —$SO_2NR_6R_6$, —$OCONR_6R_6$, tetrazolyl, alkyl, haloalkyl, cycloalkyl, alkoxy, aryloxy, haloalkoxy, alkylthio, arylthio, arylsulfonyl, alkylamino, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_{3a}$ is hydrogen, halogen, —OH, —CN, —$NO_2$, —$CO_2R_6$, —$CONR_6R_6$, —$SO_2NR_6R_6$, —$OCONR_6R_6$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_4$ is cycloalkyl, which may be optionally substituted with one or more substituents selected from halogen, —OH, —$OR_6$, —$SR_6$, —$OCOR_6$, —CN, —$COR_6$, —$CO_2R_6$, -$CO_2H$, -$OCONR_6R_6$, -$CONR_6R_6$, —$SO_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; or $R_4$ is alkyl substituted with one or more substituents selected from —OH, —$OR_6$, —$SR_6$, —$OCOR_6$, —CN, —$COR_6$, —$OCONR_6R_6$, —$CONR_6R_6$, —$SO_2R_6$, cycloalkyl, spiro cycloalkyl, spiro heterocycloalkyl, aryl, amino, heterocyclyl or heteroaryl, wherein the alkyl, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with $R_8$, $R_{8a}$, $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, -OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol.

8. The compound as defined in claim 1, wherein:

W is alkyl, aryl or cycloalkyl, all of which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —$NO_2$, —$CO_2R_6$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

L is a bond, O, SO, $SO_2$, C(=O), $CR_2R_{2a}$, $CR_2R_6$, $OCR_2R_{2a}$, $CR_2R_{2a}O$, $SO_2NR_6CR_2{_a}R_{2b}$ or $CR_2R_{2a}OCR_{2b}R_{2c}$;

$R_2$, $R_{2a}$, $R_{2b}$ and $R_2$ are independently hydrogen, halogen, —OH, alkyl, cycloalkyl, aryl or haloalkyl;

$R_3$ is hydrogen, halogen, —OH, —CN, —$NO_2$, —$CO_2R_6$, tetrazolyl, alkyl, haloalkyl, cycloalkyl, alkoxy, aryloxy, haloalkoxy, alkylthio, arylthio, arylsulfonyl, alkylamino, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_{3a}$ is hydrogen, halogen, —OH, —CN, —$NO_2$, —$CO_2R_6$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_4$ is cycloalkyl, which may be optionally substituted with one or more substituents selected from halogen, —OH, —$OR_6$, —$SR_6$, —CN, —$COR_E$, —$CO_2R_6$, —$CO_2H$, —$CONR_6R_6$, —$SO_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; or $R_4$ is alkyl substituted with one or more substituents selected from —OH, —$OR_6$, —$SR_6$, —CN, —$COR_6$, —$CONR_6R_6$, —$SO_2R_6$, alkoxy, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, -OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, -$NO_2$, -CN, -$CO_2H$, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with $R_8$, $R_{8a}$, $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, -OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol.

9. The compound as defined in claim 1, wherein:

W is alkyl, aryl or cycloalkyl, all of which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —$NO_2$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

L is a bond, O, SO, $SO_2$, C(=O), $CR_2R_{2a}$, $CR_2R_6$, $OCR_2R_{2a}$, $CR_2R_{2aO}$, $SO_2NR_6CR_{2a}R_{2b}$ or $CR_2R_{2a}OCR_{2b}R_{2c}$;

$R_2$, $R_{2a}$, $R_{gb}$ and $R_{2c}$ are independently hydrogen, halogen, —OH, alkyl, cycloalkyl, aryl or haloalkyl;

$R_3$ is hydrogen, halogen, —OH, —CN, —$NO_2$, tetrazolyl, alkyl, haloalkyl, cycloalkyl, alkoxy, aryloxy, haloalkoxy, alkylthio, arylthio, arylsulfonyl, alkylamino, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_{3a}$ is hydrogen, halogen, —OH, —CN, —$NO_2$, tetrazolyl, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_4$ is alkyl substituted with one or more substituents selected from —OH, $OR_6$, —$SR_6$, —CN, —$COR_6$, —$CONR_6R_6$, —$SO_2R_6$, alkoxy, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$;

$R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, -OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, -$NO_2$, -CN, -$CO_2H$, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with $R_8$, $R_{8a}$, $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, -OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol.

10. The compound as defined in claim 1, wherein:

W is aryl or cycloalkyl, both of which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are hydrogen, halogen, —OH, —CN, —$NO_2$, tetrazolyl, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

L is a bond, O, C(=O), $CR_2R_{2a}$, $CR_2R_6$, $OCR_2R_{2a}$, $CR_2R_{2a}0$ or $CR_2R_{2aOCR2b}R_{2c}$; $R_2$, $R_{2a}$, $R_{2b}$ and $R_2$ are independently hydrogen, halogen, —OH, alkyl, cycloalkyl, aryl or haloalkyl;

$R_3$ is hydrogen, halogen, —OH, —CN, —$NO_2$, tetrazolyl, alkyl, haloalkyl, cycloalkyl, alkoxy, aryloxy, haloalkoxy, alkylthio, arylthio, arylsulfonyl, alkylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_{3a}$ is hydrogen, halogen, —OH, —CN, —$NO_2$, tetrazolyl, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_4$ is cycloalkyl, which may be optionally substituted with one or more substituents selected from halogen, —OH, —$OR_6$, —$SR_6$, —CN, —$COR_6$, —$CO_2R_6$, —$CO_2H$, alkyl, alkoxy, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; or $R_4$ is alkyl substituted with one or more substituents selected from —OH, —$OR_6$, —$SR_6$, —CN, —$COR_6$, —$CONR_6R_6$, —$SO_2R_6$, alkoxy, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl; $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with $R_8$, $R_{8a}$, $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol.

11. The compound as defined in claim 1, wherein:

W is phenyl or cyclopropyl, both of which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —$NO_2$, tetrazolyl, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl;

L is a bond, O, C(=O), $CHR_6$, $OCH_2$, $CH_2O$ or $CH_2OCH_2$;

$R_3$ is hydrogen, halogen, —OH, —CN, —$NO_2$, tetrazolyl, alkyl, haloalkyl, cycloalkyl, alkoxy, aryloxy, haloalkoxy, alkylthio, arylthio, arylsulfonyl, alkylamino, aryl, heteroaryl or heterocyclyl;

$R_{1a}$ is hydrogen, halogen, —OH, —CN, —$NO_2$, tetrazolyl, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl;

$R_4$ is cycloalkyl, which may be optionally substituted with one or more substituents selected from halogen, —OH, —$OR_6$, —$SR_6$, —CN, alkyl, alkoxy, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; or $R_4$ is alkyl substituted with one or more substituents selected from —OH, —$OR_6$, —$SR_6$, —CN, —$COR_6$, —$CONR_6R_6$, —$SO_2R_6$, alkoxy, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl;

$R_7$, $R_{7a}$, $R_{7b}$, and $R_{7c}$, at each occurrence, are independently halo, alkyl, haloalkyl, alkoxy, aryl, aryloxy, arylalkyl, cycloalkyl, amino, -OH, hydroxyalkyl, heteroaryl, heteroaryloxy, heteroarylalkyl, alkylthio, arylalkylthio, -$NO_2$, -CN, -$CO_2H$ or tetrazolyl; wherein the alkyl, alkoxy, aryl, aryloxy, arylalkyl, cycloalkyl, heteroaryl, heteroaryloxy, heteroarylalkyl, alkylthio, arylalkylthio or tetrazolyl may be optionally substituted with $R_8$, $R_{8a}$, $R_{8b}$, and $R_{8c}$; and $R_8$, $R_{8a}$, $R_{8b}$, and $R_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, -OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol.

12. The compound as defined in claim 1, wherein L is a bond or O.

13. The compound as defined in claim 1 selected from the compounds of the structure:

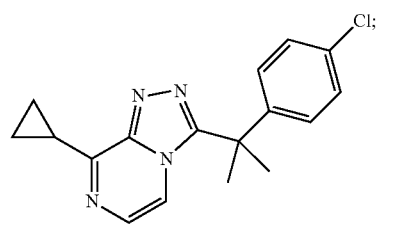

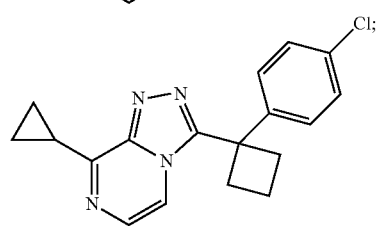

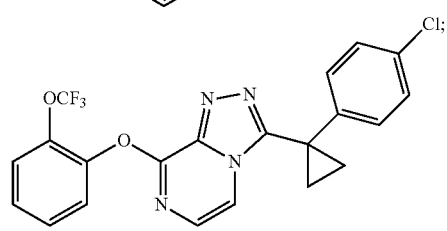

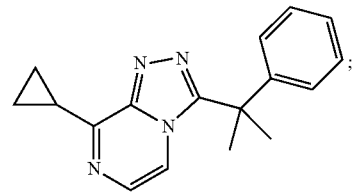

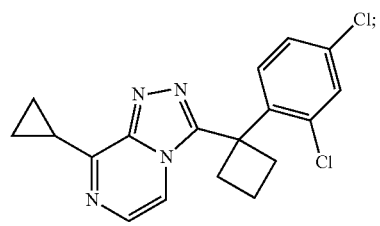

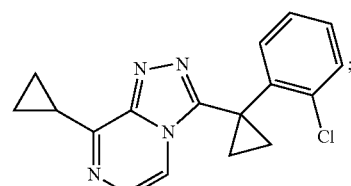

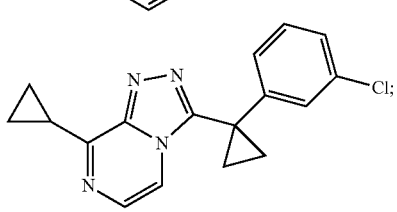

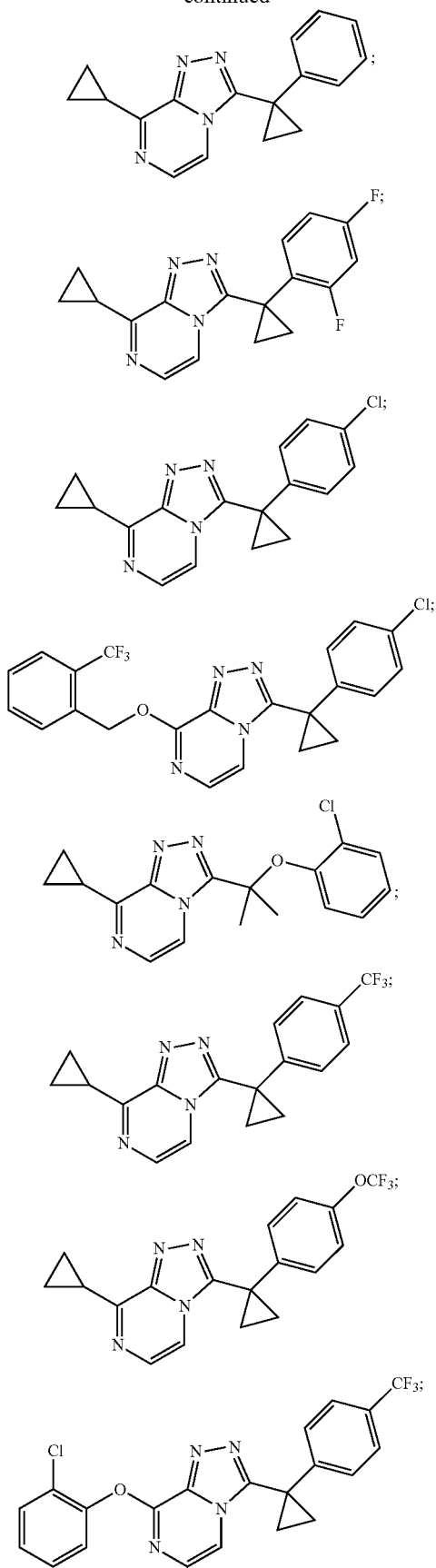
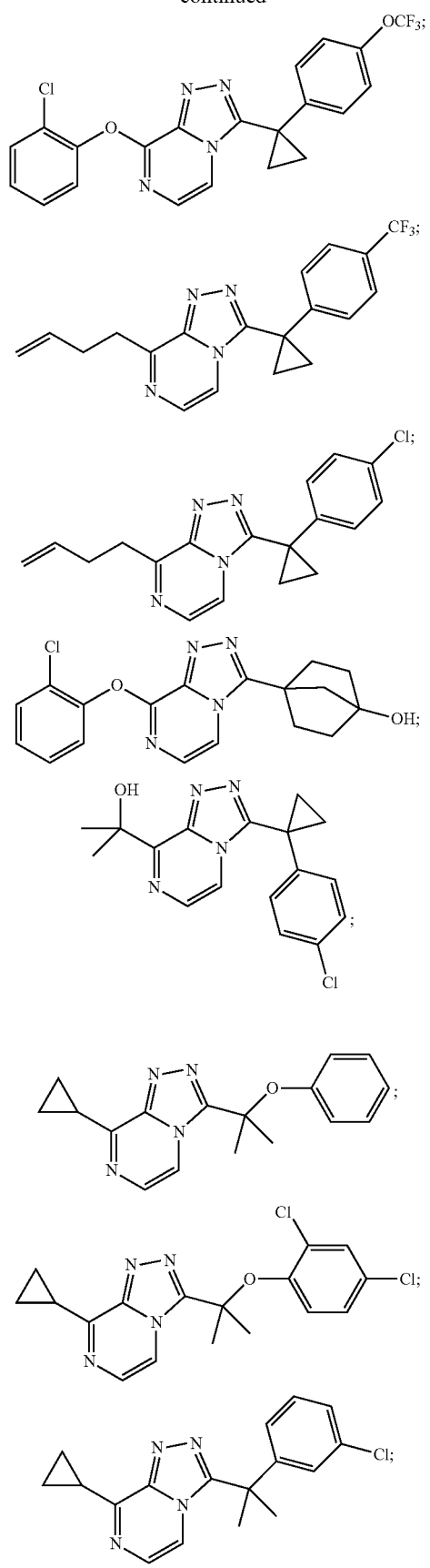

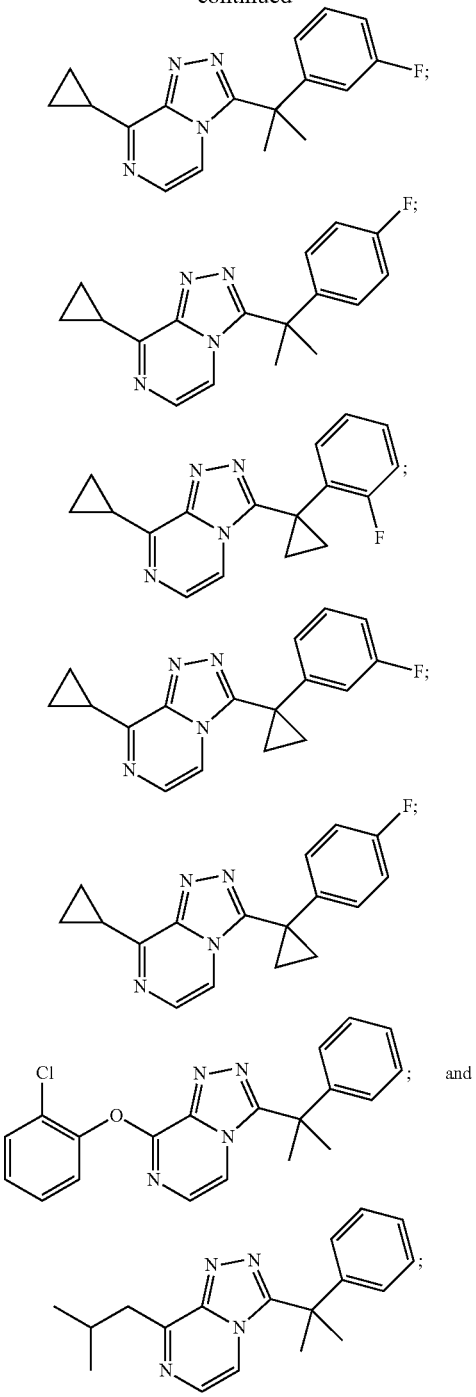

or a pharmaceutically acceptable salt thereof.

14. A pharmaceutical composition comprising at least one compound of claim 1 and a pharmaceutically acceptable carrier.

15. A compound of formula (Ib)

W-L-Z (Ib)

and/or enantiomers, diastereomers or pharmaceutically acceptable salts thereof, wherein:

W is —C(=O)$R_6$, —C(OH)$R_6$($R_6$), —C(=O)O$R_6$, —C(=O)N$R_6R_6$, alkyl, alkenyl, aryl, or cycloalkyl, heteroaryl or heterocyclyl, wherein the alkyl, alkenyl, aryl, cycloalkyl, heteroaryl or heterocyclyl may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —NO$_2$, —CO$_2R_6$, —CONR$_6R_6$, —SO$_2$NR$_6R_6$, —SOR$_6$, —SO$_2R_6$, —NR$_6$SO$_2R_6$, —NR$_6$CO$_2R_6$, —OCONR$_6R_6$, tetrazolyl, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

or alternatively any two $R_1$, $R_{1a}$, $R_{1b}$, $R_{1c}$ and $R_{1d}$ can be taken together to form a fused cycloalkyl, aryl, heteroaryl, heterocyclyl ring or spiro heterocyclyl ring;

L is a bond or O;

Z is

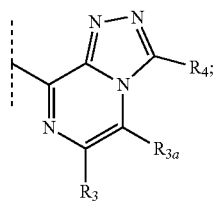

$R_3$ is hydrogen, halogen, —OH, —CN, —NO$_2$, —CO$_2R_6$, —CONR$_6R_6$, —SO$_2$NR$_6R_6$, —SOR$_6$, —SO$_2R_6$, —NR$_6$SO$_2R_6$, —NR$_6$CO$_2R_6$, —OCONR$_6R_6$, tetrazolyl, alkyl, haloalkyl, cycloalkyl, alkoxy, aryloxy, alkenyl, haloalkoxy, alkylthio, arylthio, arylsulfonyl, alkylamino, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_{3a}$ is hydrogen, halogen, —OH, —CN, —NO$_2$, —CO$_2R_6$, —CONR$_6R_6$, —SO$_2$NR$_6R_6$, —SOR$_6$, —SO$_2R_6$, —NR$_6$SO$_2R_6$, —NR$_6$CO$_2R_6$, —OCONR$_6R_6$, tetrazolyl, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with $R_7$, $R_{7a}$, $R_{7b}$, and $R_{7c}$;

$R_4$ is cycloalkyl, which may be optionally substituted with one or more substituents selected from halogen, —OR$_6$, —SR$_6$, —OCOR$_6$, —CN, —NR$_6$COR$_6$, —NR$_6$SO$_2R_6$, —COR$_6$, —CO$_2R_6$, —OCONR$_6R_6$, —CONR$_6R_6$, —NR$_6$CO$_2R_6$, —SO$_2R_6$, alkyl, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with $R_7$, $R_{7a}$, $R_{7b}$, and $R_{7c}$; or $R_4$ is alkyl substituted with one or more substituents selected from —OR$_6$, —SR$_6$, —OCOR$_6$, —CN, —NR$_6$COR$_6$, —NR$_6$SO$_2R_6$, —COR$_6$, —OCONR$_6R_6$, —CONR$_6R_6$, —NR$_6$CO$_2R_6$, —SO$_2R_6$, cycloalkyl, spiro cycloalkyl, spiro heterocycloalkyl, aryl, amino, heterocyclyl or heteroaryl, wherein the alkyl, alkoxy, cycloalkyl, Spiro cycloalkyl, Spiro heterocycloalkyl, aryl, heteroaryl or heterocyclyl may be optionally substituted with $R_7$, $R_{7a}$, $R_{7b}$, and $R_{7c}$;

R$_6$, at each occurrence, is independently H, alkyl, cycloalkyl, aryl or heteroaryl, all of which, where possible, may be optionally substituted with R$_7$, R$_{7a}$, R$_{7b}$, and R$_{7c}$; or two R$_6$'s may be taken together with the atom to which they are attached to form a 3- to 7-membered cycloalkyl or heterocyclyl ring, which may be optionally substituted with R$_7$, R$_{7a}$, R$_{7b}$ and R$_{7c}$;

R$_7$, R$_{7a}$, R$_{7b}$, and R$_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN, —CO$_2$H, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with R$_8$, R$_{8a}$, R$_{8b}$, and R$_{8c}$; and R$_8$, R$_{8a}$, R$_{8b}$, and R$_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN, —CO$_2$H, tetrazolyl or thiol.

16. The compound as defined in claim 15 wherein W is cycloalkyl, aryl, alkenyl or alkyl, wherein the cycloalkyl, aryl, alkenyl or alkyl may be optionally substituted with R$_1$, R$_{1a}$, R$_{1b}$, R$_{1c}$ and R$_{1d}$, R$_3$ is H, and R$_{3a}$ is H.

17. The compound as defined in claim 15 having the following structure;

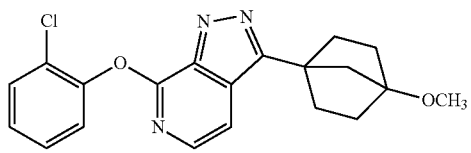

or a pharmaceutically acceptable salt thereof.

18. A compound of formula (I)

W-L-Z    (I)

and/or enantiomers, diastereomers or pharmaceutically acceptable salts thereof, wherein:

W is alkyl, alkenyl, aryl, or cycloalkyl, wherein the alkyl, alkenyl, aryl, or cycloalkyl may be optionally substituted with R$_1$, R$_{1a}$, R$_{1b}$, R$_{1c}$ and R$_{1d}$;

R$_1$, R$_{1a}$, R$_{1b}$, R$_{1c}$ and R$_{1d}$ are independently hydrogen, halogen, —OH, —CN, —NO$_2$, —CO$_2$R$_6$, —CONR$_6$R$_6$, —SO$_2$NR$_6$R$_6$, —SOR$_6$, —SO$_2$R$_6$, —NR$_6$SO$_2$R$_6$, —NR$_6$CO$_2$R$_6$, —OCONR$_6$R$_6$, tetrazolyl, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the tetrazolyl, alkyl, cycloalkyl, aryl, heteroaryl or heterocyclyl may be optionally substituted with R$_7$, R$_{7a}$, R$_{7b}$, and R$_{7c}$;

or alternatively any two R$_1$, R$_{1a}$, R$_{1b}$, R$_{1c}$ and R$_{1d}$ can be taken together to form a fused cycloalkyl, aryl, heteroaryl, heterocyclyl ring or spiro heterocyclyl ring;

L is O;

Z is

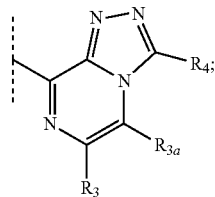

R$_3$ is hydrogen;

R$_{3a}$ is hydrogen;

R$_4$ is cycloalkyl, which may be optionally substituted with one or more substituents selected from halogen, —OR$_6$, —SR$_6$, —OCOR$_6$, —CN, —NR$_6$COR$_6$, —NR$_6$SO$_2$R$_6$, —COR$_6$, —CO$_2$R$_6$, —OCONR$_6$R$_6$, —CONR$_6$R$_6$, —NR$_6$CO$_2$R$_6$, —SO$_2$R$_6$, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with R$_7$, R$_{7a}$, R$_{7b}$, and R$_{7c}$; or R$_4$ is alkyl substituted with one or more substituents selected from halogen, —OR$_6$, —SR$_6$, —OCOR$_6$, —CN, —NR$_6$COR$_6$, —NR$_6$SO$_2$R$_6$, —COR$_6$, —CO$_2$R$_6$, —OCONR$_6$R$_6$, —CONR$_6$R$_6$, —NR$_6$CO$_2$R$_6$, —SO$_2$R$_6$, cycloalkyl, spiro cycloalkyl, spiro heterocycloalkyl, aryl, amino, heterocyclyl or heteroaryl, wherein the alkyl, alkoxy, cycloalkyl, spiro cycloalkyl, spiro heterocycloalkyl, aryl, heteroaryl or heterocyclyl may be optionally substituted with R$_7$, R$_{7a}$, R$_{7b}$, and R$_{7c}$;

R$_6$, at each occurrence, is independently H, alkyl, cycloalkyl, aryl or heteroaryl, all of which may be optionally substituted with R$_7$, R$_{7a}$, R$_{7b}$, and R$_{7c}$; or two R$_6$'s may be taken together with the atom to which they are attached to form a 3- to 7-membered cycloalkyl or heterocyclyl ring, which may be optionally substituted with R$_7$, R$_{7a}$, R$_{7b}$ and R$_{7c}$;

R$_7$, R$_{7a}$, R$_{7b}$, and R$_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN, —CO$_2$H, tetrazolyl or thiol, wherein the alkyl, alkoxy, aryl, aryloxy, arylaryl, arylalkyl, arylalkyloxy, alkenyl, cycloalkyl, cycloalkylalkyl, cycloalkylalkyloxy, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino or tetrazolyl may be optionally substituted with R$_8$, R$_{8a}$, R$_{8b}$, and R$_{8c}$; and R$_8$, R$_{8a}$, R$_{8b}$, and R$_{8c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN, —$CO_2H$, tetrazolyl or thiol.

19. The compound as defined in claim 18 wherein W is aryl, which may be optionally substituted with $R_1$, $R_{1a}$, $R_{1b}$, $R_{1c}$ and $R_{1d}$, $R_3$ is H, $R_{3a}$ is H, and $R_4$ is cycloalkyl, which may be optionally substituted with $R_7$, $R_{7a}$, $R_{7b}$, and $R_{7c}$.

\* \* \* \* \*